US011046700B2

(12) United States Patent
Gardner et al.

(10) Patent No.: US 11,046,700 B2
(45) Date of Patent: Jun. 29, 2021

(54) SUBSTITUTED IMIDAZO[1,2-A]PYRAZINES, PYRAZOLO[1,5-C]PYRIMIDINES, PYRAZOLO[1,5-A]PYRIDINES, AND PURINES FOR THE TREATMENT OF SCHISTOSOMIASIS

(71) Applicant: Merck Patent GmbH, Darmstadt (DE)

(72) Inventors: John Mark Francis Gardner, Sandwich (GB); Andrew Simon Bell, Deal (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 16/477,574

(22) PCT Filed: Jan. 15, 2018

(86) PCT No.: PCT/GB2018/050101
§ 371 (c)(1),
(2) Date: Jul. 12, 2019

(87) PCT Pub. No.: WO2018/130853
PCT Pub. Date: Jul. 19, 2018

(65) Prior Publication Data
US 2020/0123158 A1 Apr. 23, 2020

(30) Foreign Application Priority Data
Jan. 16, 2017 (GB) ..................................... 1700692

(51) Int. Cl.
*A61K 31/437* (2006.01)
*A61K 31/4985* (2006.01)
(Continued)

(52) U.S. Cl.
CPC ............ *C07D 487/04* (2013.01); *A61P 33/12* (2018.01); *C07F 9/6561* (2013.01)

(58) Field of Classification Search
CPC .............. A61K 31/437; A61K 31/4985; A61K 31/519; A61K 31/52; C07D 471/04; C07D 473/00; C07D 487/04
(Continued)

(56) References Cited

U.S. PATENT DOCUMENTS 8,748,435 B2 6/2014 Du et al.
2012/0252778 A1 10/2012 Miltz et al.

FOREIGN PATENT DOCUMENTS

WO 2011092293 A2 8/2011
WO 2012080232 A1 6/2012
WO WO 18/130853 * 7/2018

OTHER PUBLICATIONS

Jordan, V. C. Nature Reviews: Drug Discovery, 2, 2003, 205.*
(Continued)

*Primary Examiner* — Douglas M Willis
(74) *Attorney, Agent, or Firm* — Wood, Phillips, Katz, Clark & Mortimer

(57) ABSTRACT

The present invention relates to compounds of formula (1a), formula (1b), formula (1c) or formula (1d):

(1a)

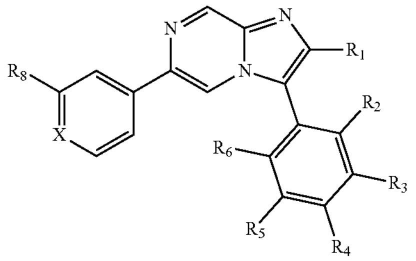

(1b)

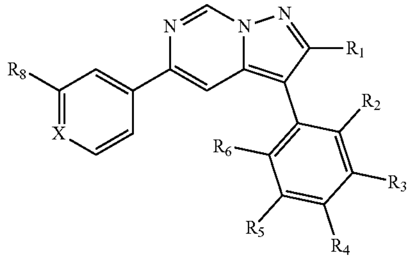

(1c)

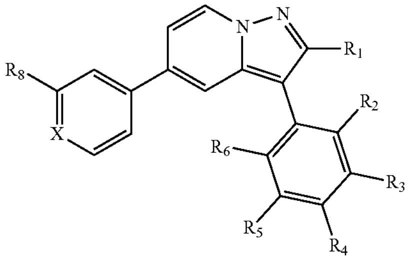

or (1d)

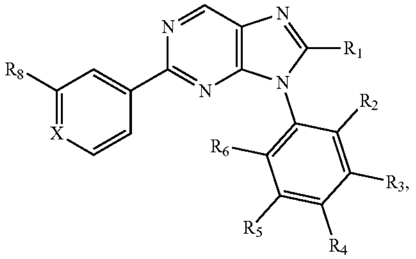

or, or a pharmaceutically acceptable salt thereof, which have activity as inhibitors of *Schistosoma* growth. The invention also relates to pharmaceutical compositions comprising such compounds, salts or solvates and to the use of such compounds as medicaments, in particular in the treatment or prevention of schistosomiasis, also known as *bilharzia*.

26 Claims, No Drawings

(51) Int. Cl.

| | |
|---|---|
| ***A61K 31/519*** | (2006.01) |
| ***A61K 31/52*** | (2006.01) |
| ***C07D 471/04*** | (2006.01) |
| ***C07D 473/00*** | (2006.01) |
| ***C07D 487/04*** | (2006.01) |
| ***A61P 33/12*** | (2006.01) |
| ***C07F 9/6561*** | (2006.01) |

(58) Field of Classification Search
USPC ........... 514/249, 259.3, 263.1, 300; 544/264, 544/282, 350; 546/121
See application file for complete search history.

(56) References Cited

OTHER PUBLICATIONS

Vippagunta, et al. Advanced Drug Delivery Reviews, 48, 2001, 18.*
International Preliminary Report on Patentability for corresponding PCT application No. PCT/GB2018/050101 dated Jul. 16, 2019.

* cited by examiner

SUBSTITUTED IMIDAZO[1,2-A]PYRAZINES, PYRAZOLO[1,5-C]PYRIMIDINES, PYRAZOLO[1,5-A]PYRIDINES, AND PURINES FOR THE TREATMENT OF SCHISTOSOMIASIS

FIELD OF THE INVENTION

This invention relates to compounds of formula (1a), (1b), (1c) and (1d) and pharmaceutically acceptable salts or solvates thereof which have activity as inhibitors of *Schistosoma* growth. The invention also relates to pharmaceutical compositions comprising such compounds, salts or solvates and to the use of such compounds as medicaments, in particular in the treatment or prevention of schistosomiasis, also known as *bilharzia*.

BACKGROUND TO THE INVENTION

Schistosomiasis is one of the major neglected diseases affecting over 200 million people across sub-Saharan Africa, the Middle East and South America. It is a parasitic disease caused by flatworms of the genus *Schistosoma*, such as *S. mansoni, S. haemotobium* and *S. japonicum*. Infections are due to the larval stage of the worm, which then develop through a juvenile stage to adult worms.

Two drugs, praziquantel and oxamniquine, are approved for the treatment of schistosomiasis. Oxamniquine has a narrow spectrum of activity (only *S. mansoni*). Praziquantel is used worldwide against all three worm species but is known to lack efficacy against juvenile worms. Arthemether also shows activity against schistosomes in humans when tested in repeated doses but as it is used extensively in artemesin-based combination therapies for malaria treatment, it is not considered a viable compound for schistosomiasis treatment and control as its use against helminth infections might generate drug-resistant malaria parasites (Keiser J, Utzinger J. Curr Opin Infect Dis. 2007 December; 20(6):605-12).

The current status of research into novel anti-schistomes was the subject of an edition of Future Medicinal Chemistry (2015 Volume 7, Issue 6). There are many examples of repurposing of existing drug molecules and applications of known human drug mechanisms to discover new treatments for schistosomiasis. The former includes Abdulla, M. H., et al. (2009) "*Drug discovery for schistosomiasis; hit and lead compounds identified in a library of known drugs by medium-throughput phenotypic screening*." PLoS Negl Trap Dis 3(7): e478; Dissous, C. and C. G. Grevelding (2011) "*Piggy-backing the concept of cancer drugs for schistosomiasis treatment; a tangible perspective*?" Trends Parasitol 27(2): 59-66; and Neves B. J. "*The antidepressant drug paroxetine as a new lead candidate in schistosome drug discovery*" Medicinal Chemistry Communications, 2016, 7, 1176.

Applications of known human drug targets in the field include Kuntz, A. N., et al. (2007). "*Thioredoxin glutathione reductase from Schistosoma mansoni; an essential parasite enzyme and a key drug target*." PLoS Med 4(6): e206; Long, T., et al. (2010). "*Schistosoma mansoni Polo-like kinase* 1; *A mitotic kinase with key functions in parasite reproduction*." Int J Parasitol 40(9):1075-1086; Rojo-Arreola, L., et al. (2014). "*Chemical and genetic validation of the statin drug target to treat the helminth disease, schistosomiasis* PLoS One 9(1): e87594; Jacques, S. A., et al. (2015). "*Discovery of Potent Inhibitors of Schistosoma mansoni NAD*(+) *Catabolizing Enzyme*." Journal of Medicinal Chemistry 2015 58(8): 3582-3592; Mader, P., et al. (2016). "*Biarylalkyl Carboxylic Acid Derivatives as Novel Antischistosomal Agents*." ChemMedChem 2016, 11, 1-11; Heimburg, T., et al. (2016). "*Structure-Based Design and Synthesis of Novel Inhibitors Targeting HDAC8 from Schistosoma mansoni for the Treatment of Schistosomiasis*." J Chem Inf Model 2014 54(10): 3005-3019 and Journal of Medicinal Chemistry 2016 59(6): 2423-2435.

Large-scale testing on intact *Schistosoma* was limited by the available technology Ramirez B, B. Q et al (2007) "*Schistosomes; challenges in compound screening*." Expert Opinion on Drug Discovery 2: S53-361; Sayed, A. A., et al. (2008) "*Identification of oxadiazoles as new drug leads for the control of schistosomiasis*." Nat Med 14(4): 407-412. We have recently described a novel method for high throughput screening using larval stage *Schistosoma* and subsequently used this methodology to identify a set of hit molecules. Paveley, R. A., et al. (2012) "*Whole organism high-content screening by label-free, image-based Bayesian classification for parasitic diseases*." PLoS Negl Trap Dis 6(7): e1762 and Mansour, N. R., et al. (2016) "*High Throughput Screening Identifies Novel Lead Compounds with Activity against Larval, Juvenile and Adult Schistosoma mansoni PLoS* Negl Trap Dis 10(4): e0004659. The latter paper disclosed an imidazopyrazine derivative (LSHTM-1945) with relatively weak activity of 4.9-6.7 μM against the larval, juvenile and adult stages of *S. mansoni.*

WO2014078813A1 discloses the preparation of imidazopyrazines for treating parasitic diseases, predominantly malaria, leishmaniasis and trypanosomiasis. WO2012080232A1 discloses the preparation of substituted imidazopyrazines as Mps-1 and TKK inhibitors useful in the treatment of hyperproliferative disorders. WO2007096764A2 discloses the preparation of bicyclic heteroaryl derivatives as cannabinoid receptor modulators. In addition, Kayagil, I. and S. Demirayak (2011). "*Synthesis of some* 2,3,6,8-*tetraarylimidazo*[1,2-*a*]*pyrazine derivatives by using either reflux or microwave irradiation method, and investigation their anticancer activities*." Turk. J. Chem. 35(1): 13-24. WO2016133935 discloses a series of pyrazolo [1,5-c]pyrimidines as kinase inhibitors for the treatment of a variety of cancers.

There remains a need in the art for further compounds active as anti-schistosomes with good pharmacokinetic properties, combined with sufficient activity against all three main infective species of worm and against both juvenile and adult worms.

SUMMARY OF THE INVENTION

In a first embodiment, the invention provides a compound of formula (1a), (1b), (1c) or (1d) or a pharmaceutically acceptable salt or solvate thereof, (1a)

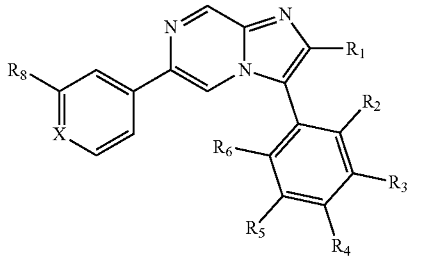

-continued (1b)

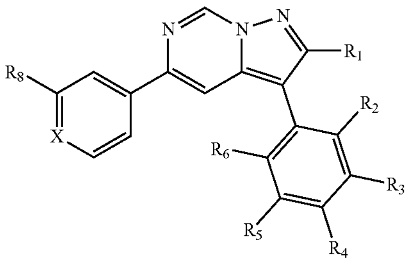

(1c)

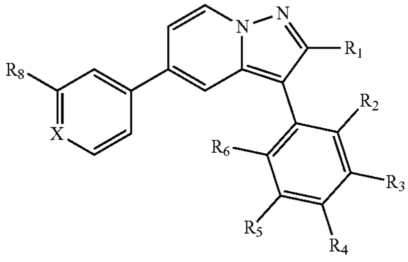

(1d)

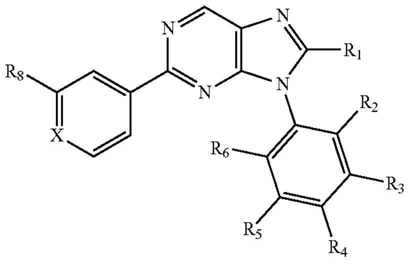

wherein:

$R_1$ is $C_1$-$C_4$ alkyl optionally substituted with up to five F atoms, $C_3$-$C_6$ cycloalkyl optionally substituted with one methyl group, or $C_4$-$C_7$ cycloalkylmethyl;

$R_2$ is H, F, Cl or OMe;

$R_3$ is H, OH, OMe, OPO(OH)OH or $OCH_2OPO(OH)OH$;

$R_4$ is H, OH, OMe, OPO(OH)OH or $OCH_2OPO(OH)OH$;

provided that $R_3$ and $R_4$ cannot both be H;

or $R_3$ and $R_4$ combine, together with the phenyl ring to which they are attached, to form an indazole group as shown below

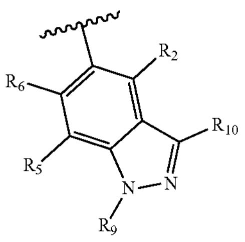

or

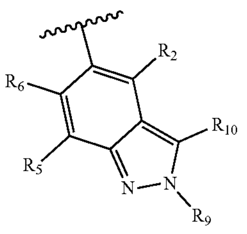

$R_5$ is H, F, Cl or OMe;

$R_6$ is H, F, Cl or OMe;

X is N or C—$R_7$ $R_7$ (where present) is H or F;

$R_8$ is $SF_5$, Br, $C_1$-$C_3$ alkyl optionally substituted with up to seven F atoms, $C_3$-$C_4$ cycloalkyl, $OCH_2C{\equiv}CH$ or $OC_1$-$C_3$ alkyl optionally substituted with up to seven F atoms;

$R_9$ is H; and $R_{10}$ is H, F or Me.

In a second embodiment, the present invention provides a compound of formula (1a), (1b), (1c) or (1d) as defined above, or a pharmaceutically acceptable salt or solvate thereof, for use in therapy.

In a third embodiment, the present invention provides a compound of formula (1a), (1b), (1c) or (1d), as defined above, or a pharmaceutically acceptable salt or solvate thereof, for use in the treatment of schistosomiasis.

In a fourth embodiment, the present invention provides the use of a compound of formula 1a), (1b), (1c) or (1d) as defined above, or a pharmaceutically acceptable salt or solvate thereof, for the manufacture of a medicament for the treatment of schistosomiasis.

In a fifth embodiment, the present invention provides a method for treating schistosomiasis comprising administering a therapeutically effective amount of a compound of formula (1a), (1b), (1c) or (1d) as defined above, or a pharmaceutically acceptable salt or solvate thereof, to a patient in need thereof.

In a sixth embodiment, the present invention provides a pharmaceutical composition comprising (i) a therapeutically effective amount of a compound of formula (1a), (1b), (1c) or (1d) as defined above, or a pharmaceutically acceptable salt or solvate thereof; and (ii) a pharmaceutically acceptable excipient.

DETAILED DESCRIPTION OF THE INVENTION

A. Definitions

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, and sec-butyl groups.

As used herein, the term "cycloalkyl" means a cyclic saturated hydrocarbon group. Examples of cycloalkyl groups include cyclopropyl, cyclobutyl, cyclopentyl and cyclohexyl.

As used herein, the term "cycloalkylmethyl" means a cyclic saturated hydrocarbon group linked to the rest of the molecule via a methylene bridge. Examples of cycloalkylmethyl groups include cyclopropylmethyl, cyclobutylmethyl, cyclopentylmethyl and cyclohexylmethyl.

As used herein, the term "halogen" or "halo" means fluorine, chlorine, bromine or iodine. Fluorine, chlorine and bromine are particularly preferred.

"Pharmaceutically acceptable salt" means a salt such as those described in standard texts on salt formation, see for example: P. Stahl, et al. Handbook of Pharmaceutical Salts: Properties, Selection and Use (VCHA/Wiley-VCH, 2002), or S. M. Berge, et at, "Pharmaceutical Salts" (1977) *Journal of Pharmaceutical Sciences,* 66, 1-19. Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as $C_1$-$C_4$ alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids, which may or may not in themselves be pharmaceutically acceptable, may be useful as intermediates in obtaining the compounds of the invention and their pharmaceutical acceptable acid addition salts.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

"Pharmaceutically acceptable solvate" means a molecular complex comprising the compound of the invention and one or more pharmaceutically acceptable solvent molecules, for example, water or ethanol. Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al. *Pharmaceutical Research,* 1995. 12(7): p. 954-954, and Water-Insoluble Drug Formulation, $2^{nd}$ ed. R. Liu, CRC Press, page 553, which are incorporated herein by reference.

"Therapy", "treatment" and "treating" include both preventative and curative treatment of a condition, disease or disorder. It also includes slowing, interrupting, controlling or stopping the progression of a condition, disease or disorder. It also includes preventing, curing, slowing, interrupting, controlling or stopping the symptoms of a condition, disease or disorder.

B. Compounds

The invention provides a compound of formula (1a), (1b), (1c) or (1d) as defined above, or a pharmaceutically acceptable salt or solvate thereof (1a)

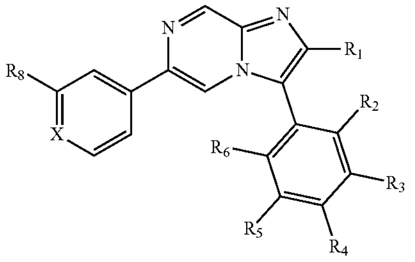

-continued (1b)

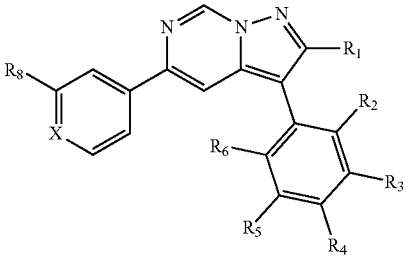

(1c)

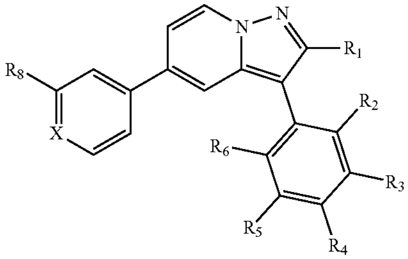

(1d)

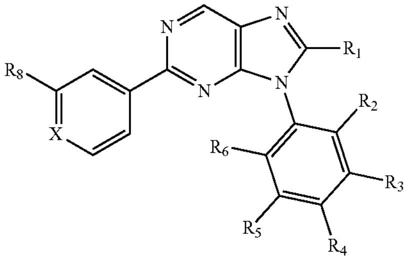

The invention also provides a compound of formula (1a') or (1b') or a pharmaceutically acceptable salt or solvate thereof, (1b')

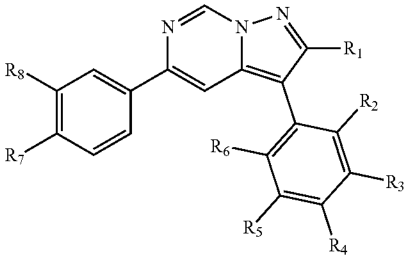

(1a')

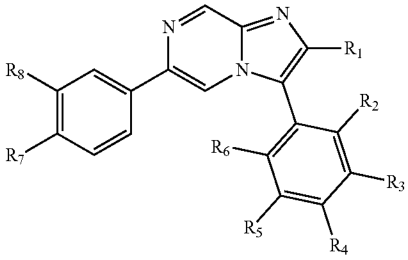

wherein:

$R_1$ is $C_1$-$C_4$ alkyl optionally substituted with up to five F atoms, $C_3$-$C_6$ cycloalkyl optionally substituted with one methyl group, or $C_4$-$C_7$ cycloalkylmethyl;

$R_2$ is H, F, Cl or OMe;

$R_3$ is H, OH, OMe, OPO(OH)OH or $OCH_2OPO(OH)OH$;
$R_4$ is H, OH, OMe, OPO(OH)OH or $OCH_2OPO(OH)OH$;
provided that $R_3$ and $R_4$ cannot both be H;
or $R_3$ and $R_4$ combine, together with the phenyl ring to which they are attached, to form an indazole group as shown below

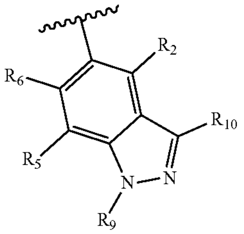
or
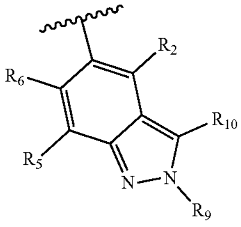

$R_5$ is H, F, Cl or OMe;
$R_6$ is H, F, Cl or OMe;
$R_7$ is H or F;
$R_8$ is $SF_5$ or $C_1$-$C_3$ alkyl substituted with three to seven F atoms;
$R_9$ is H; and
$R_{10}$ is H, F or Me.

B0. Core Structures

In some embodiments the compound of the invention is of formula (1a), as defined above.

In other embodiments the compound of the invention is of formula (1b), as defined above.

In other embodiments the compound of the invention is of formula (1c), as defined above.

In other embodiments the compound of the invention is of formula (1d), as defined above.

In other embodiments the compound of the invention is of formula (1a'), as defined above.

In other embodiments the compound of the invention is of formula (1b'), as defined above.

B1. Substituent $R_1$ $R_1$ is selected from the group consisting of $C_1$-$C_4$ alkyl optionally substituted with up to five F atoms, $C_3$-$C_6$ cycloalkyl optionally substituted with one methyl group, and $C_4$-$C_7$ cycloalkylmethyl.

$R_1$ is preferably selected from the group consisting of methyl, ethyl, n-propyl, isopropyl, cyclopropyl optionally substituted with one methyl group, cyclobutyl, cyclopropylmethyl, $CHF_2$, $CF_3$ and $CH_2CF_3$.

$R_1$ is more preferably selected from the group consisting of ethyl, isopropyl, cyclopropyl, cyclobutyl, $CF_3$ and $CH_2CF_3$.

B2. Substituent $R_2$ $R_2$ is selected from the group consisting of H, F, Cl and OMe.

$R_2$ is preferably selected from the group consisting of H, F and Cl.

$R_2$ is more preferably F or Cl.

$R_2$ is most preferably F

B3. Substituent $R_3$ $R_3$ is selected from the group consisting of H, OH, OMe, OPO(OH)OH and $OCH_2OPO(OH)OH$.

$R_3$ is preferably selected from the group consisting of H, OH, OMe and OPO(OH)OH.

$R_3$ is more preferably H.

B4. Substituent $R_4$ $R_4$ is selected from the group consisting of H, OH, OMe, OPO(OH)OH and $OCH_2OPO(OH)OH$.

$R_4$ is preferably selected from the group consisting of H, OH, OMe and OPO(OH)OH.

$R_4$ is more preferably OH.

Alternatively, and preferably, substituents $R_3$ and $R_4$ may combine, together with the phenyl ring to which they are attached, to form an indazole group as shown below

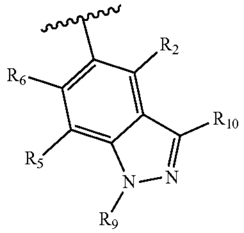
or
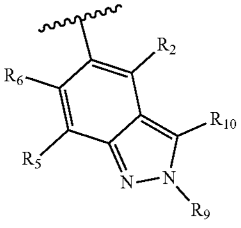

wherein:
$R_9$ is H; and
$R_{10}$ is selected from the group consisting of H, F and Me.

In a preferred embodiment of the indazole, $R_{10}$ is selected from the group consisting of H and Me In a more preferred embodiment of the indazole, substituents $R_9$ and $R_{10}$ are both H.

B5. Substituent $R_5$ $R_5$ is selected from the group consisting of H, F, Cl and OMe.

$R_5$ is preferably selected from the group consisting of H and OMe.

$R_5$ is more preferably H.

B6. Substituent $R_6$ $R_6$ is selected from the group consisting of H, F, Cl and OMe.

$R_6$ is preferably selected from the group consisting of H and F.

B7. Substituent X

X is N or C—$R_7$, where $R_7$ is selected from the group consisting of H and F.

In one embodiment, X is C—$R_7$.

B8. Substituent $R_8$ $R_8$ is selected from the group consisting of $SF_5$, Br, $C_1$-$C_3$ alkyl optionally substituted with up to to seven F atoms; $C_3$-$C_4$ cycloalkyl; $OCH_2C{\equiv}CH$ and $OC_1$-$C_3$ alkyl optionally substituted with up to to seven F atoms.

Alternatively, $R_8$ is selected from the group consisting of $SF_5$ and $C_1$-$C_3$ alkyl substituted with three to seven F atoms.

$R_8$ is preferably selected from the group consisting of cyclopropyl, cyclobutyl, isopropyl, $CH_2CF_3$, $OCF_3$, $O^iPr$, $CF_3$, $CF_2CF_3$ and $SF_5$.

Alternatively, $R_8$ is preferably selected from the group consisting of $CF_3$, $CF_2CF_3$ and $SF_5$.

B9. Combinations of Substituents $R_2$ to $R_6$

Preferred combinations of substituents $R_2$ to-$R_6$ include:

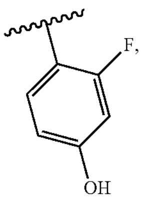
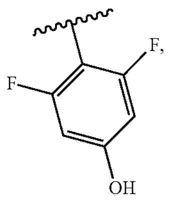

-continued

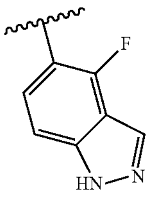

and

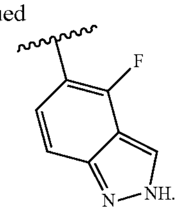

B10. Combinations of Substituents X and $R_8$

Preferred combinations of substituents X and $R_8$ include:

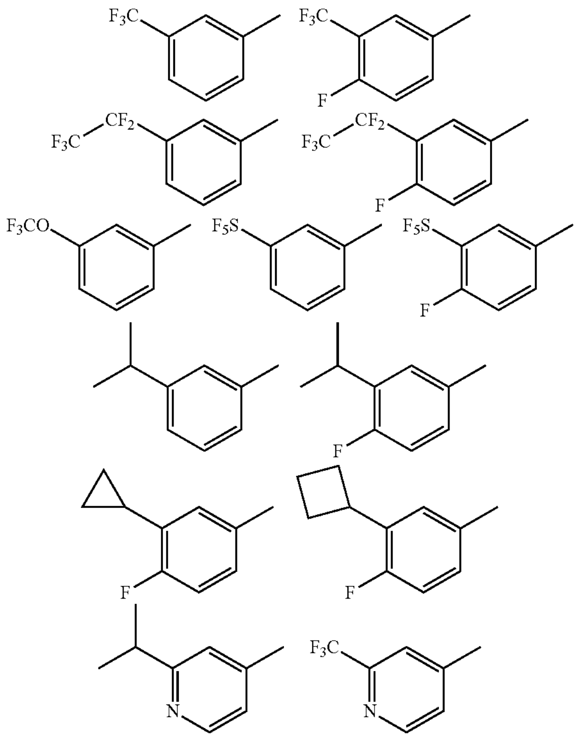

Alternative preferred combinations of substituents X and $R_8$ include:

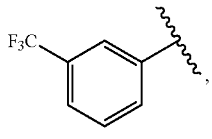

,

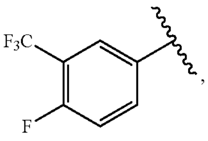

,

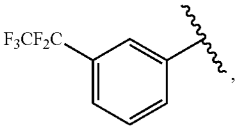

,

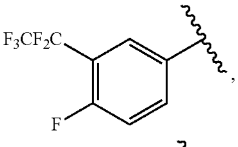

,

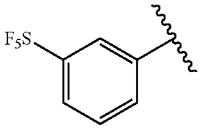

and

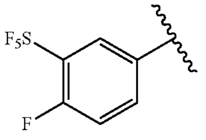

B11. Specific Embodiments of Compounds of Formula (1a), (1b), (1c) and (1d)

Various embodiments of substituents $R_1$, $R_2$, $R_3$, $R_4$, $R_5$, $R_6$, X, $R_7$, $R_8$, $R_9$ and $R_{10}$ have been discussed in B1 to B10 above. These “substituent” embodiments can be combined with any of the “core structure” embodiments, discussed in BO above, to form further embodiments of compounds of formula (1a), (1a'), (1b), (1b'), (1c) and (1d). All embodiments of compounds of formula (1a), (1a'), (1b), (1b'), (1c) and (1d) formed by combining the “substituent” embodiments and “core structure” embodiments, discussed above, are within the scope of the present invention, and some further preferred embodiments of the compounds of formula (1a), (1a'), (1b), (1b'), (1c) and (1d) are provided below.

In a preferred aspect of the first embodiment, the invention provides a compound of formula (1a), (1a'), (1b), (1b'), (1c) or (1d) or a pharmaceutically acceptable salt or solvate thereof, wherein:

$R_1$ is methyl, ethyl, n-propyl, isopropyl, cyclopropyl optionally substituted with one methyl group, cyclobutyl, cyclopropylmethyl, $CHF_2$, $CF_3$ or $CH_2CF_3$;

$R_2$ is H, F or OMe; or $R_2$ is H, F or Cl;

$R_3$ is H, OH, OMe or OPO(OH)OH;

$R_4$ is H, OH, OMe or OPO(OH)OH;

provided that $R_3$ and $R_4$ cannot both be H;

or $R_3$ and $R_4$ combine, together with the phenyl ring to which they are attached, to form an indazole group as shown below;

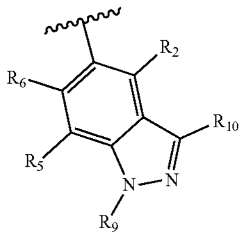

or

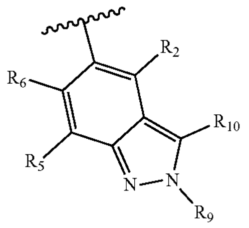

$R_5$ is H or OMe;

$R_6$ is H or F;

X is N or C—$R_7$ where $R_7$ is H or F; or X is C—$R_7$ where $R_7$ is H or F;

$R_8$ is $CF_3$, $CF_2CF_3$, $CH_2CF_3$, $CH(CH_3)_2$, $OCF_3$, $OCH(CH_3)_2$, cyclopropyl, cycolbutyl or $SF_5$; or $R_8$ is $CF_3$, $CF_2CF_3$ or $SF_5$;

$R_9$ is H; and $R_{10}$ is H.

In a more preferred aspect of the first embodiment, the invention provides a compound of formula (1a), (1a'), (1b), (1b'), or (1c) or a pharmaceutically acceptable salt or solvate thereof, wherein:

$R_1$ is ethyl, isopropyl, cyclopropyl, cyclobutyl, $CF_3$ or $CH_2CF_3$; or $R_1$ is ethyl, isopropyl, cyclopropyl, $CF_3$ or $CH_2CF_3$;

$R_2$ is F;

$R_3$ is H;

$R_4$ is OH;

or $R_3$ and $R_4$ combine, together with the phenyl ring to which they are attached, to form an indazole group as shown below;

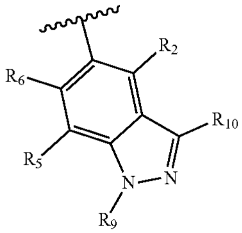

or

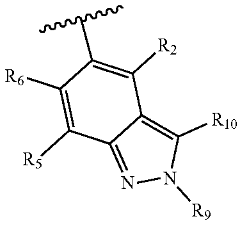

$R_5$ is H;
$R_6$ is H or F;
X is C—$R_7$ where $R_7$ is H or F;
$R_8$ is $CF_3$, $CF_2CF_3$ $CH(CH_3)_2$ or $SF_5$; or $R_8$ is $CF_3$, $CF_2CF_3$ or $SF_5$;
$R_9$ is H; and
$R_{10}$ is H.

In an even more preferred aspect of the first embodiment, the invention provides a compound of formula (1a), (1a'), (1 b), (1 b'), (1c) or (1 d) or a pharmaceutically acceptable salt or solvate thereof,
wherein:
$R_1$ is ethyl, isopropyl, cyclopropyl, $CF_3$ or $CH_2CF_3$;
$R_2$ to $R_6$ are selected to provide the structure:

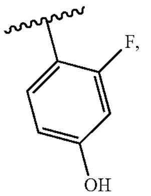

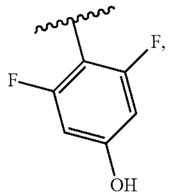

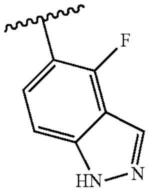

or

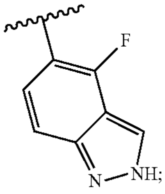

and
$R_7$ and $R_8$ are selected to provide the structure

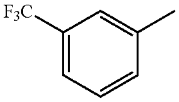

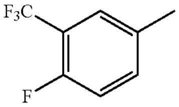

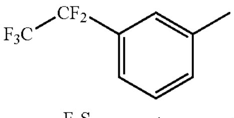

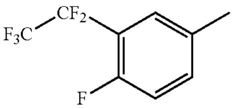

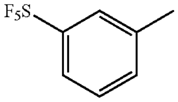

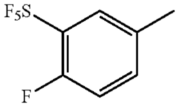

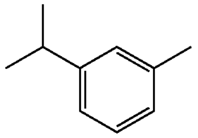

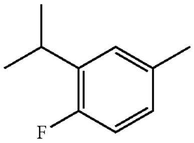

or $R_7$ and $R_8$ are selected to provide the structure:

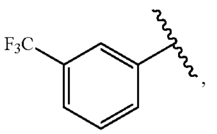

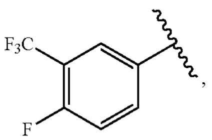

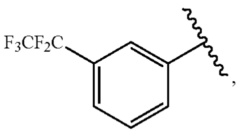

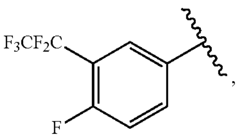

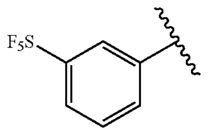

or

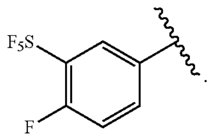

The following compounds represent specific embodiments of the invention:

Example 1: 2-methoxy-5-[2-(propan-2-yl)-6-[3-(trifluoromethyl)phenyl]imidazo[1,2-a]pyrazin-3-yl]phenol Example 2: 4-fluoro-5-{6-[4-fluoro-3-(trifluoromethyl)phenyl]-2-(propan-2-yl)imidazo[1,2-a]pyrazin-3-yl}-1H-indazole Example 3: 3-fluoro-4-[2-(propan-2-yl)-6-[3-(trifluoromethyl)phenyl]imidazo[1,2-a]pyrazin-3-yl]phenoxyphosphonic acid Example 4: 4-[2-methyl-6-[3-(trifluoromethyl)phenyl]imidazo[1,2-a]pyrazin-3-yl]phenol Example 5: 2-methoxy-4-(2-methyl-6-(3-(trifluoromethyl)phenyl)imidazo[1,2-a]pyrazin-3-yl)

Example 6: 3-fluoro-4-[2-methyl-6-[3-(trifluoromethyl)phenyl]imidazo[1,2-a]pyrazin-3-yl]phenol Example 7: 2-methoxy-5-[2-ethyl-6-[3-(trifluoromethyl)phenyl]imidazo[1,2-a]pyrazin-3-yl]phenol Example 8: 3-fluoro-4-[2-ethyl-6-[3-(trifluoromethyl)phenyl]imidazo[1,2-a]pyrazin-3-yl]phenol Example 9: 3-fluoro-4-[2-(propan-2-yl)-6-[3-(trifluoromethyl)phenyl]imidazo[1,2-a]pyrazin-3-yl]phenol Example 10: 3-fluoro-4-[2-methyl-6-[4-fluoro-3-(trifluoromethyl)phenyl]imidazo[1,2-a]pyrazin-3-yl]phenol Example 11: 3-fluoro-4-[2-difluoromethyl-6-[3-(trifluoromethyl)phenyl]imidazo[1,2-a]pyrazin-3-yl]phenol Example 12: 3-fluoro-4-[2-trifluoromethyl-6-[3-(trifluoromethyl)phenyl]imidazo[1,2-a]pyrazin-3-yl]phenol Example 13: 2-methoxy-5-[2-cyclopropyl-6-[3-(trifluoromethyl)phenyl]imidazo[1,2-a]pyrazin-3-yl]phenol Example 14: 3-fluoro-4-[2-cyclopropyl-6-[3-(trifluoromethyl)phenyl]imidazo[1,2-a]pyrazin-3-yl]phenol Example 15: 3,5-difluoro-4-[2-methyl-6-[3-(trifluoromethyl)phenyl]imidazo[1,2-a]pyrazin-3-yl]phenol Example 16: 3,5-difluoro-4-[2-methyl-6-[4-fluoro-3-(trifluoromethyl)phenyl]imidazo[1,2-a]pyrazin-3-yl]phenol Example 17: 3,5-difluoro-4-[2-(propan-2-yl)-6-[4-fluoro-3-(trifluoromethyl) phenyl]imidazo[1,2-a]pyrazin-3-yl]phenol Example 18: 2-methoxy-5-[2-(propan-1-yl)-6-[3-(trifluoromethyl)phenyl]imidazo[1,2-a]pyrazin-3-yl]phenol Example 19: 3,5-difluoro-4-[2-(propan-2-yl)-6-[3-(trifluoromethyl)phenyl]imidazo[1,2-a]pyrazin-3-yl]phenol Example 20: 4-(2-isopropyl-6-(3-(trifluoromethyl)phenyl)imidazo[1,2-a]pyrazin-3-yl)-3-methoxyphenol Example 21: 4-fluoro-5-{2-propan-2-yl-6-[3-trifluoromethylphenyl]imidazo[1,2-a]pyrazin-3-yl}-1H-indazole Example 22: 7-methoxy-5-{2-(propan-2-yl)-6-[3-trifluoromethylphenyl]imidazo[1,2-a]pyrazin-3-yl}-1H-indazole Example 23: 2-methoxy-5-(2-methyl-5-(3-(trifluoromethyl)phenyl)pyrazolo[1,5-c]pyrimidin-3-yl)phenol Example 24: 3,5-difluoro-4-(2-isopropyl-5-(3-(trifluoromethyl)phenyl)pyrazolo[1,5-c]pyrimidin-3-yl)phenol Example 25: 5-(2-isopropyl-5-(3-(trifluoromethyl)phenyl)pyrazolo[1,5-c]pyrimidin-3-yl)-2-methoxyphenol Example 26: 2-methoxy-5-[2-(cyclopropylmethyl)-6-[3-(trifluoromethyl)phenyl]imidazo[1,2-a]pyrazin-3-yl]phenol Example 27: 2-methoxy-5-[2-(propan-2-yl)-6-[4-fluoro-3-(trifluoromethyl)phenyl]imidazo[1,2-a]pyrazin-3-yl]phenol Example 28: 2-methoxy-5-[2-(propan-2-yl)-6-[3-(trifluoromethyl)phenyl]imidazo[1,2-a]pyrazin-3-yl]phenoxyphosphonic acid Example 29: 4-fluoro-5-{2-trifluoromethyl-6-[3-(pentafluoroethyl)phenyl]imidazo[1,2-a]pyrazin-3-yl}-1H-indazole Example 30: 2-methoxy-5-[2-(trifluoromethyl)-6-[3-(pentafluoroethyl)phenyl]imidazo[1,2-a]pyrazin-3-yl]phenol Example 31: 3,5-difluoro-4-[2-methyl-6-[3-(pentafluorosulfanyl)phenyl]imidazo[1,2-a]pyrazin-3-yl]phenol Example 32: 4-fluoro-5-(2-cyclopropyl-6-(4-fluoro-3-(trifluoromethyl)phenyl)-3-(1H-indazol-4-yl)imidazo[1,2-a]pyrazine Example 33: 3,5-difluoro-4-[2-(1-methyl-cycloprop-1-yl)-6-[4-fluoro-3-(trifluoromethyl)phenyl]imidazo[1,2-a]pyrazin-3-yl]phenol Example 34: 4-(2-cyclopropyl-6-(4-fluoro-3-(trifluoromethyl)phenyl)imidazo[1,2-a]pyrazin-3-yl)-3,5-difluorophenol Example 35: 4-(2-cyclobutyl-6-(4-fluoro-3-(trifluoromethyl)phenyl)imidazo[1,2-a]pyrazin-3-yl)-3,5-difluorophenol Example 36: 3,5-difluoro-4-[2-ethyl-6-[4-fluoro-3-(trifluoromethyl)phenyl]imidazo[1,2-a]pyrazin-3-yl]phenol Example 37: 4-fluoro-5-{2-ethyl-6-[4-fluoro-3-(trifluoromethyl)phenyl]imidazo[1,2-a]pyrazin-3-yl}-1H-indazole Example 38: 3,5-difluoro-4-(6-(4-fluoro-3-(trifluoromethyl)phenyl)-2-(2,2,2-trifluoroethyl)imidazo[1,2-a]pyrazin-3-yl)phenol Example 39: 3,5-difluoro-4-[2-(propan-2-yl)-6-[3-(pentafluorosulfanyl)phenyl]imidazo[1,2-a]pyrazin-3-yl]phenol Example 40: 3,5-difluoro-4-{6-[4-fluoro-3-(trifluoromethyl)phenyl]-2-(propan-2-yl)imidazo[1,2-a]pyrazin-3-yl}phenoxyphosphonic acid Example 41: 3,5-difluoro-4-{6-[4-fluoro-3-(trifluoromethyl)phenyl]-2-methyl-imidazo[1,2-a]pyrazin-3-yl}phenoxyphosphonic acid Example 42: 3,5-difluoro-4-(5-(4-fluoro-3-(trifluoromethyl)phenyl)-2-methylpyrazolo[1,5-c]pyrimidin-3-yl)phenol Example 43: 2-cyclopropyl-3-(4-fluoro-1H-indazol-5-yl)-6-(4-fluoro-3-(trifluoromethyl)phenyl)imidazo[1,2-a]pyrazine Example 44: 4-[2-Cyclopropyl-6-(4-fluoro-3-pentafluoroethyl-phenyl)-imidazo[1,2-a]pyrazin-3-yl]-3,5-difluorophenol Example 45: 4-{2-ethyl-6-[4-fluoro-3-(1,1,2,2,2-pentafluoroethyl)phenyl]imidazo[1,2-a]pyrazin-3-yl}-3,5-difluorophenol Example 46: 2-cyclopropyl-3-(4-fluoro-1H-indazol-5-yl)-6-(3-(pentafluoro-λ6-sulfaneyl)phenyl)imidazo[1,2-a]pyrazine Example 47: 3,5-difluoro-4-(5-(4-fluoro-3-(trifluoromethyl)phenyl)-2-isopropylpyrazolo[1,5-c]pyrimidin-3-yl)phenol Example 48: 4-(2-ethyl-5-(4-fluoro-3-(trifluoromethyl)phenyl)pyrazolo[1,5-c]pyrimidin-3-yl)-3,5-difluorophenol Example 49: 3,5-difluoro-4-[2-methyl-6-[3-(pentafluoroethyl)phenyl]imidazo[1,2-a]pyrazin-3-yl]phenol Example 50: 3-(4-Fluoro-1H-indazol-5-yl)-6-(4-fluoro-3-trifluoromethyl phenyl)-2-trifluoromethyl-imidazo[1,2-a]pyrazine Example 51: 2-Isopropyl-3-(3-methyl-1H-indazol-5-yl)-6-(3-trifluoromethyl-phenyl)-imidazo[1,2-a]pyrazine Example 52: 4-[2-Ethyl-6-(3-pentafluoroethyl-phenyl)-imidazo[1,2-a]pyrazin-3-yl]-3,5-difluoro-phenol Example 53: 3,5-Difluoro-4-[6-(4-fluoro-3-pentafluoroethyl-phenyl)-2-methyl-imidazo[1,2-a]pyrazin-3-yl]-phenol Example 54: 5-{2-cyclopropyl-6-[4-fluoro-3-(1,1,2,2,2-pentafluoroethyl)phenyl]imidazo[1,2-a]pyrazin-3-yl}-4-fluoro-1H-indazole Example 55: 4-Fluoro-5-[5-(4-fluoro-3-trifluoro methyl-phenyl)-2-isopropylpyrazolo[1,5-a]pyridin-3-yl]-1H-indazole Example 56: 4-[2-Cyclopropyl-6-(4-fluoro-3-pentafluorosulfanyl-phenyl)-imidazo[1,2-a]pyrazin-3-yl]-3,5-difluoro-phenol Example 57: 2-Cyclopropyl-3-(4-fluoro-1H-indazol-5-yl)-6-(4-fluoro-3-pentafluorosulfanyl-phenyl)-imidazo[1,2-a]pyrazine Example 58: 3-(4-Fluoro-1H-indazol-5-yl)-5-(4-fluoro-3-pentafluoroethyl-phenyl)-2-isopropylpyrazolo[1,5-c]pyrimidine Example 59: 2-Cyclopropyl-3-(4-fluoro-1H-indazol-5-yl)-5-(4-fluoro-3-pentafluoroethyl-phenyl)-pyrazolo[1,5-c]pyrimidine Example 60: 4-[2-Cyclopropyl-5-(4-fluoro-3-trifluoromethyl-phenyl)-pyrazolo[1,5-c]pyrimidin-3-yl]-3,5-difluoro-phenol Example 61: 3-(4-Fluoro-1H-indazol-5-yl)-5-(4-fluoro-3-trifluoromethyl-phenyl)-2-isopropylpyrazolo[1,5-c]pyrimidine Example 62: Phosphoric acid mono-{4-[2-cyclopropyl-6-(4-fluoro-3-trifluoromethyl-phenyl)-imidazo[1,2-a]pyrazin-3-yl]-3,5-difluoro-phenyl}ester Example 63: 3-(4-Fluoro-1H-indazol-5-yl)-6-(4-fluoro-3-pentafluoroethyl-phenyl)-2-trifluoromethyl-imidazo[1,2-a]pyrazine Example 64: 3-(4-Fluoro-1H-indazol-5-yl)-6-(4-fluoro-3-pentafluorosulfanyl-phenyl)-2-methyl-imidazo[1,2-a]pyrazine Example 65: 3-(4-Fluoro-1H-indazol-5-yl)-6-(4-fluoro-3-pentafluorosulfanyl-phenyl)-2-trifluoromethyl-imidazo[1,2-a]pyrazine Example 66: 3-(4-Fluoro-1H-indazol-5-yl)-6-(3-isopropyl-phenyl)-2-trifluoromethyl-imidazo[1,2-a]pyrazine Example 67: 3-(4-Fluoro-1H-indazol-5-yl)-6-(4-fluoro-3-isopropyl-phenyl)-2-trifluoromethyl-imidazo[1,2-a]pyrazine Example 68: 3-(4-Fluoro-1H-indazol-5-yl)-6-(4-fluoro-3-pentafluorosulfanyl-phenyl)-2-isopropyl-imidazo[1,2-a]pyrazine Example 69: 3-(4-Fluoro-1H-indazol-5-yl)-6-[4-fluoro-3-(2,2,2-trifluoro-ethyl)-phenyl]-2-trifluoromethyl-imidazo[1,2-a]pyrazine Example 70: 3-(4-Fluoro-1H-indazol-5-yl)-2-trifluoromethyl-6-(3-trifluoromethyl-phenyl)-imidazo[1,2-a]pyrazine Example 71: 3-(4-Fluoro-1H-indazol-5-yl)-6-(4-fluoro-3-trifluoromethoxy-phenyl)-2-trifluoromethyl-imidazo[1,2-a]pyrazine Example 72: 3-(4-Fluoro-1H-indazol-5-yl)-6-(3-trifluoromethoxy-phenyl)-2-trifluoromethyl-imidazo[1,2-a]pyrazine Example 73: 6-(3-Bromo-phenyl)-3-(4-fluoro-1H-indazol-5-yl)-2-isopropyl-imidazo[1,2-a]pyrazine Example 74: 3-(4-Fluoro-1H-indazol-5-yl)-6-(4-fluoro-3-isopropyl-phenyl)-2-isopropyl-imidazo[1,2-a]pyrazine Example 75: 2-Ethyl-3-(4-fluoro-1H-indazol-5-yl)-6-(4-fluoro-3-isopropyl-phenyl)-imidazo[1,2-a]pyrazine Example 76: 2-Cyclobutyl-3-(4-fluoro-1H-indazol-5-yl)-6-(4-fluoro-3-trifluoromethyl-phenyl)-imidazo[1,2-a]pyrazine Example 77: 2-Cyclobutyl-3-(4-fluoro-1H-indazol-5-yl)-6-(4-fluoro-3-isopropyl-phenyl)-imidazo[1,2-a]pyrazine Example 78: 3-(4-Fluoro-1H-indazol-5-yl)-6-(4-fluoro-3-prop-2-ynyloxy-phenyl)-2-trifluoromethyl-imidazo[1,2-a]pyrazine Example 79: 2-Cyclopropyl-3-(4-fluoro-1H-indazol-5-yl)-6-(4-fluoro-3-isopropyl-phenyl)-imidazo[1,2-a]pyrazine Example 80: 4-[2-Cyclopropyl-6-(4-fluoro-3-isopropyl-phenyl)-imidazo[1,2-a]pyrazin-3-yl]-3,5-difluoro-phenol Example 81: 3-(4-Fluoro-1H-indazol-5-yl)-6-(4-fluoro-3-isopropoxy-phenyl)-2-trifluoromethyl-imidazo[1,2-a]pyrazine Example 82: 6-(3-Cyclobutyl-4-fluoro-phenyl)-3-(4-fluoro-1H-indazol-5-yl)-2-trifluoromethyl-imidazo[1,2-a]pyrazine Example 83: 3-(4-Chloro-1H-indazol-5-yl)-6-(4-fluoro-3-isopropyl-phenyl)-2-trifluoromethyl-imidazo[1,2-a]pyrazine Example 84: 6-(3-Cyclopropyl-4-fluoro-phenyl)-3-(4-fluoro-1H-indazol-5-yl)-2-trifluoromethyl-imidazo[1,2-a]pyrazine Example 85: 6-(3-Bromo-4-fluoro-phenyl)-3-(4-fluoro-1H-indazol-5-yl)-2-trifluoromethyl-imidazo[1,2-a]pyrazine Example 86: 3-(4-Fluoro-1H-indazol-5-yl)-6-(3-isopropoxy-phenyl)-2-trifluoromethyl-imidazo[1,2-a]pyrazine Example 87: 3-(4-Fluoro-1H-indazol-5-yl)-6-(2-isopropyl-pyridin-4-yl)-2-trifluoromethyl-imidazo[1,2-a]pyrazine Example 88: 3-(4-Fluoro-1H-indazol-5-yl)-2-trifluoromethyl-6-(2-trifluoromethyl-pyridin-4-yl)-imidazo[1,2-a]pyrazine Example 89: 3,5-Difluoro-4-[2-(4-fluoro-3-trifluoromethyl-phenyl)-8-isopropyl-purin-9-yl]-phenol Example 90: 3-fluoro-4-[8-(propan-2-yl)-2-[3-(trifluoromethyl)phenyl]-9H-purin-9-yl]phenol

C. Compositions

The compounds of the invention intended for pharmaceutical use may be administered alone or in combination with one or more other compounds of the invention or in combination with one or more other drugs (or as any combination thereof). Generally, they will be administered as a formulation in association with one or more pharmaceutically acceptable excipients. Accordingly, the present invention is also directed to a pharmaceutical composition comprising (i) a therapeutically effective amount of a compound of formula (1a), (1b), (1c) or (1d) as defined above, or a pharmaceutically acceptable salt or solvate thereof; and (ii) a pharmaceutically acceptable excipient.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

D. Methods of Use

This invention is also directed to compounds of formula (1a), (1b), (1c) and (1d) as defined above, or a pharmaceutically acceptable salt or solvate thereof, for use in therapy, in particular for the treatment of schistosomiasis.

This invention is also directed to the use of compounds of formula (1a), (1b), (1c) and (1d), as defined above, or a pharmaceutically acceptable salt or solvate thereof, in the manufacture of a medicament for treatment of schistosomiasis.

This invention is also directed to a method for treating schistosomiasis comprising administering a therapeutically effective amount of a compound of formula (1a), (1b), (1c) or (1d) as defined above, or a pharmaceutically acceptable salt or solvate thereof, to a patient in need thereof.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

E. General Synthetic Methodology

The methods used for the synthesis of the compounds of the invention are illustrated by the schemes below. The starting materials and reagents used in preparing these compounds are available from commercial suppliers or can be prepared by methods obvious to those skilled in the art.

General Method 1A

The invention also provides a process for the preparation of *Schistosoma* growth inhibitors where $R_1$-$R_6$ and X are defined according to the invention and $R_8$ is $CF_3$, $CF_2CF_3$ or $CH(CH_3)_2$. The process involves reacting an appropriate 3-chloro or 3-bromo-imidazo[1,2-a]pyrazine with an appropriate arylboronic acid or aryl pinacol borane under Suzuki conditions in the presence of a palladium catalyst.

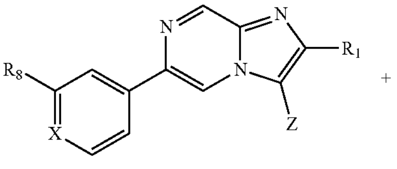

Z = Cl, Br

-continued

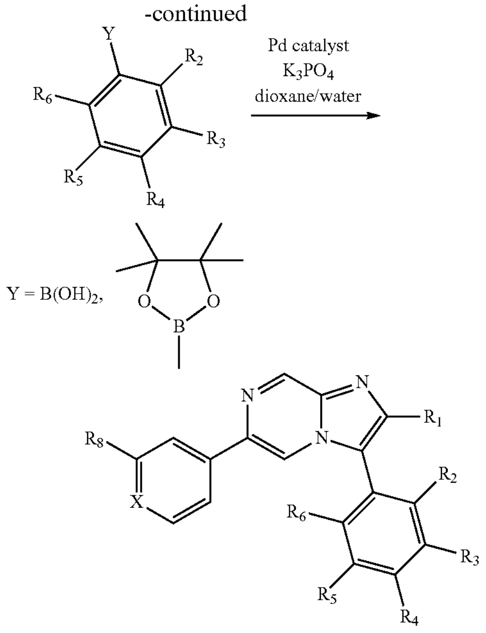

General Method 1B

The invention also provides a process for the preparation of *Schistosoma* growth inhibitors where $R_1$-$R_6$ and X are defined according to the invention and $R_8$ is $CF_3$ or $CF_2CF_3$. The process involves reacting an appropriate 3-bromo-pyrazolo[1,5-c]pyrimidine with an appropriate arylboronic acid or aryl pinacol borane under Suzuki conditions in the presence of a palladium catalyst.

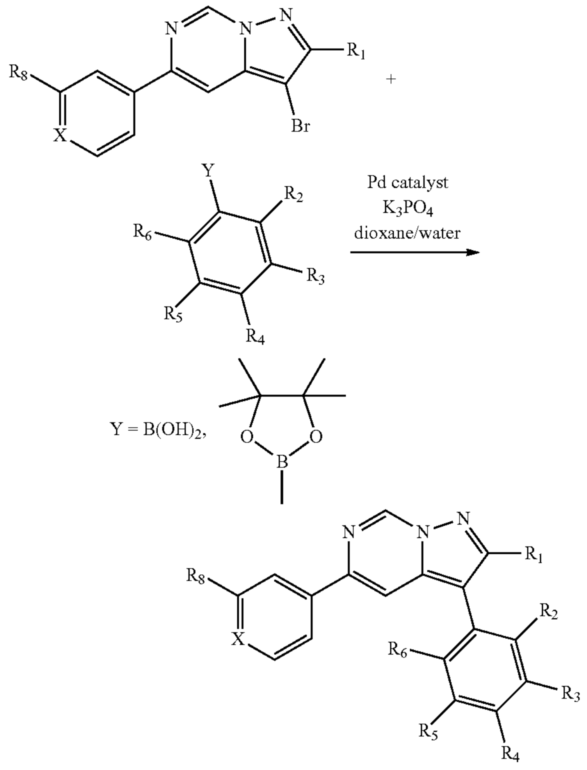

General Method 2

The invention also provides a process for the preparation of *Schistosoma* growth inhibitors where $R_1$-$R_6$ and X are defined according to the invention and $R_8$ is $CF_2CF_3$ or $SF_5$. The process involves reacting an appropriate 6-bromo-imidazo[1,2-a]pyrazine with an appropriate arylboronic acid or aryl pinacol borane under Suzuki conditions in the presence of a palladium catalyst.

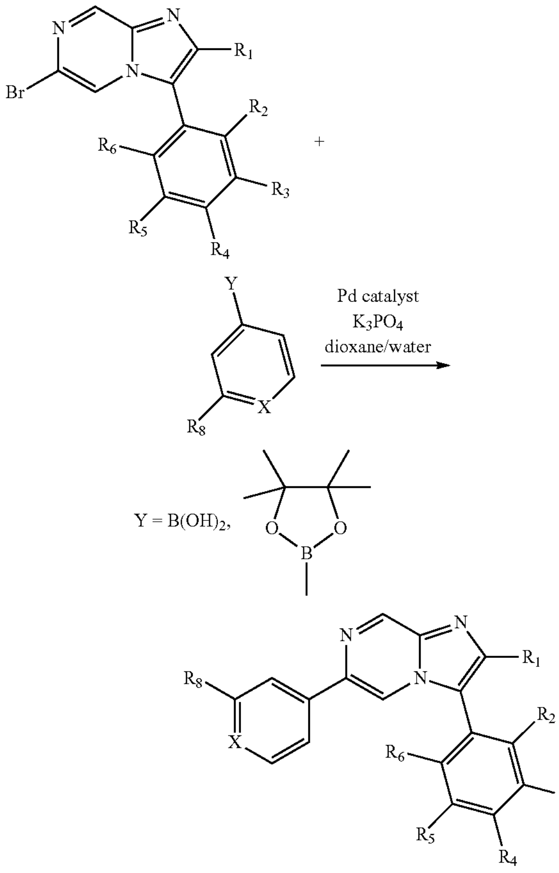

General Method 3A

The invention also provides a process for the preparation of *Schistosoma* growth inhibitors where $R_1$-$R_6$ and X are defined according to the invention and $R_8$ is $CF_3$, $CF_2CF_3$, $CH(CH_3)_2$, $CH_2CF_3$, $OCF_3$, $OCH(CH_3)_2$, $OCH_2C{\equiv}CH$, cPr, cBu or $SF_5$. The process involves reacting an appropriate 3-bromo or 3-chloro-imidazo[1,2-a]pyrazine with an appropriate THP-protected indazole pinacol borane under Suzuki conditions in the presence of a palladium catalyst. The THP group can be removed under acidic conditions e.g. with TFA or HCl in an alcoholic solvent.

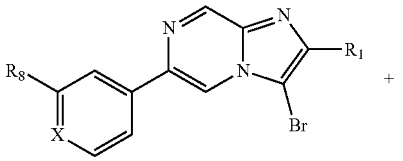

-continued

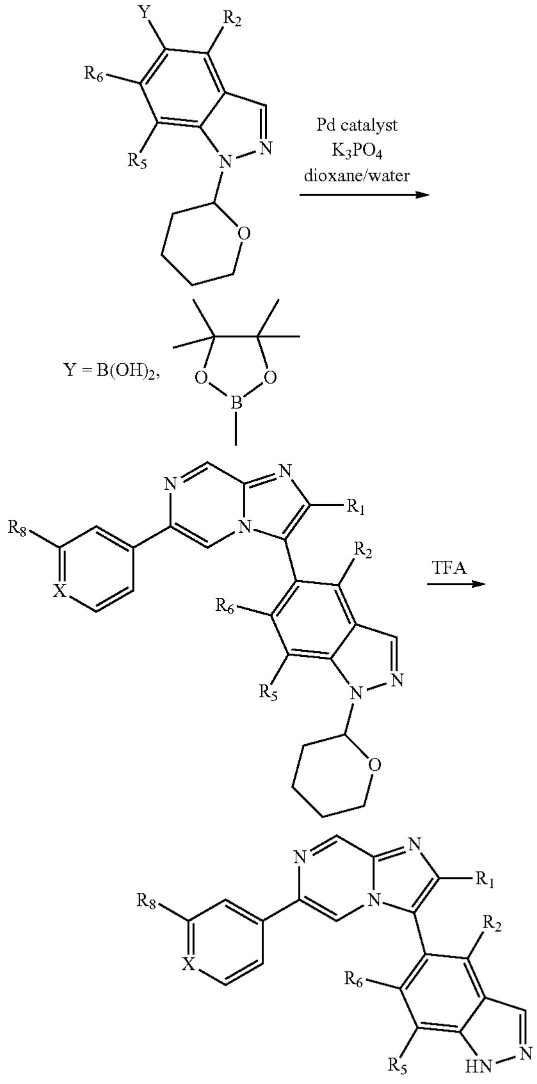

General Method 3B

The invention also provides a process for the preparation of *Schistosoma* growth inhibitors where $R_1$-$R_6$ and X are defined according to the invention and $R_8$ is $CF_3$ or $CF_2CF_3$. The process involves reacting an appropriate 3-bromo-pyrazolo[1,5-c]pyrimidine with an appropriate THP-protected indazole pinacol borane under Suzuki conditions in the presence of a palladium catalyst. The THP group can be removed under acidic conditions e.g. with TFA or HCl in an alcoholic solvent.

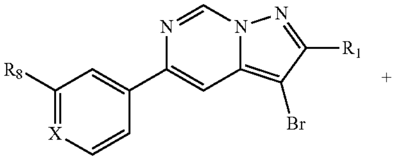

-continued

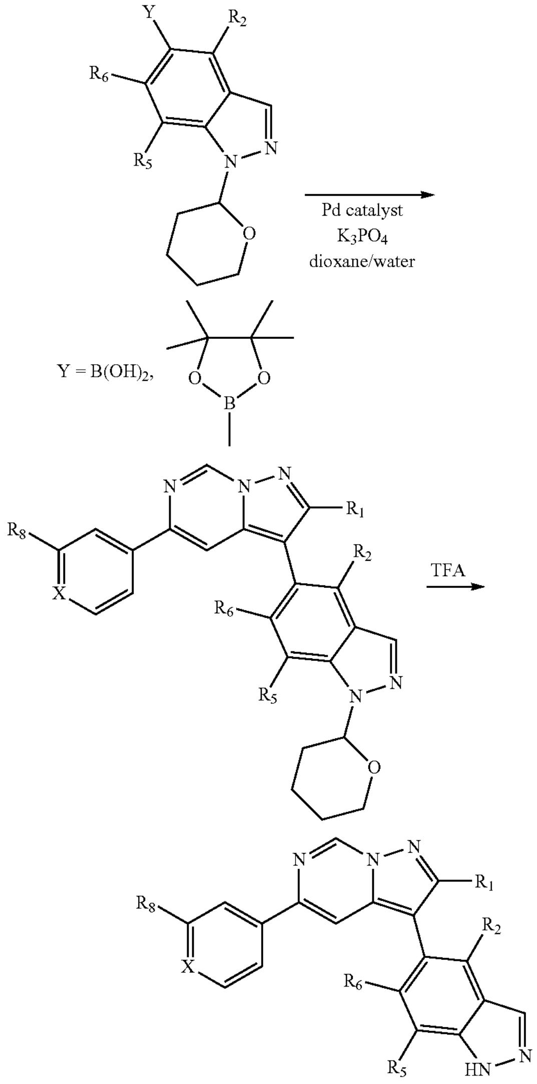

General Method 3C

The invention also provides a process for the preparation of *Schistosoma* growth inhibitors where $R_1$-$R_8$ and X are defined according to the invention. The process involves reacting an appropriate 3-bromo-pyrazolo[1,5-c]pyridine with an appropriate THP-protected indazole pinacol borane under Suzuki conditions in the presence of a palladium catalyst. The THP group can be removed under acidic conditions e.g. with TFA or HCl in an alcoholic solvent.

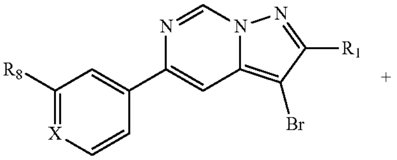

-continued

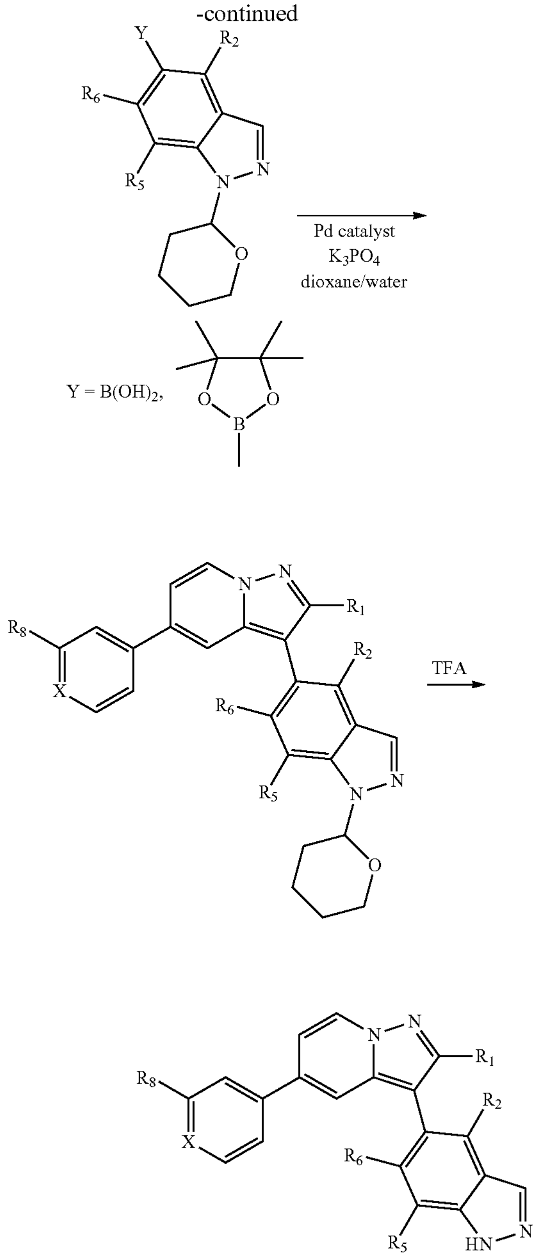

General Method 3D

The invention also provides a process for the preparation of *Schistosoma* growth inhibitors where $R_1$-$R_8$ and X are defined according to the invention. The process involves reacting an appropriate 3-iodo-imidazo[1,2-a]pyrazine with an appropriate THP-protected indazole pinacol borane under Suzuki conditions in the presence of a palladium catalyst. The THP group can be removed under acidic conditions e.g. with TFA or HCl in an alcoholic solvent.

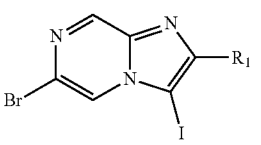

+

-continued

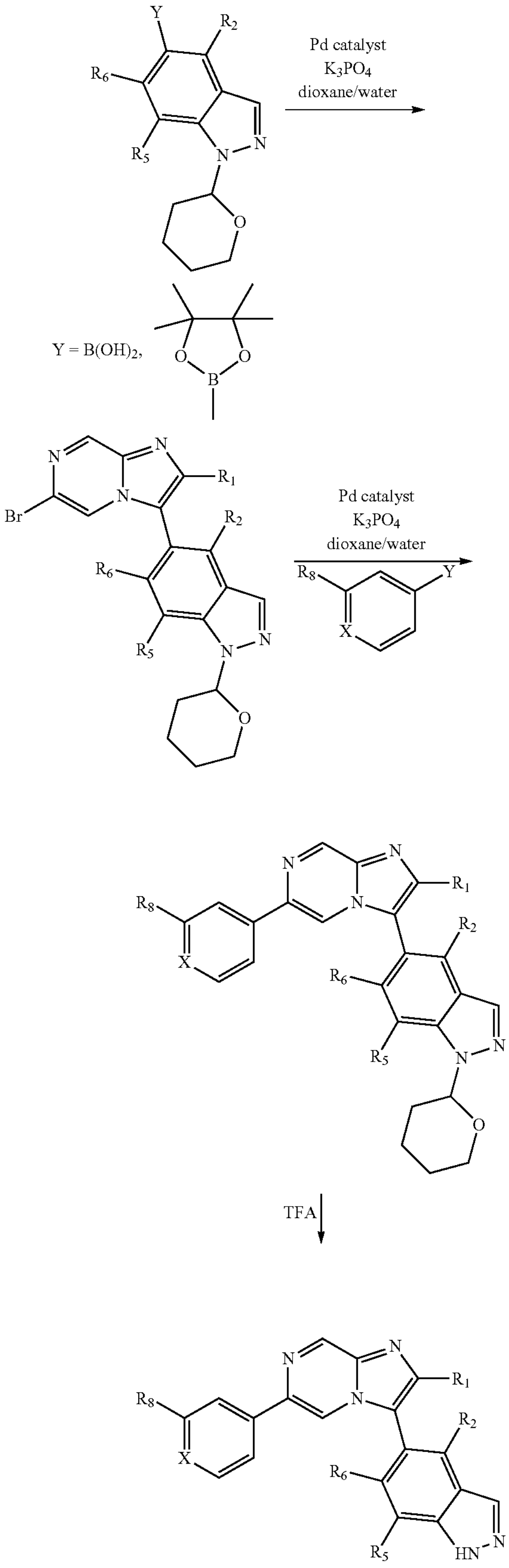

General Method 4

The invention also provides a process for the preparation of *Schistosoma* growth inhibitors where $R_1$, $R_2$ and $R_5$-$R_8$ and X are defined according to the invention, and $R_3$ or $R_4$ are OPO(OH)OH. The process involves reacting an appropriate hydroxyphenyl imidazo[1,2-a]pyrazine with phosphorus oxychloride in pyridine, followed by treatment of the crude product with acetone/water.

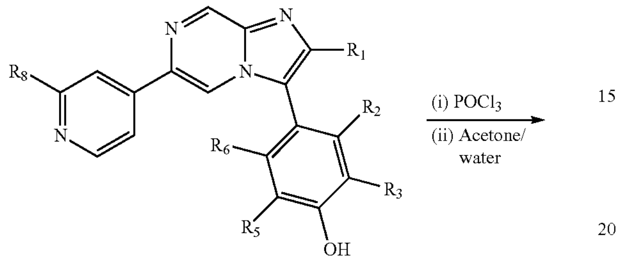

-continued

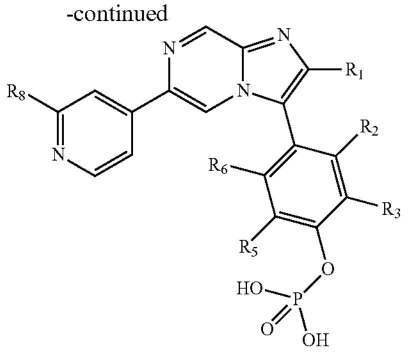

General Method 5

The invention also provides a process for the preparation of *Schistosoma* growth inhibitors where $R_1$, $R_2$, $R_6$, $R_8$ and X are defined according to the invention. The process involves coupling of an appropriate chloropyrimidine and arylboronic acid to give an intermediate, which is reduced with Raney Ni. The resulting diamine is reacted with an alkylaldehyde to provide an intermediate that is aromatised to a purine derivative and finally deprotected under acidic conditions.

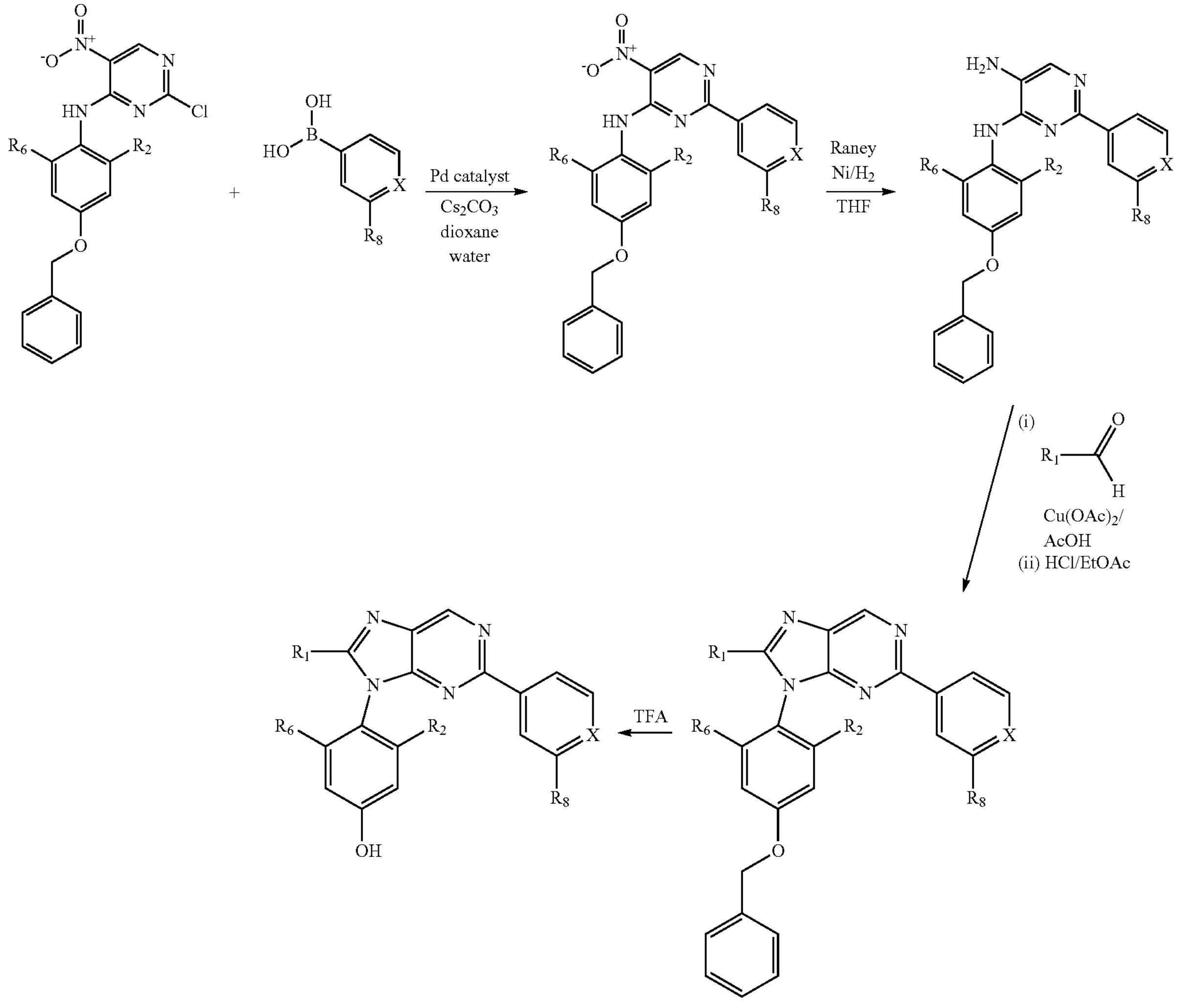

F. Synthesis of Example Compounds

General Experimental Details

LC-MS

Compounds requiring purification under basic conditions were purified on an LC-MS system equipped with a YMC Actus Triart C18 5 μm (20×250 mm) column or Gemini NX 5 μm C18 (100x30 mm) columns, using a gradient elution of acetonitrile in water containing 20 mM Ammonium bicarbonate (10-45% over 30 min then 95% acetonitrile for 2 minutes).

UPLC

Method A: Formic Acid/Ammonium acetate (3 min run-time-UPLC) (3 min) Column—Restek Ultra AQ C18 (30×2.1 mm, 3u), (mobile phase: 98% [0.05% modifier in water] and 2% [$CH_3CN$] held for 0.75 min, then to 90% [0.05% Modifier in water] and 10% [$CH_3CN$] in 1.0 min, further to 2% [0.05% Modifier in water] and 98% [$CH_3CN$] in 2.0 min, held this mobile phase composition up to 2.25 min and finally back to initial condition in 3.0 min).

Flow=1.5 ml/min

Method E: (General-5 min)

Column—ZorbaxC18 (50×4.6 mm, 5u, 130A), (mobile phase: from 90% [10 mM $NH_4OAc$ in water] and 10% [$CH_3CN$] to 70% [10 mM $NH_4OAc$ in water] and 30% [$CH_3CN$] in 1.5 min, further to 10% [10 mM $NH_4OAc$ in water] and 90% [$CH_3CN$] in 3.0 min, held this mobile phase composition up to 4.0 min and finally back to initial condition in 5.0 min). Flow=1.2 ml/min.

NMR $^1H$ NMR and $^{13}C$ spectra were recorded on 400 MHz and 101 MHz respectively instruments at room temperature unless specified otherwise were referenced to residual solvent signals. Data are presented as follows: chemical shift in ppm, integration, multiplicity (br=broad, app=apparent, s=singlet, d=doublet, t=triplet, q=quartet, p=pentet, m=multiplet) and coupling constants in Hz.

Preparation of Starting Materials

All of the starting materials for making the intermediates and example compounds were obtained from commercial sources or using literature methods with the exception of the following compounds.

Starting Material 1

4-fluoro-1-(oxan-2-yl)-5-(4,4,5,5-tetramethyl-1,3,2-dioxaborolan-2-yl)-1H-indazole To a stirred solution of 5-bromo-4-fluoro-1-(oxan-2-yl)-1H-indazole (800 mg, 2.7 mmol) in dioxane (20 mL) were added bis(pinacolato)diboron (1.36 g, 5.3 mmol) and potassium acetate (787 mg, 8.0 mmol) in sealed tube and the resulting mixture was stirred and degased by using argon gas for 5 min. After that Pd(dppf)$Cl_2$.DCM (218 mg, 0.27 mmol) was added and the resulting mixture was refluxed at 110° C. for 6 h. After completion, reaction mixture was evaporated under reduced pressure. The residue was suspended into water and extracted with ethyl acetate. Combined organic layer was dried over anhydrous $Na_2SO_4$ and evaporated under reduced pressure. The crude compound was purified by column chromatography using silica gel eluted with 0-10% EtOAc in hexane to give the title compound as a yellow color oil (900 mg, 97%). UPLC rt 1.9 min $MH^+$ 347. $^1H$ NMR (400 MHz, $CDCl_3$) δ 8.09 (s, 1H), 7.67 (dd, 1H), 7.31 (d, 1H), 5.69 (dd, 1H), 4.01 (d, 1H), 3.73 (t, 1H), 2.53 (m, 1H), 2.12 (m, 1H), 2.05 (m, 1H), 1.75 (m, 2H), 1.68 (m, 1H), 1.40 (s, 12H).

Starting Material 2

2-(4-Fluoro-3-pentafluoroethyl-phenyl)-4,4,5,5-tetramethyl-[1,3,2]dioxaborolane)

To a stirred solution of 4-Bromo-1-fluoro-2-pentafluoroethyl-benzene (1 g, 3.4 mmol) in 1,4-dioxane (25 ml) was added bispinacolatodiborane (1.7 g, 6.8 mmol) followed by potassium acetate (1 g, 10.2 mmol). The reaction mixture was deoxygenated with argon, then to the reaction mixture was added [1,1'-Bis(diphenylphosphino)ferrocene]palladium(II) chloride, complex with dichloromethane (0.28 g, 0.34 mmol) and the reaction mixture was allowed to stir at 90° C. for 16 hours under nitrogen. After complete consumption of the starting material (monitored by TLC) the reaction mixture was filtered throw a celite bed to remove the catalyst, the mother liquor was evaporated under reduced pressure, the residue was diluted with ethyl acetate, washed successively with water and brine, the organic layer dried over sodium sulphate and evaporated under reduced pressure to get the product, which was used without further purification.

Starting Material 3

4-Fluoro-1-(tetrahydro-pyran-2-yl)-5-(4,4,5,5-tetramethyl-[1,3,2]dioxaborolan-2-yl)-1H-indazole Step 1

4-Bromo-3-fluoro-2-methyl-phenylamine

To a stirred solution of 3-fluoro-2-methylaniline (15.0 g, 120 mmol) in ACN (300.0 mL) was added N-Bromosuccinimide (23 g, 132 mmol) portion wise at 10° C. The reaction mixture was stirred at ambient temperature for 3 h, and was evaporated under reduced pressure. The reaction mixture was diluted with saturated $Na_2S_2O_3$ (100.0 mL) at 10° C. and extracted with EtOAc (2×100 mL). Combined organic layer was washed with brine, dried over anhydrous $Na_2SO_4$ and evaporated under reduced pressure to get desired crude, which was purified by column chromatography(100-200 mesh silica gel, eluent: 15% ethyl acetate in hexane) of the title compound (15 g, 61%) as a brown solid. LCMS rt 3.27 min MH+204. 1H NMR (400 MHz, DMSO-$d_6$) δ 7.09 (t, J=8.2, 1H), 6.40 (d, J=8.52, 1H), 1.98 (s, 3H).

Step 2

4-Bromo-3-fluoro-2-methyl-phenylamine

To a stirred solution of 4-Bromo-3-fluoro-2-methyl-phenylamine (15.0 g, 73.5 mmol) in acetic acid (200 mL) was added sodium nitrite (10 g, 147 mmol) portion wise at 10° C. and reaction mixture was stirred at rt for 16 h. Upon completion, aqueous NaOH (50%) was added to the reaction mixture at −10° C. dropwise with vigorous stirring until pH was 7-8. The mixture was then extracted with ethyl acetate. The organic layer was dried over sodium sulphate and concentrated under reduced pressure to get the crude compound which was purified by column chromatography on silica gel (0-40% EtOAc in Hexane) to afford the title compound (10 g, 63%) as a off white solid. LCMS rt 3.03 min MH+214. 1H NMR (400 MHz, $CDCl_3$) δ 10.44 (brs, 1H), 8.14 (s, 1H), 7.49-7.45 (m, 1H), 7.19 (d, J=8.76, 1H).

Step 3

5-Bromo-4-fluoro-1-(tetrahydro-pyran-2-yl)-1H-indazole

To a stirred solution of 5-Bromo-4-fluoro-1H-indazole (10.0 g, 46 mmol) in dichloromethane (300.0 mL) was 3,4-dihydropyran (11.7 g, 139 mmol) followed by PTSA (800 mg, 4.6 mmol) and the reaction mixture was stirred at ambient temperature for 12 h under nitrogen. After completion, the reaction mixture was diluted with DCM, washed successively with saturated $NaHCO_3$ solution and brine, combined organic layer was dried over anhydrous $Na_2SO_4$ and evaporated under reduced pressure to get the crude compound, which was purified by column chromatography (100-200 mesh silica gel, eluent: 5% ethyl acetate in hexane) to get the title compound (8 g, 57%) as a off white solid.

LCMS rt 3.83 min MH+299. 1H NMR (400 MHz, $CDCl_3$) δ 8.05 (s, 1H), 7.46-7.43 (m, 1H), 7.28 (d, J=8.84, 1H), 5.69-5.67 (m, 1H), 3.99-3.86 (m, 1H), 3.74-3.70 (m, 1H), 2.53-2.45 (m, 1H), 2.13-2.09 (m, 2H), 1.86-1.71 (m, 4H).

Step 4

4-Fluoro-1-(tetrahydro-pyran-2-yl)-5-(4,4,5,5-tetramethyl-[1,3,2]dioxaborolan-2-yl)-1H-indazole To a stirred solution of 5-Bromo-4-fluoro-1-(tetrahydro-pyran-2-yl)-1H-indazole (8 g, 26.7 mmol) in 1,4-dioxane (200 ml) was added bispinacolatodiborane (13.6 g, 53.5 mmol) followed by potassium acetate (7.8 g, 80.3 mmol). The reaction mixture was deoxygenated with argon, then to the reaction mixture was added [1,1'-Bis(diphenylphosphino)ferrocene]-palladium(II) chloride, complex with dichloromethane (2.2 g, 2.67 mmol) and the reaction mixture was allowed to stir at 90° C. for 16 hours under nitrogen. The solvent was evaporated under reduced pressure, the residue was diluted with ethyl acetate, filtered over celite bed. Filtrate was then washed successively with water and brine. The organic layer was dried over sodium sulphate and evaporated under reduced pressure to give the crude product, which was purified by column chromatography (100-200 mesh silica gel, eluent: 5% ethyl acetate in hexane) to get the title compound (6 g, 64%) as white solid. 1H NMR (400 MHz, $CDCl_3$) δ 8.08 (s, 1H), 7.68-7.65 (m, 1H), 7.31 (d, J=8.56, 1H), 5.70-5.67 (m, 1H), 4.02-3.99 (m, 1H), 3.76-3.70 (m, 1H), 2.54-2.52 (m, 1H), 2.16-2.03 (m, 2H), 1.77-1.65 (m, 4H), 1.36 (s, 12H).

Preparation of Intermediates 1-61

Intermediate 1

3-bromo-2-(propan-2-yl)-6-[3-(trifluoromethyl)phenyl]imidazo[1,2-a]pyrazine

Step 1

6-bromo-2-(propan-2-yl)imidazo[1,2-a]pyrazine 2-amino-5-bromopyrazine (10 g, 57 mmol) and 1-bromo-3-methyl-butan-2-one (20 mL) were dissolved in acetonitrile (50 mL) and heated at 100° C. in a sealed tube for 3 days. The reaction was quenched with sodium bicarbonate solution and filtered and extracted with ethyl acetate, organic layer was dried over sodium sulphate and concentrated to give a brown liquid that was purified by column chromatography (100-200 mesh silica gel, eluent; 50% ethyl acetate in DCM) to give the title compound as a brown semi solid (3.5 g, 25%). UPLC rt 2.7 min $MH^+$ 242. $^1H$ NMR (400 MHz, DMSO-$d_6$) δ 8.79 (s, 1H), 8.18 (s, 1H), 7.45 (s, 1H), 3.15 (h, 1H), 1.36 (d, 6H).

Step 2

2-(propan-2-yl)-6-[3-(trifluoromethyl)phenyl]imidazo[1,2-a]pyrazine

A mixture of 6-bromo-2-(propan-2-yl)imidazo[1,2-a]pyrazine (2.0 g, 8.3 mmol) and 3-(trifluoromethyl)phenylboronic acid (1.9 g, 10 mmol) was dissolved in dioxane:$H_2O$ (3:1, 20 mL) and treated with $K_3PO_4$ (5.3 g, 25 mmol). The mixture was degassed for 20-30 min, treated with Pd-dppf-DCM complex (2.0 g, 2.5 mmol) and heated at 90° C. for 16 h, After completion, the reaction was quenched with water and extracted with ethyl acetate. The organic layer was dried over sodium sulphate and concentrated to get crude compound, which was purified by column chromatography (100-200 mesh silica gel, eluent: 10% ethyl acetate in DCM) to give the title compound (2.3 g, 90%). UPLC rt 3.4 min $MH^+$ 306. $^1H$ NMR (400 MHz, DMSO-$d_6$) δ 9.12 (s, 1H), 8.43 (s, 1H), 8.19 (s, 1H), 8.10 (d, 1H), 7.65 (d, 1H), 7.59 (t, 1H), 7.54 (s, 1H), 3.21 (h, 1H), 1.40 (d, 6H).

Step 3

3-bromo-2-(propan-2-yl)-6-[3-(trifluoromethyl)phenyl]imidazo[1,2-a]pyrazine 2-(propan-2-yl)-6-[3-(trifluoromethyl)phenyl]imidazo[1,2-a]pyrazine (2.3 g, 7.5 mmol) was dissolved in DCE (25 mL) and treated with N-Bromosuccinimide (1.6 g, 9.1 mmol) and the mixture was heated at 85-90° C. for 8 h, The reaction mixture was concentrated and the crude was purified by combiflash chromatography to get the title compound as a brown solid (1.5 g, 52%) UPLC rt 4.0 min $MH^+$ 386. $^1H$ NMR (400 MHz, DMSO-$d_6$) δ 9.07 (s, 1H), 8.38 (s, 1H), 8.25 (s, 1H), 8.15 (d, 1H), 7.68 (d, 1H), 7.62 (t, 1H), 3.30 (h, 1H), 1.40 (d, 6H).

Intermediate 37

3-Chloro-6-(4-fluoro-3-pentafluoroethyl-phenyl)-2-trifluoromethyl-imidazo[1,2-a]pyrazine Step-1

6-Bromo-2-trifluoromethyl-imidazo[1,2-a]pyrazine

To a stirred solution of 2-amino-5-bromo-pyrazine (2 g, 11.5 mmol) in isopropanol (60 ml) was added 3-Bromo-1,1,1-trifluoroacetone (3 g, 3 mmol) and the mixture was allowed to stir at 90° C. for 72 h. After complete consumption of the starting material (monitored by both TLC and LCMS) the solvent was evaporated under reduced pressure, the residue was diluted with ethyl acetate basified with saturated bicarbonate solution, filtered overcelite bed. Aqueous part was discarded and organic part was washed successively with saturated sodium bicarbonate solution and brine, the organic layer dried over sodium sulphate, evaporated under reduced pressure to get crude compound, which was purified by column chromatography (100-200 mesh silica gel, eluent:20% ethyl acetate in DCM) to give the title compound (1 g, 32.7%) as brown solid. LCMS rt 2.87 min MH+ 266. 1H NMR (400 MHz, DMSO-$d_6$) δ 9.13 (s, 1H) 8.99 (s, 1H), 8.64 (s, 1H).

Step-2

6-Bromo-3-chloro-2-trifluoromethyl-imidazo[1,2-a]pyrazine

To a stirred solution of 6-Bromo-2-trifluoromethyl-imidazo[1,2-a]pyrazine (1 g, 3.75 mmol) in dry DMF (25 ml) was added N-Chlorosuccinimide (753 mg, 5.63 mmol) and the reaction mixture was allowed stir at 90° C. 24 h. After complete consumption of the starting material (monitored by both TLC and LCMS) the reaction mixture was diluted with ethyl acetate, washed successively with water and brine. The organic part was dried over sodium sulphate and evaporated under reduced pressure to get crude compound which was purified by column chromatography (100-200 mesh silica gel, eluent: 10% ethyl acetate in DCM) to give the title compound (900 mg, 79.7%) of as light brown solid.

LCMS rt 3.16 min MH+ 301. 1H NMR (400 MHz, DMSO-$d_6$) δ 9.17 (s, 1H) 8.94 (s, 1H).

Step-3

3-Chloro-6-(4-fluoro-3-pentafluoroethyl-phenyl)-2-trifluoromethyl-imidazo[1,2-a]pyrazine A mixture of 6-Bromo-3-chloro-2-trifluoromethyl-imidazo[1,2-a]pyrazine (800 mg, 2.67 mmol) and 2-(4-Fluoro-3-pentafluoroethyl-phenyl)-4,4,5,5-tetramethyl-[1,3,2]dioxaborolane) (1 g, 2.93 mmol) was dissolved in 1,4-dioxane:$H_2O$ (4:1, 15 mL) and treated with $K_3PO_4$ (1.7 g, 8 mmol). The mixture was degassed for 20-30 min, treated with Bis(diphenylphosphino)ferrocene]palladium(II) chloride, complex with dichloromethane (217 mg, 0.27 mmol) and heated at 90° C. for 16 h. After completion, the reaction was quenched with water and extracted with ethyl acetate. The organic layer was dried over sodium sulphate and concentrated to get crude compound, which was purified by column chromatography (100-200 mesh silica gel, eluent: 10% ethyl acetate in DCM) to give the title compound (700 mg, 60.5%). LCMS rt 4 min MH+ 434. 1H NMR (400 MHz, DMSO-$d_6$) δ 9.40 (s, 1H), 9.26 (s, 1H), 8.63 (br. s, 1H), 8.53 (d, J=5.08 Hz, 1H), 7.75-7.70 (m, 1H).

Intermediates 2-4, 6-9, 12-14, 16-20, 23-24, 28-29, 30-31, 33, 38-61

Prepared using a similar method to Intermediate 1 or 37 from the appropriate halo-ketone and boronic acid or boronate.

Intermediate 5

Prepared by a modification of the route to the above intermediates using the scheme below.

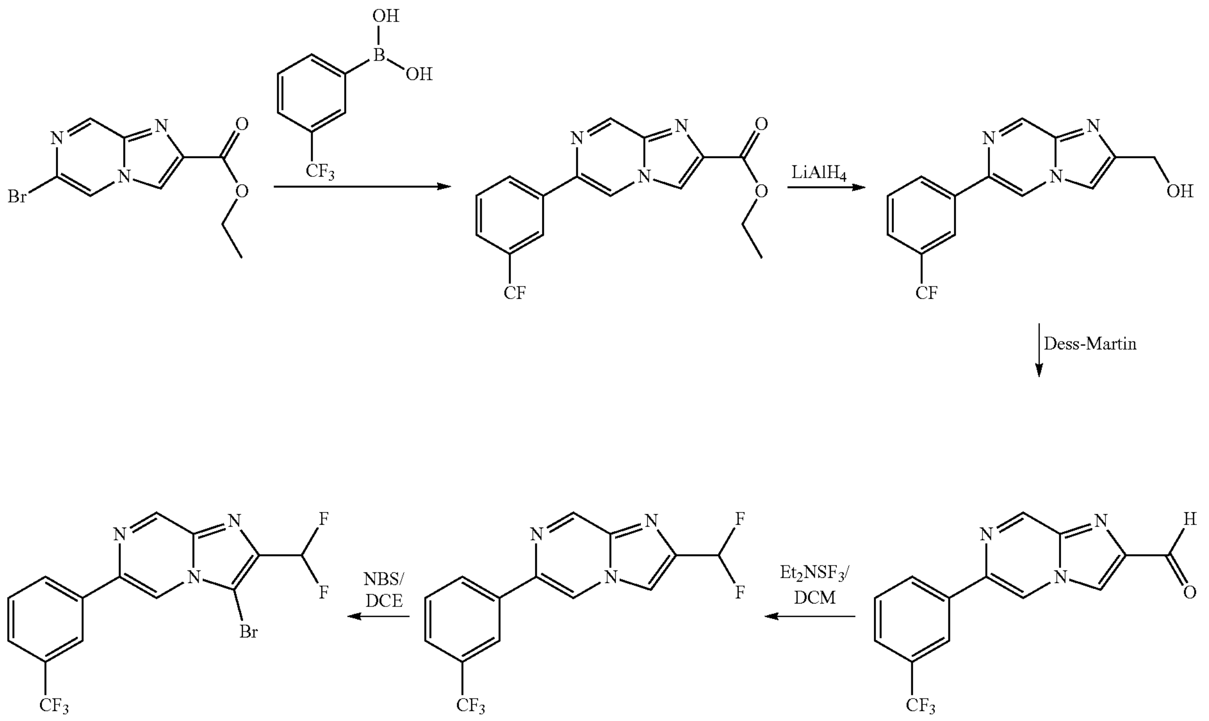

Intermediates 15, 21 and 25

Prepared from the appropriate 3-iodo imidazo[1,2-a]pyrazine using the method below Intermediate 15

4-{6-bromo-2-methylimidazo[1,2-a]pyrazin-3-yl}-3,5-difluorophenol

Step 1

6-bromo-2-methyl imidazo[1,2-a]pyrazine 2-amino-5-bromopyrazine (10 g, 57 mmol) and 1-bromo-2,2-dimethoxy-propane (15 g) were dissolved in IPA (30 mL) and heated at 100° C. in a sealed tube for 3 days. The reaction was quenched with sodium bicarbonate solution and filtered and extracted with ethyl acetate; the organic layer was dried over sodium sulphate and concentrated to give a brown solid that was used for the next step without further purification.

Step 2

6-bromo-3-iodo-2-methyl-imidazo[1,2-a]pyrazine

To a well stirred solution of 6-bromo-2-methyl imidazo[1,2-a]pyrazine (3 g, 14.15 mmol) in DMF (15 ml) was added N-Iodoosuccinimide (3.82 g, 16.98 mmol) and the reaction mixture was allowed to stir at 80° C. for 12 h under nitrogen. After complete consumption of the SM (Monitored by LCMS) the reaction mixture was diluted with ethyl acetate, washed successively with water and brine, dried over sodium sulphate and evaporated under reduced pressure to get the crude compound, which was purified by column chromatography (100-200 mesh silica gel, eluent; 20% ethyl acetate in hexane) to give the title compound as a yellowish solid [1.5 g, 31% (After two steps)]. LCMS rt 2.89 min $MH^+$ 338. $^1H$ NMR (400 MHz, DMSO-$d_6$) δ 8.74 (s, 1H), 8.49 (s, 1H), 2.44 (s, 3H).

Step 3

4-{6-bromo-2-methylimidazo[1,2-a]pyrazin-3-yl}-3,5-difluorophenol

A mixture of 6-bromo-3-iodo-2-methyl-imidazo[1,2-a]pyrazine (120 mg, 0.355 mmol) and 2,6-difluoro-4-hydroxyphenylboronic acid (61.8 mg, 0.355 mmol) was dissolved in THF:$H_2O$ (3:1, 4 mL) and treated with KF (62 mg, 1.065 mmol). The mixture was degassed for 20-30 min, treated with bis(tri-tert-butylphosphine)palladium(0) (18 mg, 0.036 mmol) and heated at 120° C. for 1 h under microwave irradiation (200 watt), After completion, the reaction was quenched with water and extracted with ethyl acetate. The organic layer was dried over sodium sulphate and concentrated to get crude compound, which was used in the preparation of Example 31 without further purification.

Intermediate 11

3-bromo-2-(propan-2-yl)-5-[3-(trifluoromethyl)phenyl]pyrazolo[1,5-c]pyrimidine

Step 1

[4-bromo-3-(propan-2-yl)-1H-pyrazol-5-yl]methanol

To the stirred solution of ethyl 4-bromo-3-(propan-2-yl)-1H-pyrazole-5-carboxylate (400 mg, 1.5 mmol) in THF (4 mL) was added 2.5 M LAH (Lithium Aluminium Hydride) solution (2.5M in THF, 87 μL, 2.3 mmol) in THF at 0° C. and stirred for 3 h. The reaction was then quenched by saturated solution of $Na_2SO_4$ and filtered with celite and evaporated under reduced pressure to give the title compound (290 mg, 86%). UPLC rt 3.1 min $MH^+$ 261. $^1H$ NMR (400 MHz, DMSO-$d_6$) δ 12.79 (s, 1H), 4.95 (br.s, 1H), 4.37 (s, 2H), 2.94 (m, 1H), 1.21 (d, 6H).

Step 2

4-bromo-5-(bromomethyl)-3-(propan-2-yl)-1H-pyrazole

To ice cold [4-bromo-3-(propan-2-yl)-1H-pyrazol-5-yl]methanol (280 mg, 1.28 mmol) was added $SOBr_2$ (7 mL) and the mixture was heated at 40° C. for 2 h. Volatiles were removed under vacuum and the residue triturated with hexane to afford the title compound as a pale yellow solid HBr salt (300 mg, 83%) UPLC rt 2.5 min $MH^+$ 283. $^1H$ NMR (400 MHz, DMSO-$d_6$) δ 4.53 (s, 2H), 2.98 (m, 1H), 1.22 (d, 6H).

Step 3

3-bromo-2-(propan-2-yl)-5-[3-(trifluoromethyl)phenyl]pyrazolo[1,5-c]pyrimidine

To a solution of 4-bromo-5-(bromomethyl)-3-(propan-2-yl)-1H-pyrazole (100 mg, 0.36 mmol) in DCM (2 mL) at −10° C. was added 1-(3-trifluoromethylphenyl)-1-tosyl methyl isocyanide (120 mg, 0.36 mmol) and benzyl triethylammonium chloride (16 mg, 0.07 mmol) and then added drop wise a solution of of 30%-NaOH in water (2 mL). The resultant reaction mixture was maintained at −10° C. for 3 h. The mixture was extracted into DCM, the organic layer was dried and concentrated under vacuum to afford crude product. The crude was chromatographed on silica gel column using 3%-EtOAc in hexane to afford title compound as a colourless solid (30 mg, 22%). UPLC rt 2.7 min $MH^+$ 384. $^1H$ NMR (400 MHz, DMSO-$d_6$) δ 9.59 (s, 1H), 8.57 (s, 1H), 8.54 (d, 1H), 8.27 (s, 1H), 7.82 (d, 1H), 7.75 (t, 1H), 3.25 (h, 1H), 1.36 (d, 6H).

Intermediates 10, 22, 26, 27, and 34-36

Prepared from the appropriate pyrazole derivative and tosyl isocyanide. 1-(4-fluoro-3-trifluoromethylphenyl)-1-tosyl methyl isocyanide was prepared from (4-fluoro-3-trifluoromethylphenyl) methyl isocyanide and tosyl fluoride. 1-(4-fluoro-3-pentafluoroethylphenyl)-1-tosyl methyl isocyanide was prepared from (4-fluoro-3-pentafluoroethylphenyl) methyl isocyanide and tosyl fluoride.

Intermediate 32
3-bromo-2-(propan-2-yl)-5-[3-(trifluoromethyl)phenyl]pyrazolo[1,5-a]pyridine
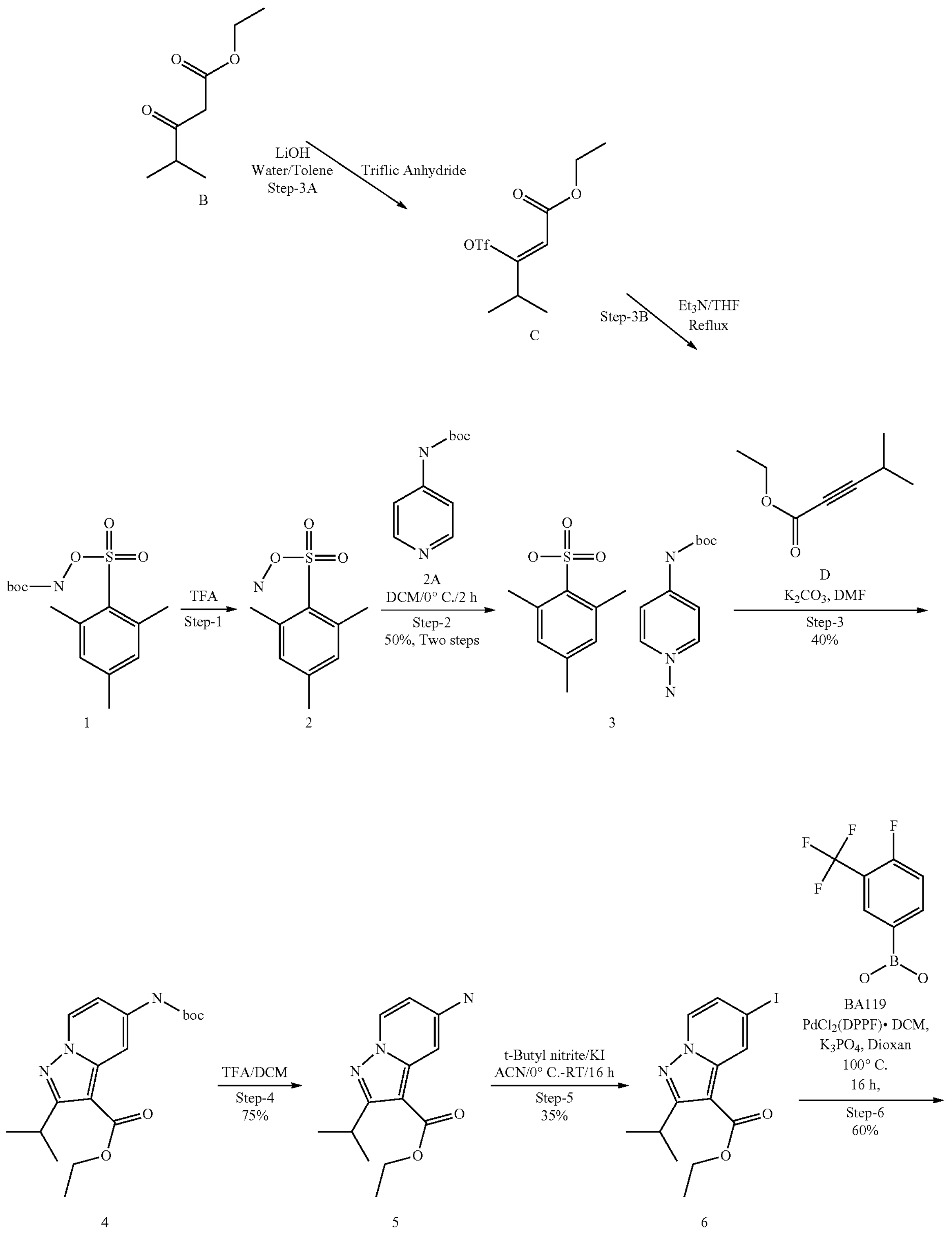

-continued

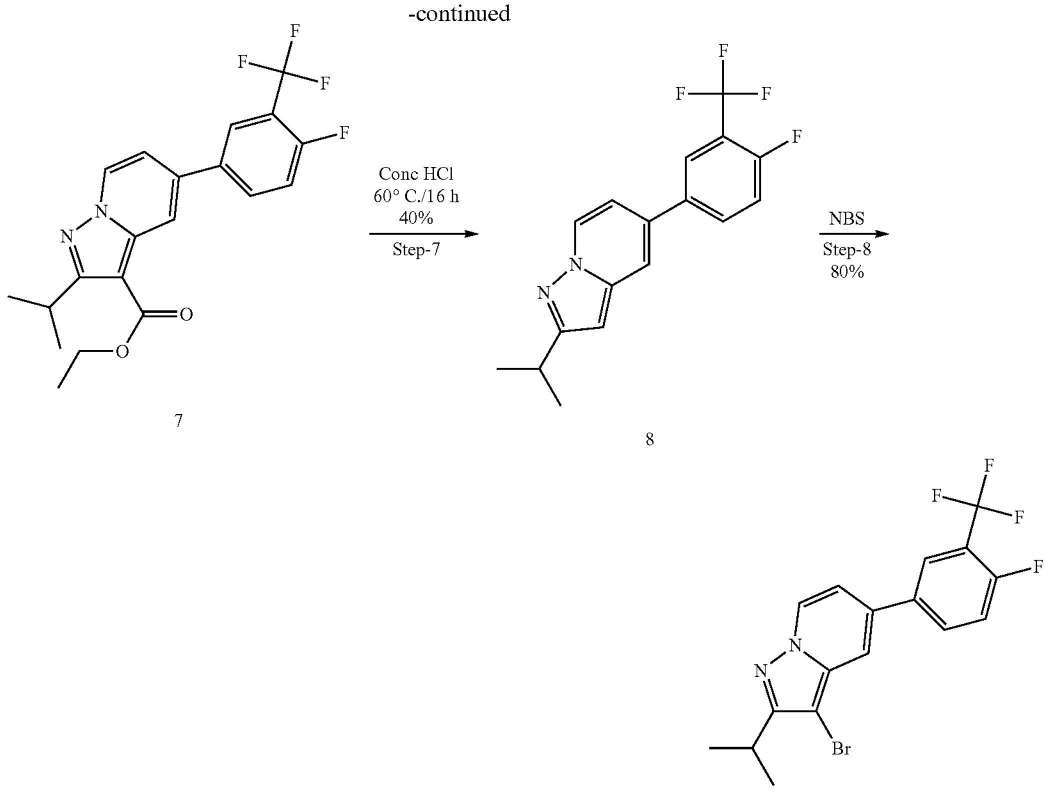

7

8

9

Step-1

2-[(aminooxy)sulfonyl]-1,3,5-trimethylbenzene

TFA (160 ml) was added drop wise to tert-butyl [(mesitylsulfonyl)oxy]carbamate 1 (40 g, 126.98 mmol) at 0° C. and the reaction mixture was allowed to stir at this temperature for 1 h. The reaction mixture was poured slowly into ice water. The precipitate formed was filtered and washed thoroughly with water to remove trace amount of TFA to afford 2-[(aminooxy)sulfonyl]-1,3,5-trimethylbenzene. The solid was dissolved in DCM (200 mL) and the solution was used in the next step immediately without further analysis.

Step-2 tert-butyl N-(1-amino{4}-pyridin-4-yl)carbamate. 2,4,6-trimethylbenzene-1-sulfonic acid To a solution of Pyridin-4-yl-carbamic acid tert-butyl ester (2.30 g, 11.06 mmol) in DCM (30 mL) was added drop wise a solution of compound 2-[(aminooxy)sulfonyl]-1,3,5-trimethylbenzene in DCM (30 mL) at 0-5° C. and continued stirring at this temperature for 2 h. The reaction mixture was concentrated under reduced pressure to afford the target compound (2 g, 50% in two step) as brown gum. It was used in the next step without further purification. $^1$H NMR (400 MHz, DMSO-$d_6$) δ 10.93 (1H, br. s), 8.54 (2H, d, J=6.9 Hz), 7.85 (2H, d, J=6.8 Hz s), 6.73 (2H, s), 2.16 (3H, s), 1.51 (9H, s) [possibly $SO_3\underline{H}$ proton was not seen in the NMR].

Step-3 A ethyl 4-methyl-2-[(trifluoromethane)sulfonyloxy]pent-2-enoate

Ethyl isobutyrylacetate (5 g, 31 mmol) was added to a round-bottom flask and dissolved in toluene (150 ml). The solution was cooled with an ice bath to 5-10° C. (internal temperature) followed by addition of a saturated aqueous solution of LiOH (50 mL, 240 mmol) in one portion. The resulting biphasic mixture was vigorously stirred at 5-10° C. for 5 minutes followed by the addition of triflic anhydride (13 ml, 79 mmol) dropwise at a rate to maintain the internal temperature between 5-15° C. Upon completion of the reaction (as judged by TLC, typically <10 min), the biphasic solution was diluted with water and the layers were separated. The aqueous layer was extracted with EtOAc. The combined organic layers were washed with water, brine and dried over sodium sulphate. The organic layer was filtered and concentrated under reduced pressure to get the title compound (6.2 g, 67%) as colourless liquid.

$^1$H NMR (400 MHz, DMSO-$d_6$) 6.09 (1H, s), 4.19-4.13 (2H, m), 2.57-2.53 (1H, m), 1.24-1.14 (9H, m)

Step-313

Ethyl-4-methylpent-2-ynoate

To a stirred solution of Ethyl ethyl 4-methyl-2-[(trifluoromethane)sulfonyloxy]pent-2-enoate (6.1 g, 21 mmol) in dry THF (40 ml) was added triethyl amine (4 ml, 29 mmol) and the reaction mixture was allowed to stir at 80° C. for 16 h under nitrogen. The reaction mixture was then cooled to RT and evaporated under reduced pressure to afford the title compound (2.5 g, 84.2%) as yellow oil.

$^1$H NMR (400 MHz, DMSO-$d_6$) 4.16-4.10 (1H, m), 3.09-3.06 (2H, m), d 1.24-1.14 (9H, m).

Step-3 ethyl-{[(tert-butoxy)carbonyl]amino}-2-(propan-2-yl)pyrazolo[1,5-a]pyridine-3-carboxylate To a stirred solution of tert-butyl N-(1-amino{4}-pyridin-4-yl)carbamate. 2,4,6-trimethylbenzene-1-sulfonic acid (4.5 g, 11 mmol) in dry DMF (12 ml) was added ethyl-4-methylpent-2-ynoate (1.5 g, 11 mmol) followed by potassium carbonate (3 g, 22 mmol) and the reaction mixture was allowed to stir at room temperature for 16 h under nitrogen. After complete consumption of the SM (Monitored by LCMS) the reaction mixture was diluted with ethyl acetate, washed successively with water and brine, dried over sodium sulphate and evaporated under reduced pressure to get the crude compound, which was purified by column chromatography (100-200 mesh silica gel, eluent; 20% ethyl acetate in hexane) to give the title compound as a brown solid (1.6 g, 44%). LCMS rt 4.20 min $MH^+$ 348. $^1$H NMR (400 MHz, DMSO-$d_6$) δ 9.93 (s, 1H). 8.61 (d, 1H, J=7.44 Hz), 8.29 (s, 1H), 7.08 (d, 1H, J=7.44 Hz) 4.28-4.24 (m, 2H), 3.68-3.65 (m, 1H), 1.38-1.15 (m, 18H).

Step-4

Ethyl-5-amino-2-(propan-2-yl)pyrazolo[1,5-a]pyridine-3-carboxylate

To a stirred solution of ethyl-5-{[(tert-butoxy)carbonyl]amino}-2-(propan-2-yl)pyrazolo[1,5-a]pyridine-3-carboxylate (1.7 g, 4.8 mmol) in dry DCM (12 ml) was added trifluoroacetic acid (3.6 ml) at 0° C. and the reaction mixture was allowed to stir at room temperature for 1 h under nitrogen. After complete consumption of the SM (Monitored by LCMS) the volatiles were evaporated under reduced pressure to get the crude compound, which was purified by column chromatography (100-200 mesh silica gel, eluent; 30% ethyl acetate in hexane) to give the title compound as a off white solid (0.9 g, 75%). LCMS rt 3.34 min $MH^+$ 248. $^1$H NMR (400 MHz, DMSO-$d_6$) δ 8.30 (d, 1H, J=7.32 Hz), 6.90 (s, 1H), 6.41 (d, 1H, J=7.44 Hz), 6.18 (brs, 2H), 4.23-4.18 (m, 2H), 3.63-3.56 (m, 1H), 1.32-1.18 (m, 9H).

Step-5

Ethyl-5-iodo-2-(propan-2-yl)pyrazolo[1,5-a]pyridine-3-carboxylate

To a stirred solution of ethyl-5-amino-2-(propan-2-yl)pyrazolo[1,5-a]pyridine-3-carboxylate (800 mg, 3.23 mmol) in dry acetonitrile (20 ml) at 0° C. were added tert-Butyl nitrite (0.8 ml, 6.47 mmol) followed by potassium iodide (1.1 g, 6.47 mmol) and the reaction mixture was allowed to stir at 70° C. for 16 h under nitrogen. After complete consumption of the SM (Monitored by LCMS) the reaction mixture was diluted with ethyl acetate, washed successively with water and brine, dried over sodium sulphate and evaporated under reduced pressure to get the crude compound, which was purified by column chromatography over silica gel (100-200 mesh silica gel, eluent; 10% ethyl acetate in hexane) to give the title compound as a white solid (550 mg, 47.41%). LCMS rt 2.78 min $MH^+$ 359 (non-polar method). $^1$H NMR (400 MHz, DMSO-$d_6$) δ 0.8.59 (d, 1H, J=7.28 Hz), 8.39 (s, 1H), 7.33 (d, 1H, J=5.08 Hz) 4.31-4.30 (m, 2H), 3.72-3.69 (m, 1H), 1.35-1.29 (m, 9H).

Step-6

Ethyl-5-[4-fluoro-3-(trifluoromethyl)phenyl]-2-(propan-2-yl)pyrazolo[1,5-a]pyridine-3-carboxylate Ethyl-5-iodo-2-(propan-2-yl)pyrazolo[1,5-a]pyridine-3-carboxylate (0.25 g, 0.69 mmol) and 4-fluoro-3-trifluoromethylphenylboronic acid (0.21 g, 1.03 mmol) were dissolved in dioxane/water (4:1, 5 mL) and treated with $K_3PO_4$ (0.44 g, 2.07 mmol). The solution was degassed 20-30 min before addition of $PdCl_2$(dppf). DCM catalyst (57 mg, 0.07 mmol), The reaction mixture was heated to 90° C. for 16 h, cooled to room temperature, and partitioned between ethyl acetate and water. The organic layer was dried over sodium sulphate and concentrated under reduced pressure. The crude product was purified by column chromatography (100-200 mesh silica gel, by elution with 10% ethyl acetate in hexane). Fractions containing the desired product were combined and evaporated under reduced pressure to give the title compound (240 mg, 85%) UPLC rt 1.94 min $MH^+$ 395 (3 min run) $^1$H NMR (400 MHz, DMSO-$d_6$) δ 8.91 (d, J=7.36 Hz, 1H), 8.26 (s, 1H) 8.20-8.19 (m, 1H), 8.13 (d, J=6.64 Hz, 1H), 7.70 (t, J=10.16 Hz, 1H), 7.52 (dd, J=7.2 Hz, 1.02 Hz, 1H), 4.36-4.30 (m, 2H), 3.77-3.74 (m, 1H), 1.38-1.32 (m, 9H).

Step-7

5-[4-fluoro-3-(trifluoromethyl)phenyl]-2-(propan-2-yl)pyrazolo[1,5-a]pyridine

Ethyl-5-[4-fluoro-3-(trifluoromethyl)phenyl]-2-(propan-2-yl)pyrazolo[1,5-a]pyridine-3-carboxylate (0.25 g, 0.63 mmol) was taken in cone HCl (60 ml) and the reaction mass was heated to reflux for 16 h. After complete consumption of the SM (Monitored by LCMS) the reaction mixture was cooled to 0° C., to it was added 2N NaOH dropwise until pH8. It was then extracted with ethyl acetate, washed successively with water and brine, dried over sodium sulphate and evaporated under reduced pressure to get the crude compound, which was purified by column chromatography over silica gel (100-200 mesh silica gel, eluent; 10% ethyl acetate in hexane) to give the title compound as a white solid (90 mg, 44%). UPLC rt 1.87 min (3 min run) $MH^+$ 323.

$^1$H NMR (400 MHz, DMSO-$d_6$) δ 0.8.66 (d, J=7.04 Hz, 1H), 8.16-8.10 (m, 2H) 8.01 (s, 1H), 7.65 (t, J=9.64 Hz, 1H), 7.21 (d, J=7.08 Hz, 1H) 6.49 (s, 1H), 3.12-3.09 (m, 1H), 1.34-1.30 (m, 6H).

Step-8

3-bromo-5-[4-fluoro-3-(trifluoromethyl)phenyl]-2-(propan-2-yl)pyrazolo[1,5-a]pyridine To a stirred solution of 5-[4-fluoro-3-(trifluoromethyl)phenyl]-2-(propan-2-yl)pyrazolo[1,5-a]pyridine (86 mg, 0.26 mmol) in dry acetonitrile (5 ml) at 0° C. were added N-Bromosuccinimide (57 mg, 0.32 mmol) and the reaction mixture was allowed to stir at 70° C. for 1 h under nitrogen. After complete consumption of the SM (Monitored by LCMS) the reaction mixture was diluted with ethyl acetate, washed successively with water and brine, dried over sodium sulphate and evaporated under reduced pressure to get the 89 mg of the title compound as brown solid which was used for the next step without further purification.

Intermediate 62

9-[4-(benzyloxy)-2,6-difluorophenyl]-8-(propan-2-yl)-2-[3-(trifluoromethyl)phenyl]-9H-purine was prepared by an analogous route to Example 89 step 6 product starting from 2,4,6-trifluoronitrobenzene according the following scheme

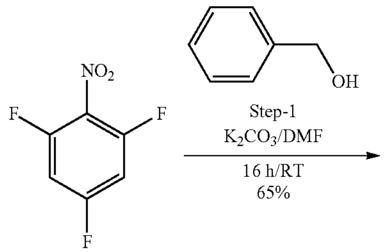

1

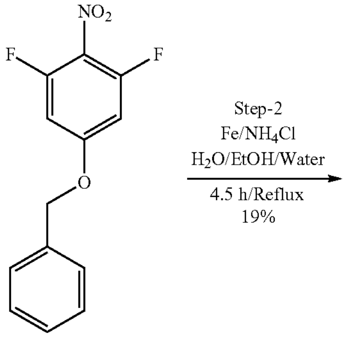

2

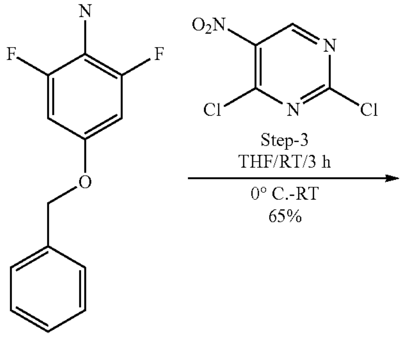

3

-continued

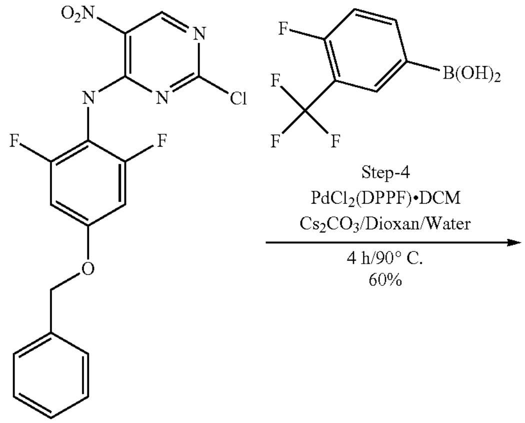

4

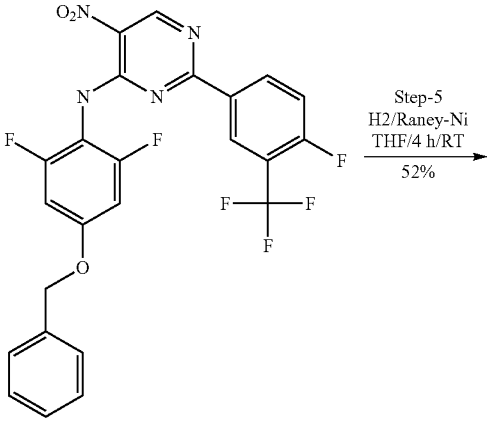

5

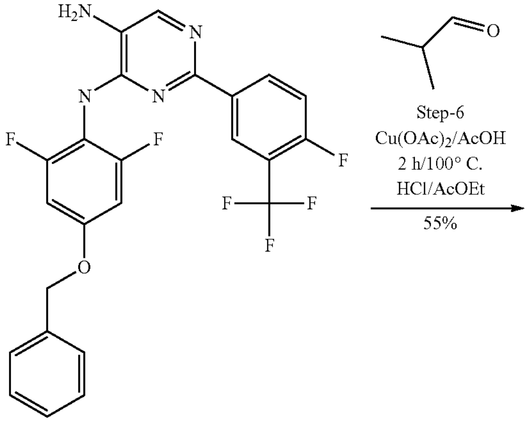

6

-continued

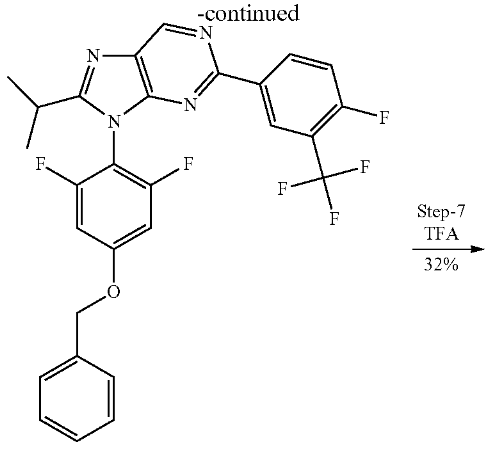

7

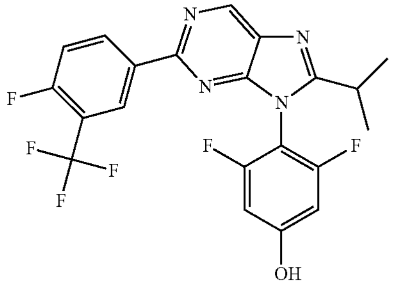

Preparation of Examples 1-90

Example 1

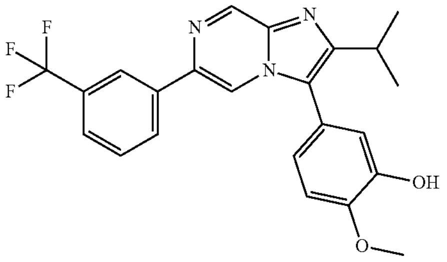 [SMILES: COc1ccc(-c2c(C(C)C)nc3cnc(-c4cccc(C(F)(F)F)c4)cn23)cc1O]

2-methoxy-5-[2-(propan-2-yl)-6-[3-(trifluoromethyl) phenyl]imidazo[1,2-a]pyrazin-3-yl]phenol 3-bromo-2-(propan-2-yl)-6-[3-(trifluoromethyl)phenyl] imidazo[1,2-a]pyrazine (1.5 g, 3.9 mmol) and 2-methoxy-5-(4,4,5,5-tetramethyl-[1,3,2]dioxaborolan-2-yl)-phenol (1.46 g, 5.9 mmol) were dissolved in dioxane/water (4:1, 30 mL) and treated with $K_3PO_4$ (2.48 g, 11.7 mmol. The solution was degassed 20-30 min before addition of Pd-118 catalyst (0.25 g, 0.39 mmol), The reaction mixture was heated to 90° C. for 16 h, cooled to room temperature, and partitioned between ethyl acetate and water. The organic layer was dried over sodium sulphate and concentrated under reduced pressure. The crude product was purified by column chromatography (100-200 mesh silica gel, by elution with 20% ethyl acetate in DCM). Fractions containing the desired product were combined and evaporated under reduced pressure. The product was crystallised from methanol to give the title compound (600 mg, 36%) UPLC rt 1.9 min $MH^+$ 428.

$^1$H NMR (400 MHz, DMSO-$d_6$) δ 9.37 (s, 1H), 9.15 (s, 1H), 8.66 (s, 1H), 8.36 (s, 1H), 8.27 (d, 1H), 7.75 (d, 1H), 7.70 (d, 1H), 7.16 (d, 1H), 7.03 (d, 1H), 6.96 (s, 1H), 3.87 (s, 3H), 3.17 (h, 1H), 1.28 (d, 6H).

Examples 4-9

Prepared Using Similar Conditions from the Corresponding 3-Chloroimidazo[1,2-a]Pyrazines

Example 2

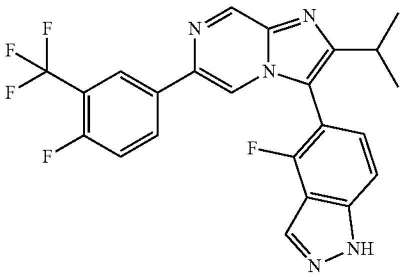 [SMILES: CC(C)c1nc2cnc(-c3ccc(F)c(C(F)(F)F)c3)cn2c1-c1ccc2[nH]ncc2c1F]

4-fluoro-5-{6-[4-fluoro-3-(trifluoromethyl)phenyl]-2-(propan-2-yl)imidazo[1,2-a]pyrazin-3-yl}-1H-indazole

Step 1

3-bromo-2-(propan-2-yl)-6-[4-fluoro-3-(trifluoromethyl) phenyl]imidazo[1,2-a]pyrazine (500 mg, 1.24 mmol) and 4-fluoro-1-(oxan-2-yl)-5-(4,4,5,5-tetramethyl-1,3,2-dioxaborolan-2-yl)-1H-indazole (861 mg, 2.49 mmol) were dissolved in dioxane/water (4:1.15 mL) and treated with $K_3PO_4$ (791 mg, 3.73 mmol. The solution was degassed with argon for 5 min before addition of tetrakis(triphenylphosphine palladium (0) catalyst (143 mg, 0.12 mmol). The reaction vessel was sealed and the mixture was heated to 100° C. for 3 h, cooled to room temperature, filtered over a celite bed to remove the solids, then partitioned between ethyl acetate and water. The organic layer was dried over sodium sulphate and concentrated under reduced pressure. The crude product was purified by column chromatography (100-200 mesh silica gel, by elution with 20% ethyl acetate in DCM). Fractions containing the desired product were combined and evaporated under reduced pressure then triturated with ether and pentane to give the title compound 4-fluoro-5-{6-[4-fluoro-3-(trifluoromethyl)phenyl]-2-(propan-2-yl)imidazo [1,2-a]pyrazin-3-yl}-1-(oxan-2-yl)-1H-indazole (600 mg, 89%) UPLC rt 4.27 min $MH^+$ 542.

Step 2

4-fluoro-5-{6-[4-fluoro-3-(trifluoromethyl)phenyl]-2-(propan-2-yl)imidazo[1,2-a]pyrazin-3-yl}-1-(oxan-2-yl)-1H-indazole (600 mg, 1.1 mmol) was dissolved in a 30% solution of TFA in DCM (4 mL) and was stirred at room temperature for 2 h. The solvents were removed under reduced pressure then the crude reaction mixture was diluted with dicholoromethane, washed successively with sodium bicarbonate solution, water and brine, the organic layer was dried over sodium sulphate and concentrated under reduced pressure to get the crude product which was purified by reverse-phase prep-HPLC to give the title compound (125 mg, 25%). UPLC rt 3.5 min $MH^+$ 458.

$^1$H NMR (400 MHz, DMSO-$d_6$) δ 13.85 (s, 1H), 9.20 (s, 1H), 8.76 (s, 1H), 8.41 (d, 2H), 8.35 (s, 1H), 7.61 (t, 1H), 7.54 (t, 1H), 7.50 (t, 1H), 3.05 (h, 1H), 1.27 (dd 6H).

Example 3

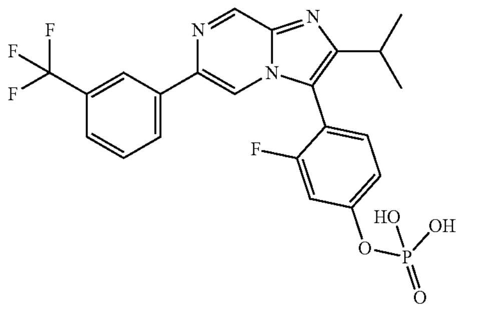 [SMILES: CC(C)c1nc2cnc(-c3cccc(C(F)(F)F)c3)cn2c1-c1ccc(OP(=O)(O)O)cc1F]

3-fluoro-4-[2-(propan-2-yl)-6-[3-(trifluoromethyl)phenyl]imidazo[1,2-a]pyrazin-3-yl]phenoxyphosphonic Acid A solution of 3-fluoro-4-[2-(propan-2-yl)-6-[3-(trifluoromethyl)phenyl]imidazo[1,2-a]pyrazin-3-yl]phenol (Example 9 600 mg, 1.45 mmol) in DCM (10 mL) was cooled to 0° C. and treated with pyridine (4 mL) followed by dropwise addition of phosphorous oxychloride (4 mL) solution in DCM (10 mL). The reaction mixture was stirred for 5 h at RT. Two further charges of pyridine and $POCl_3$ were added at 0° C. to drive the reaction to completion over 3 days. The reaction was quenched by dropwise addition of (1:1) acetone:water) (100 ml). Volatile solvents were then removed under reduced pressure. The resulting oil was dissolved in DMF and purified by reveres-phase prep-HPLC to give the title compound (104 mg, 15%). UPLC rt 2.6 min $MH^+$ 496.

$^1$H NMR (400 MHz, DMSO-$d_6$) δ 9.17 (s, 1H), 8.61 (s, 1H), 8.39 (s, 1H), 8.30 (d, 1H), 7.72 (d, 1H), 7.67 (t, 1H), 7.44 (t, 1H), 7.32 (d, 1H), 7.16 (d, 1H), 3.17 (h, 1H), 1.25 (d, 6H).

Example 31

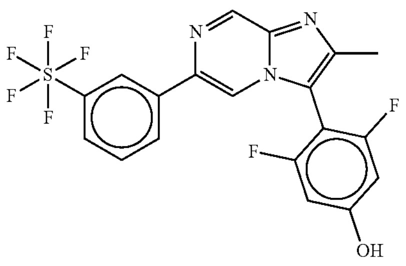

3,5-difluoro-4-[2-methyl-6-[3-(pentafluorosulfanyl)phenyl]imidazo[1,2-a]pyrazin-3-yl]phenol A mixture 4-{6-bromo-2-methylimidazo[1,2-a]pyrazin-3-yl}-3,5-difluorophenol (40 mg, 0.118 mmol) and 3-(pentafluorosulfanyl)benzeneboronic acid, pinacol ester (58 mg, 0.176 mmol) was dissolved in dioxane/water (4:1, 5 mL) and treated with $K_3PO_4$ (49.8 mg, 0.235 mmol). The solution was degassed 20-30 min before addition of [1,1'-bis(diphenylphosphino)ferrocene]palladium(II) chloride, complex with dichloromethane (19 mg, 0.024 mmol). The reaction mixture was heated to 90° C. for 16 h. The solvents were removed under reduced pressure then the crude reaction mixture was diluted with dicholoromethane, washed successively with water and brine, the organic layer was dried over sodium sulphate and concentrated under reduced pressure to get the crude product which was purified by reverse-phase prep-HPLC to give the title compound (4 mg, 7%).

UPLC rt 3.02 min $MH^+$ 464. $^1$H NMR (400 MHz, DMSO-$d_6$) δ 9.12 (s, 1H), 9.20 (s, 1H), 8.33 (s, 1H), 7.98 (m, 2H), 7.77 (d, 1H), 7.56 (t, 1H), 6.68 (d, 1H), 6.41 (m, 1H), 2.47. (s, 3H)

Example 63

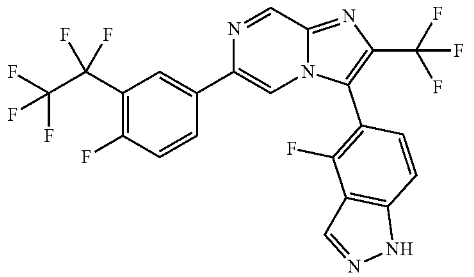 [SMILES: Fc1ccc(-c2cn3c(-c4ccc5[nH]ncc5c4F)c(C(F)(F)F)nc3cn2)cc1C(F)(F)C(F)(F)F]

Step 1

6-(4-Fluoro-3-pentafluoroethyl-phenyl)-3-[4-fluoro-1-(tetrahydro-pyran-2-yl)-1H-indazol-5-yl]-2-trifluoromethyl-imidazo[1,2-a]pyrazine A mixture of 3-Chloro-6-(4-fluoro-3-pentafluoroethyl-phenyl)-2-trifluoromethyl-imidazo[1,2-a]pyrazine (620 mg, 1.43 mmol) and 4-Fluoro-1-(tetrahydro-pyran-2-yl)-5-(4,4,5,5-tetramethyl-[1,3,2]dioxaborolan-2-yl)-1H-indazole (1 g, 2.9 mmol) was dissolved in 1,4-dioxane:$H_2O$ (4:1, 15 mL) and treated with $K_3PO_4$ (0.91 g, 4.3 mmol). The mixture was degassed for 20-30 min, treated with palladium-tetrakis (triphenylphosphine) (331 mg, 0.28 mmol) and heated at 90° C. for 16 h. After completion, the reaction was quenched with water and extracted with ethyl acetate. The organic layer was dried over sodium sulphate and concentrated to get crude compound, which was purified by column chromatography (100-200 mesh silica gel, eluent: 10% ethyl acetate in DCM) to give the title compound (480 mg, 54.3%). LCMS rt 4.33 min MH+ 618. 1H NMR (400 MHz, DMSO-$d_6$) δ 9.47 (s, 1H), 8.92-8.86 (m, 1H), 8.44-8.41 (m, 3H), 7.87-7.84 (m, 1H), 7.66-7.59 (m, 2H), 6.02 (d, J=8.84 Hz, 1H), 3.96-3.80 (m, 1H), 2.08-1.62 (m, 5H).

Step 2

3-(4-Fluoro-1H-indazol-5-yl)-6-(4-fluoro-3-pentafluoroethyl-phenyl)-2-trifluoromethyl-imidazo[1,2-a]pyrazine To a stirred solution of 6-(4-Fluoro-3-pentafluoroethyl-phenyl)-3-[4-fluoro-1-(tetrahydro-pyran-2-yl)-1H-indazol-5-yl]-2-trifluoromethyl-imidazo[1,2-a]pyrazine (480 mg, 0.78 mmol) was added 20 ml of 30% TFA in DCM at 0° C. and the reaction mixture was allowed to stir at room temperature for 1 h under nitrogen. After complete consumption of the starting material (monitored by both TLC and LCMS) the volatiles were evaporated under reduced pressure, the crude compound was diluted with dichloromethane, washed successively with sodium bicarbonate solution and brine, the organic layer dried over sodium sulphate, evaporated under reduced pressure to get crude, which was purified by reverse phase prep-HPLC to get 150 mg of the title compound (150 mg, 36.2%). UPLC rt 1.96 min (3 min run) MH+ 534. 1H NMR (400 MHz, DMSO-$d_6$) δ 13.73 (s, 1H), 9.47 (s, 1H) 8.44-8.38 (m, 3H), 7.64-7.53 (m, 3H).

Example 90

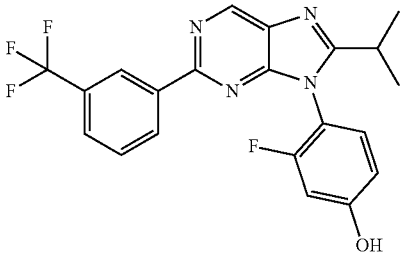 [SMILES: CC(C)c1nc2cnc(-c3cccc(C(F)(F)F)c3)nc2n1-c1ccc(O)cc1F]

Synthetic Scheme:

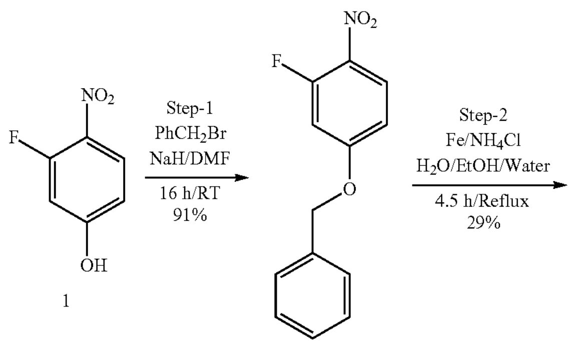

1

2

-continued

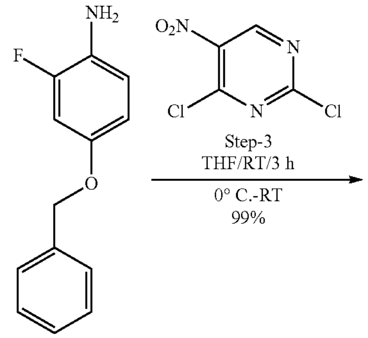

3

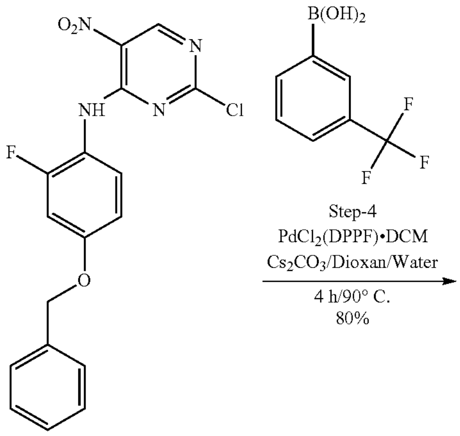

4

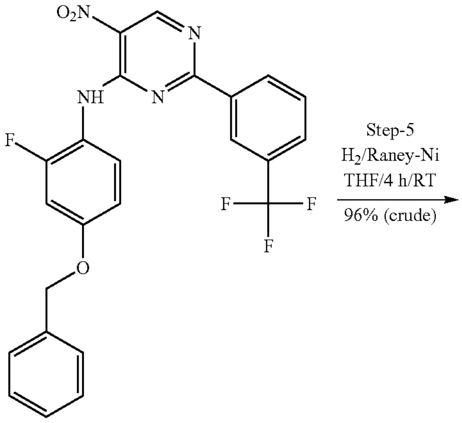

5

-continued

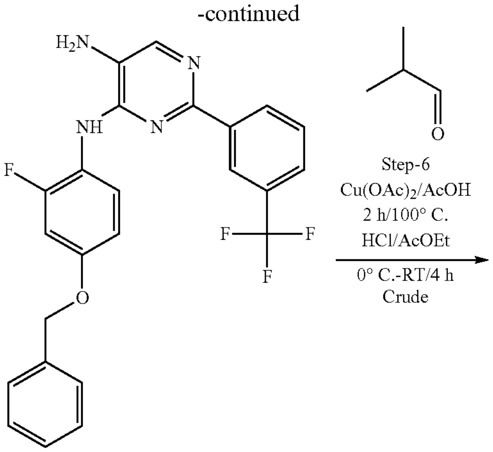

6

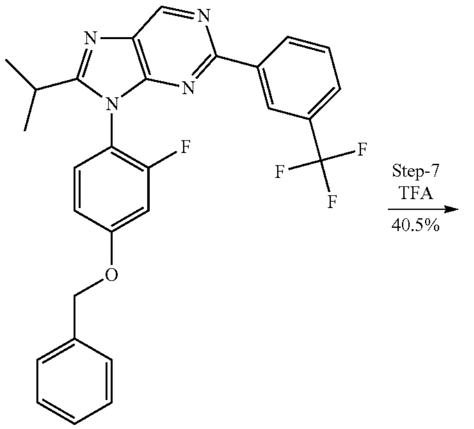

7

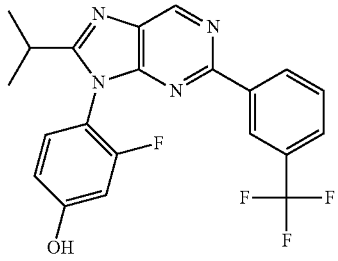

Step 1

4-Benzyloxy-2-fluoro-1-nitro-benzene (2)

To a stirred solution of 3-Fluoro-4-nitro-phenol (3.8 g, 24.2 mmol) in DMF (30 mL) was added sodium hydride (1.74 g, 72.6 mmol) portion wise at 0° C. under argon, the reaction mass was stirred at the same temperature for 30 min, after that was added benzyl bromide (3.18 ml, 26.6 mmol) to the reaction mass dropwise at 0° C. and the reaction mixture was allowed to stir for another 4 h at room temperature. After complete conversion of the starting material, the reaction mixture was pored into crushed ice to precipitate a solid which was collected by filtration to get 5.5 g (91%) of the title compound as a yellow solid. LCMS rt 3.52 min MH− 245. 1H NMR (400 MHz, $CDCl_3$) δ 8.10-7.97 (m, 1H), 7.46-7.32 (m, 5H), 6.82-6.78 (m, 1H), 6.64-6.56 (m, 1H), 5.19-5.08 (m, 2H).

Step 2

4-Benzyloxy-2-fluoro-phenylamine (3)

To a stirred solution of 4-Benzyloxy-2-fluoro-1-nitro-benzene (2) (5.5 g, 22.26 mmol) in ethanol (150 mL) and water (30 mL) was added iron powder (4.98 g, 89.07 mmol) followed by ammonium chloride (9.44 g, 178.2 mmol) and the reaction mixture was allowed to stir at 70° C. for 4 h. After complete consumption of the SM the reaction mass was filtered through celite bed, the mother liquors were evaporated, the crude reaction mass was then diluted with ethyl acetate, washed successively with water and brine, dried over sodium sulphate, evaporated under reduced pressure to give crude product, which was purified by column chromatography (100-200 mesh silica gel, eluent:30% ethyl acetate in hexane) to get 1.4 g (28.9%) of the title compound as a brown liquid. LCMS rt 3.32 min MH+ 218. 1H NMR (400 MHz, $CDCl_3$) δ 7.38-7.29 (m, 5H), 6.72-6.-6.59 (m, 3H), 5.03 (s, 2H), 3.43 (br.s, 2H).

Step 3

N-[4-(benzyloxy)-2-fluorophenyl]-2-chloro-5-nitro-pyrimidin-4-amine (4)

To a stirred solution of 4-Benzyloxy-2-fluoro-phenylamine (3) (1.4 g, 6.45 mmol) in THF(25 mL) was added 2,4-Dichloro-5-nitro-pyrimidine (1.5 g, 7.74 mmol) at 0° C. under argon and the reaction mixture was allowed to stir at room temperature for 4 h. After complete consumption of the SM, the reaction mass was poured into crushed ice to give precipitate, which was collected by filtration to get 2.4 g (99.2%) the title compound as a red solid. LCMS rt 3.65 min MH+ 375. 1H NMR (400 MHz, $CDCl_3$) δ 10.10 (brs, 1H), 9.16 (s, 1H), 7.93-7.89 (m, 1H), 7.43-7.34 (m, 6H), 6.85-6.-6.82 (m, 2H), 5.07 (s, 2H).

Step-4

N-[4-(benzyloxy)-2-fluorophenyl]-5-nitro-2-[3-(trifluoromethyl)phenyl]pyrimidin-4-amine (5)

N-[4-(benzyloxy)-2-fluorophenyl]-2-chloro-5-nitropyrimidin-4-amine (4) (2.4 g, 6.41 mmol) and 3-trifluoromethylphenylboronic acid (1.81 g, 9.62 mmol) were dissolved in dioxane/water (4:1.40 mL) and treated with $Cs_2CO_3$ (4.17 g, 12.83 mmol). The solution was degassed 20-30 min before addition of $PdCl_2$(dppf). DCM catalyst (524 mg, 0.64 mmol), The reaction mixture was heated to 90° C. for 16 h, cooled to room temperature, and partitioned between ethyl acetate and water. The organic layer was dried over sodium sulphate and concentrated under reduced pressure. The crude product was purified by column chromatography (100-200 mesh silica gel, by elution with 20% ethyl acetate in hexane). Fractions containing the desired product were combined and evaporated under reduced pressure to give the title compound as orange solid (2.5 g, 80.4%) LCMS rt 4.3 min $MH^+$ 483

$^1$H NMR (400 MHz, DMSO-$d_6$) δ 9.98 (s, 1H), 9.4 (s, 1H), 8.64 (s, 1H), 8.52-8.51 (m, 1H) 7.89-7.57 (m, 3H), 7.47-7.37 (m, 5H), 6.9-6.71 (m, 3H), 5.11 (s, 2H).

Step 5

4-N-[4-(benzyloxy)-2-fluorophenyl]-2-[3-(trifluoromethyl)phenyl]pyrimidine-4,5-diamine (6)

To a stirred solution of 4 N-[4-(benzyloxy)-2-fluorophenyl]-5-nitro-2-[3-(trifluoromethyl)phenyl]pyrimidin-4- amine (5) (220 mg, 0.455 mmol) in THF(10 mL) was added Raney nickel (100 mg). The reaction vessel was filled with hydrogen and the reaction mixture was allowed to stir at 1 atm hydrogen pressure for 1 h. After complete consumption of the SM (monitored by TLC) the reaction mass was filtered through a Celite bed, the mother liquor was evaporated to get 200 mg (96.8%) of the title compound as crude which was used for the next step without further purification. LCMS rt 3.75 min MH+ 353.

Step 6

9-[4-(benzyloxy)-2-fluorophenyl]-8-(propan-2-yl)-2-[3-(trifluoromethyl)phenyl]-9H-purine To a stirred solution of 4-N-[4-(benzyloxy)-2-fluorophenyl]-2-[3-(trifluoromethyl)phenyl]pyrimidine-4,5-diamine (6) (200 mg, 0.441 mmol) in acetic acid (20 mL) was added isobutyraldehyde (44 µL, 0.485 mmol) followed by copper acetate (80 mg, 0.441 mmol) and the reaction mixture was allowed to stir at 100° C. for 2 h under nitrogen. After complete consumption of the SM (monitored by TLC) the reaction mixture was diluted with DCM, washed successively with sodium bicarbonate and brine, dried over sodium sulphate, evaporated under reduced pressure to get the crude title compound, which was used for the next step without further purification. LCMS rt 4.50 min MH+ 507.

Step-7

3-fluoro-4-[8-(propan-2-yl)-2-[3-(trifluoromethyl)phenyl]-9H-purin-9-yl]phenol

To a stirred solution of 9-[4-(benzyloxy)-2-fluorophenyl]-8-(propan-2-yl)-2-[3-(trifluoromethyl)phenyl]-9H-purine (7) (150 mg, 0.29 mmol) in 1,2-Dichloroethane (7 mL) was added trifluoroacetic acid (4.5 mL) and the reaction mixture was allowed to stir at 90° C. for 16 h. After complete consumption of the starting material (monitored by both TLC and LCMS) the volatiles were evaporated under reduced pressure, the crude compound was diluted with dichloromethane, washed successively with sodium bicarbonate solution and brine, the organic layer dried over sodium sulphate, evaporated under reduced pressure to get crude, which was purified by reverse phase prep-HPLC to get 50 mg of the title compound (40.5%) as off white solid. UPLC rt 3.23 min MH+ 417. 1H NMR (400 MHz, DMSO-$d_6$) δ 10.61 (s, 1H), 9.21 (s, 1H) 8.58-8.54 (m, 2H), 7.85-7.57 (m, 3H), 6.96-6.87 (m, 2H), 3.04-3.01 (m, 1H), 1.31-1.22 (m, 6H).

The following compounds were made by analogous methods:

| Ex No | Structure | General method | Intermediate No. | Yield Yield | Characterisation |
|---|---|---|---|---|---|
| 4 | 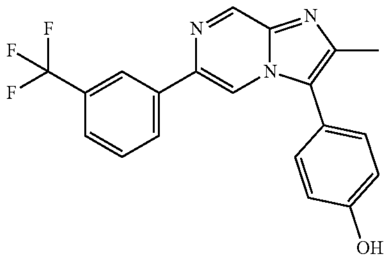 4-[2-methyl-6-[3-(trifluoromethyl)phenyl]imidazo[1,2-a]pyrazin-3-yl]phenol | 1A | 2 | 24 mg, 24% | UPLC rt 2.92 min, MH$^+$ 370 |
| 5 | 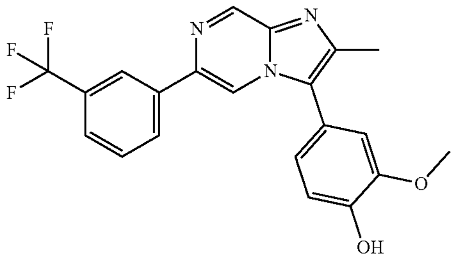 2-methoxy-4-(2-methyl-6-(3-(trifluoromethyl)phenyl)imidazo[1,2-a]pyrazin-3-yl)phenol | 1A | 2 | 22 mg, 25% | UPLC rt 3.08 min, MH$^+$ 400 |

-continued

| Ex No | Structure | General method | Intermediate No. | Yield Yield | Characterisation |
|---|---|---|---|---|---|
| 6 | 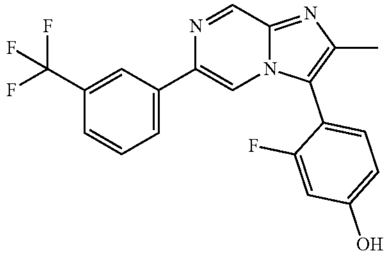 3-fluoro-4-[2-methyl-6-[3-(trifluoromethyl)phenyl]imidazo[1,2-a]pyrazin-3-yl]phenol | 1A | 2 | 10 mg, 11% | UPLC 2.98 rt min, $MH^+$ 388 |
| 7 | 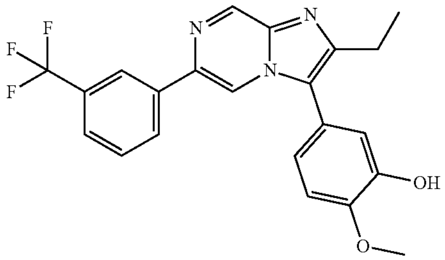 2-methoxy-5-[2-ethyl-6-[3-(trifluoromethyl)phenyl]imidazo[1,2-a]pyrazin-3-yl]phenol | 1A | 3 | 37 mg, 34% | UPLC rt 3.04 min, $MH^+$ 414 |
| 8 | 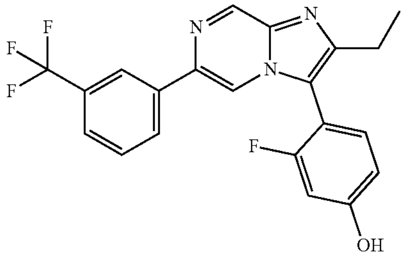 3-fluoro-4-[2-ethyl-6-[3-(trifluoromethyl)phenyl]imidazo[1,2-a]pyrazin-3-yl]phenol | 1A | 3 | 8 mg, 11% | UPLC rt 1.84 min (3 min Run) $MH^+$ 402 |
| 9 | 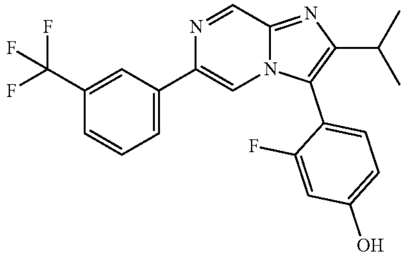 3-fluoro-4-[2-(propan-2-yl)-6-[3-(trifluoromethyl)phenyl]imidazo[1,2-a]pyrazin-3-yl]phenol | 1A | 1 | 5 mg, 7% | UPLC rt 3.11 min, $MH^+$ 416 |

-continued

| Ex No | Structure | General method | Intermediate No. | Yield Yield | Characterisation |
|---|---|---|---|---|---|
| 10 | 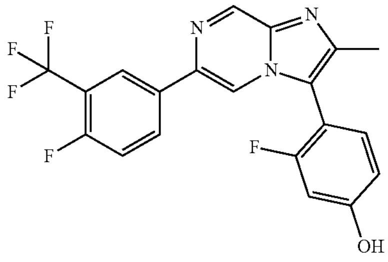 3-fluoro-4-[2-methyl-6-[4-fluoro-3-(trifluoromethyl)phenyl]imidazo[1,2-a]pyrazin-3-yl]phenol | 1B | 4 | 5 mg, 15% | UPLC rt 2.92 min, $MH^+$ 406 |
| 11 | 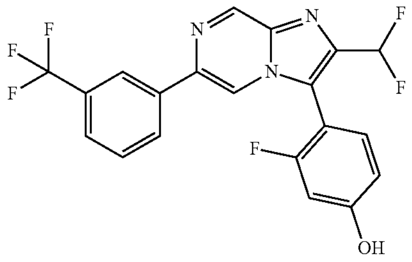 3-fluoro-4-[2-difluoromethyl-6-[3-(trifluoromethyl)phenyl]imidazo[1,2-a]pyrazin-3-yl]phenol | 1B | 5 | 5 mg, 11% | UPLC rt 1.62 min (3 min Run) $MH^+$ 424 |
| 12 | 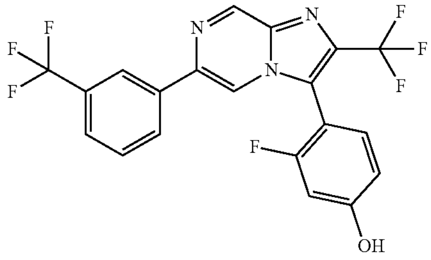 3-fluoro-4-[2-trifluoromethyl-6-[3-(trifluoromethyl)phenyl]imidazo[1,2-a]pyrazin-3-yl]phenol | 1B | 6 | 25 mg, 20% | UPLC rt 1.65 min (3 min Run) $MH^+$ 442 |
| 13 | 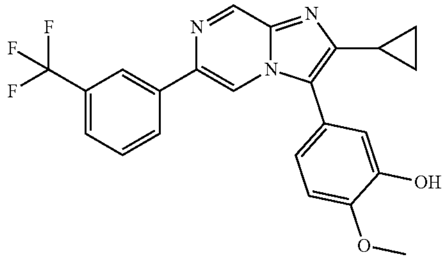 2-methoxy-5-[2-cyclopropyl-6-[3-(trifluoromethyl)phenyl]imidazo[1,2-a]pyrazin-3-yl]phenol | 1B | 7 | 25 mg, 37% | UPLC rt 1.69 min (3 min Run) $MH^+$ 426 |

-continued

| Ex No | Structure | General method | Intermediate No. | Yield Yield | Characterisation |
|---|---|---|---|---|---|
| 14 | 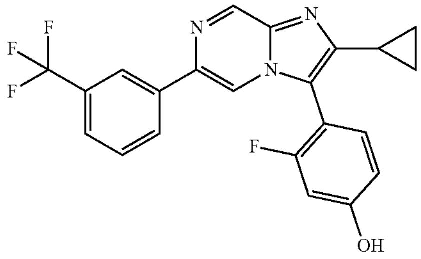 3-fluoro-4-[2-cyclopropyl-6-[3-(trifluoromethyl)phenyl]imidazo[1,2-a]pyrazin-3-yl]phenol | 1B | 7 | 30 mg, 23% | UPLC rt 1.67 min (3 min Run) $MH^+$ 414 |
| 15 | 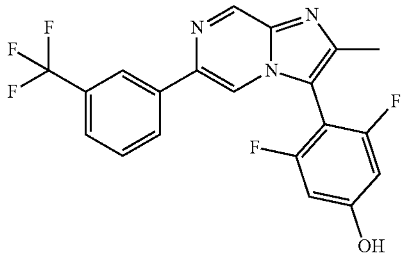 3,5-diluoro-4-[2-methyl-6-[3-(trifluoromethyl)phenyl]imidazo[1,2-a]pyrazin-3-yl]phenol | 1B | 1 | 25 mg, 22% | UPLC rt 1.60 min (3 min Run) $MH^+$ 406 |
| 16 | 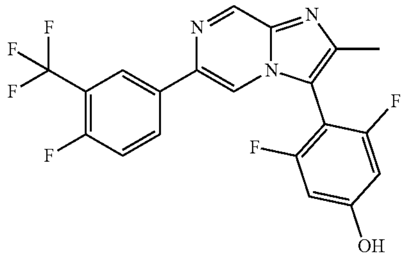 3,5-diluoro-4-[2-methyl-6-[4-fluoro-3-(trifluoromethyl)phenyl]imidazo[1,2-a]pyrazin-3-yl]phenol | 1B | 4 | 12 mg, 11% | UPLC rt 1.85 min (3 min Run) $MH^+$ 424 |
| 17 | 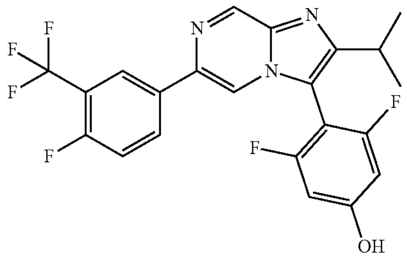 3,5-diluoro-4-[2-(propan-2-yl)-6-[4-fluoro-3-(trifluoromethyl)phenyl]imidazo[1,2-a]pyrazin-3-yl]phenol | 1B | 8 | 14 mg, 12.5% | UPLC rt 3.04 min, $MH^+$ 414 |

-continued

| Ex No | Structure | General method | Intermediate No. | Yield Yield | Characterisation |
|---|---|---|---|---|---|
| 18 | 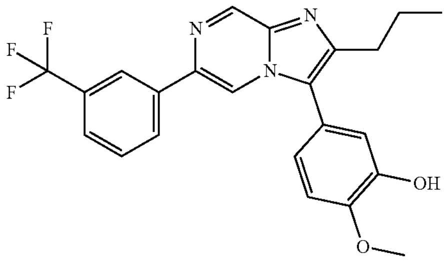 2-methoxy-5-[2-(propan-1-yl)-6-[3-(trifluoromethyl)phenyl]imidazo[1,2-a]pyrazin-3-yl]phenol | 1B | 9 | 10 mg, 14% | UPLC rt 1.89 min (3 min Run) $MH^+$ 428 |
| 19 | 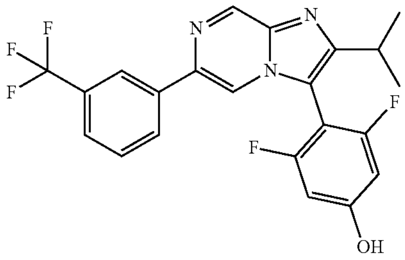 3,5-difluoro-4-[2-(propan-2-yl)-6-[3-(trifluoromethyl)phenyl]imidazo[1,2-a]pyrazin-3-yl]phenol | 1B | 1 | 7 mg, 5% | UPLC rt 2.62 min, $MH^+$ 432 |
| 20 | 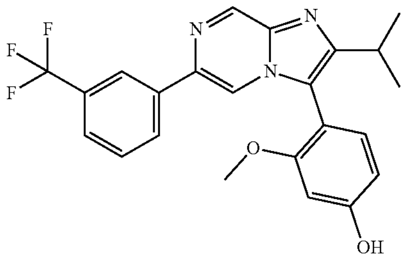 4-(2-isopropyl-6-(3-(trifluoromethyl)phenyl)imidazo[1,2-a]pyrazin-3-yl)-3-methoxyphenol | 1B | 1 | 12 mg, 15% | UPLC rt 3.13 min, $MH^+$ 428 |
| 21 | 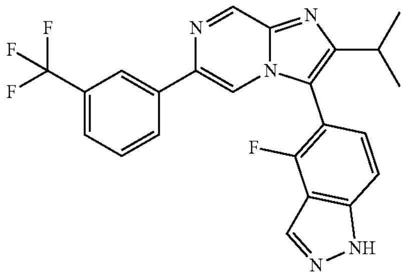 4-fluoro-5-{2-propan-2-yl-6-[3-trifluoromethylphenyl]imidazo[1,2-a]pyrazin-3-yl}-1H-indazole | 2 | 1 | 5 mg, 62% | UPLC rt 3.20 min, $MH^+$ 440 |

-continued

| Ex No | Structure | General method | Intermediate No. | Yield Yield | Characterisation |
|---|---|---|---|---|---|
| 22 | 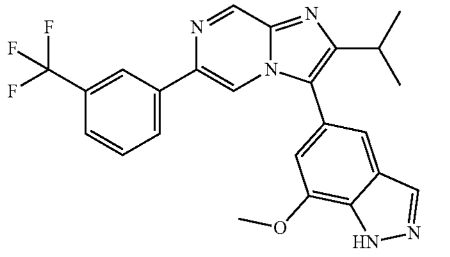 7-methoxy-5-{2-(propan-2-yl)-6-[3-trifluoromethylphenyl]imidazo[1,2-a]pyrazin-3-yl}-1H-indazole | 2 | 1 | 12 mg, 51% | UPLC rt 1.89 min (3 min run) $MH^+$ 452 |
| 23 | 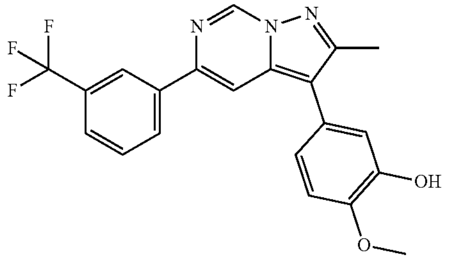 2-methoxy-5-(2-methyl-5-(3-(trifluoromethyl)phenyl)pyrazolo[1,5-c]pyrimidin-3-yl)phenol | 1B | 10 | 60 mg, 54% | UPLC rt 1.92 min (3 min run) $MH^+$ 400 |
| 24 | 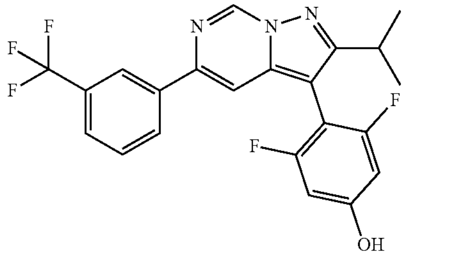 3,5-difluoro-4-(2-isopropyl-5-(3-(trifluoromethyl)phenyl)pyrazolo[1,5-c]pyrimidin-3-yl)phenol | 1B | 11 | 36 mg, 40% | UPLC rt 2.19 min (3 min run) $MH^+$ 434 |
| 25 | 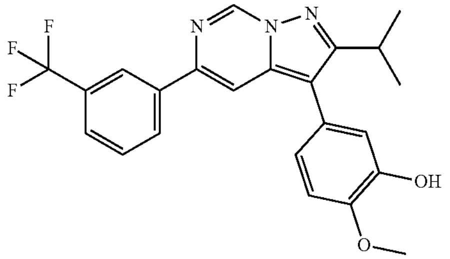 5-(2-isopropyl-5-(3-(trifluoromethyl)phenyl)pyrazolo[1,5-c]pyrimidin-3-yl)-2-methoxyphenol | 1B | 11 | 37 mg, 42% | UPLC rt 3.46 min, $MH^+$ 428 |

-continued

| Ex No | Structure | General method | Intermediate No. | Yield Yield | Characterisation |
|---|---|---|---|---|---|
| 26 | 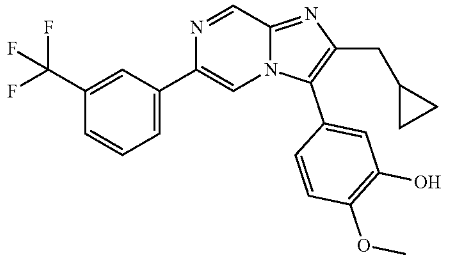 2-methoxy-5-[2-(cyclopropylmethyl)-6-[3-(trifluoromethyl)phenyl]imidazo[1,2-a]pyrazin-3-yl]phenol | 1B | 12 | 20 mg, 25% | UPLC rt 3.17 min, $MH^+$ 440 |
| 27 | 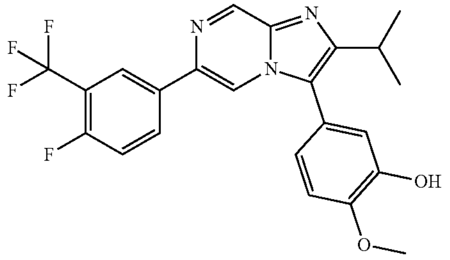 2-methoxy-5-[2-(propan-2-yl)-6-[4-fluoro-3-(trifluoromethyl)phenyl]imidazo[1,2-a]pyrazin-3-yl]phenol | 1B | 8 | 40 mg, 30% | UPLC rt 1.93 min (3 min run) $MH^+$ 446 |
| 28 | 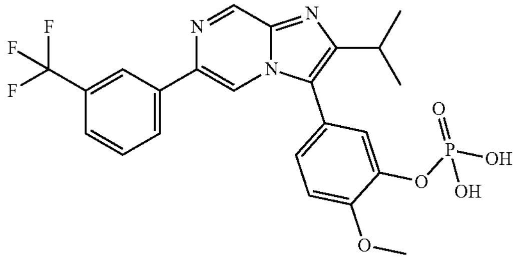 2-methoxy-5-[2-(propan-2-yl)-6-[3-(trifluoromethyl)phenyl]imidazo[1,2-a]pyrazin-3-yl]phenoxyphosphonic acid | 3 | Ex. 1 | 50 mg, 20% | UPLC rt 2.10 min, $MH^+$ 508 |
| 29 | 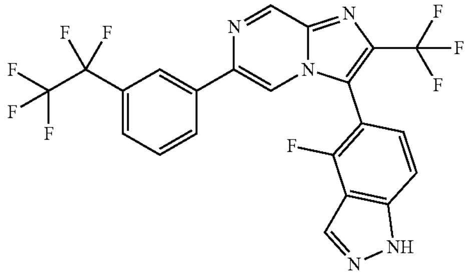 4-fluoro-5-{2-trifluoromethyl-6-[3-(pentafluoroethyl)phenyl]imidazo[1,2-a]pyrazin-3-yl}-1H-indazole | 2 | 13 | 20 mg, 55% | UPLC rt 2.62 min, $MH^+$ 516 |

-continued

| Ex No | Structure | General method | Intermediate No. | Yield Yield | Characterisation |
|---|---|---|---|---|---|
| 30 | 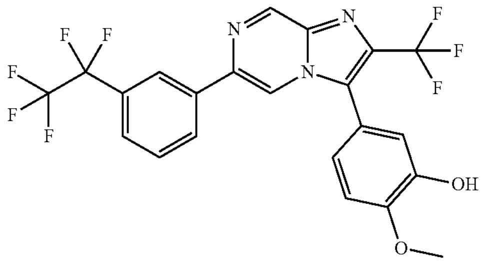 2-methoxy-5-[2-(trifluoromethyl)-6-[3-(pentafluoroethyl)phenyl]imidazo[1,2-a]pyrazin-3-yl]phenol | 1B | 14 | 30 mg, 47% | UPLC rt 3.38 min, $MH^+$ 502 |
| 32 | 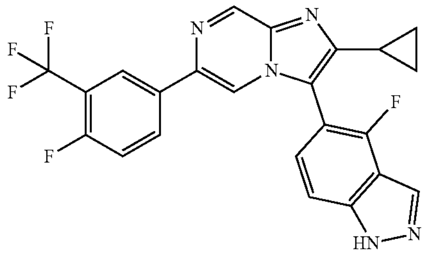 4-fluoro-5-{2-cyclopropyl-6-[4-fluoro-3-(trifluoromethyl)phenyl]imidazo[1,2-a]pyrazin-3-yl}-1H-indazole | 2 | 17 | 125 mg, 21% | UPLC rt 3.09 min, $MH^+$ 456 |
| 33 | 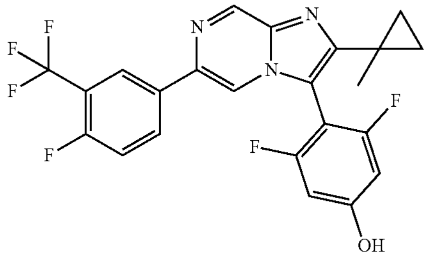 3,5-difluoro-4-[2-(1-methyl-cycloprop-1-yl)-6-[4-fluoro-3-(trifluoromethyl)phenyl]imidazo[1,2-a]pyrazin-3-yl]phenol | 1B | 16 | 3 mg, 10% | UPLC rt 3.36 min, $MH^+$ 464 |
| 34 | 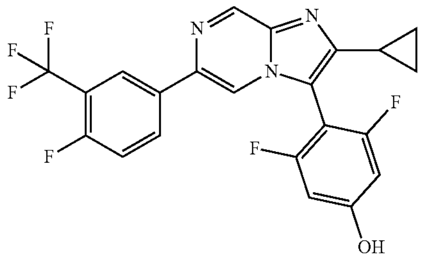 4-(2-cyclopropyl-6-(4-fluoro-3-(trifluoromethyl)phenyl)imidazo[1,2-a]pyrazin-3-yl)-3,5-difluorophenol | 1A | 17 | 165 mg, 30% | UPLC rt 3.14 min, $MH^+$ 450 |

-continued

| Ex No | Structure | General method | Intermediate No. | Yield Yield | Characterisation |
|---|---|---|---|---|---|
| 35 | 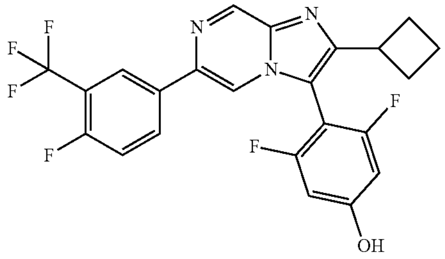 4-(2-cyclobutyl-6-(4-fluoro-3-(trifluoromethyl)phenyl)imidazo[1,2-a]pyrazin-3-yl)-3,5-difluorophenol | 1B | 18 | 72 mg, 64% | UPLC rt 3.37 min, $MH^+$ 464 |
| 36 | 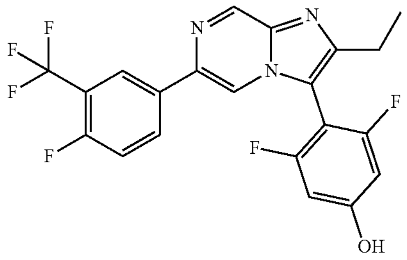 3,5-difluoro-4-[2-ethyl-6-[4-fluoro-3-(trifluoromethyl)phenyl]imidazo[1,2-a]pyrazin-3-yl]phenol | 1B | 19 | 20 mg, 17% | UPLC rt 3.09 min, $MH^+$ 438 |
| 37 | 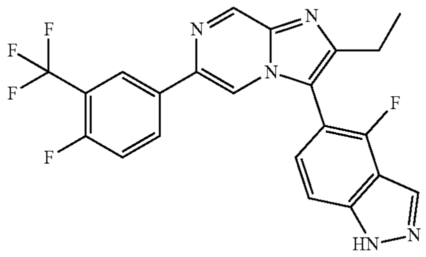 4-fluoro-5-{2-ethyl-6-[4-fluoro-3-(trifluoromethyl)phenyl]imidazo[1,2-a]pyrazin-3-yl}-1H-indazole | 2 | 19 | 12 mg, 65% | UPLC rt 3.02 min, $MH^+$ 444 |
| 38 | 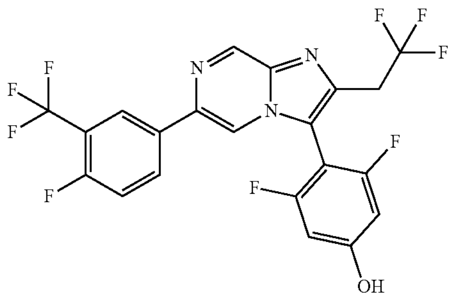 3,5-difluoro-4-(6-(4-fluoro-3-(trifluoromethyl)phenyl)-2-(2,2,2-trifluoroethyl)imidazo[1,2-a]pyrazin-3-yl)phenol | 1B | 20 | 5 mg, 12% | UPLC rt 2.54 min, $MH^+$ 492 |

-continued

| Ex No | Structure | General method | Intermediate No. | Yield Yield | Characterisation |
|---|---|---|---|---|---|
| 39 | 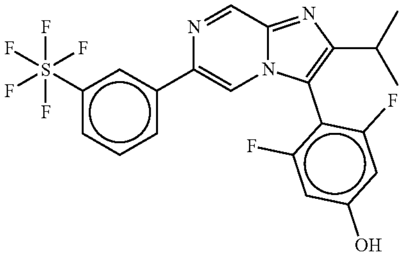 3,5-difluoro-4-[2-(propan-2-yl)-6-[3-(pentafluorosulfanyl)phenyl]imidazo [1,2-a]pyrazin-3-yl]phenol | 4 | 21 | 14 mg, 15% | UPLC rt 3.36 min, $MH^+$ 492 |
| 40 | 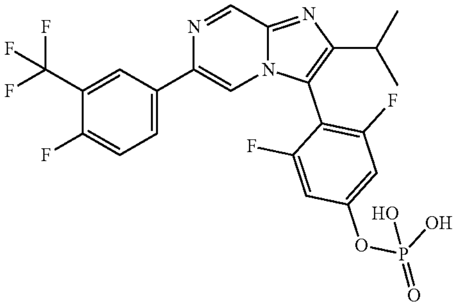 3,5-difluoro-4-{6-[4-fluoro-3-(trifluoromethyl)phenyl]-2-(propan-2-yl)imidazo[1,2-a]pyrazin-3-yl}phenoxyphosphonic acid | 3 | Ex 17 | 13 mg, 28% | UPLC rt 2.27 min, $MH^+$ 532 |
| 41 | 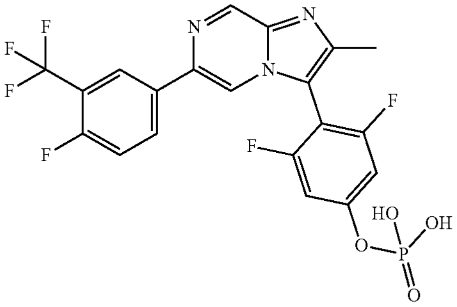 3,5-difluoro-4-{6-[4-fluoro-3-(trifluoromethyl)phenyl]-2-methyl-imidazo[1,2-a]pyrazin-3-yl}phenoxyphosphonic acid | 3 | Ex 16 | 26 mg, 58% | UPLC rt 2.19 min, $MH^+$ 504 |
| 42 | 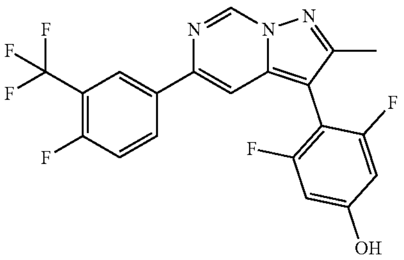 3,5-difluoro-4-(5-(4-fluoro-3-(trifluoromethyl)phenyl)-2-methylpyrazolo[1,5-c]pyrimidin-3-yl)phenol | 1B | 22 | 40 mg, 56% | UPLC rt 3.37 min, $MH^+$ 424 |

-continued

| Ex No | Structure | General method | Intermediate No. | Yield Yield | Characterisation |
|---|---|---|---|---|---|
| 43 | 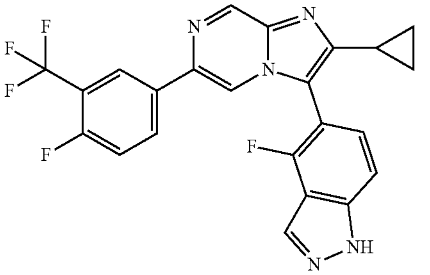 2-cyclopropyl-3-(4-fluoro-1H-indazol-5-yl)-6-(4-fluoro-3-(trifluoromethyl)phenyl)imidazo[1,2-a]pyrazine | 2 | 17 | 5 mg, 55% | UPLC rt 2.73 min, $MH^+$ 456 |
| 44 | 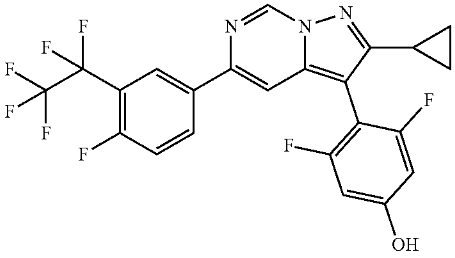 4-[2-Cyclopropyl-6-(4-fluoro-3-pentafluoroethyl-phenyl)-imidazo[1,2-a]pyrazin-3-yl]-3,5-difluoro-phenol | 2 | 23 | 7 mg, 14% | UPLC rt 2.66 min, $MH^+$ 500 |
| 45 | 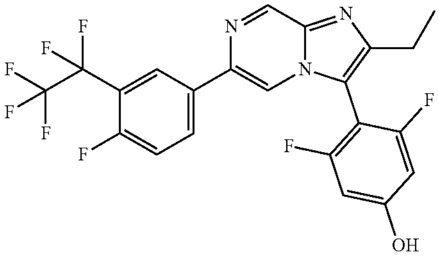 4-{2-ethyl-6-[4-fluoro-3-(1,1,2,2,2-pentafluoroethyl)phenyl]imidazo[1,2-a]pyrazin-3-yl}-3,5-difluorophenol | 1B | 24 | 6 mg, 9% | UPLC rt 3.37 min, $MH^+$ 488 |
| 46 | 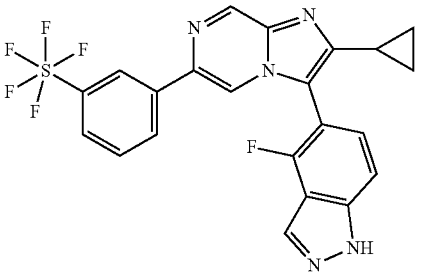 2-cyclopropyl-3-(4-fluoro-1H-indazol-5-yl)-6-(3-(pentafluoro-λ6-sulfaneyl)phenyl)imidazo[1,2-a]pyrazine | 4B | 25 | 9 mg, 55% | UPLC rt 3.16 min, $MH^+$ 494 |

-continued

| Ex No | Structure | General method | Intermediate No. | Yield Yield | Characterisation |
|---|---|---|---|---|---|
| 47 | 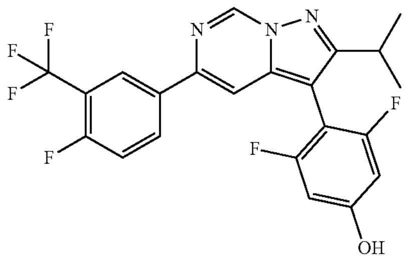 3,5-difluoro-4-(5-(4-fluoro-3-(trifluoromethyl)phenyl)-2-(propan-2-yl)-pyrazolo[1,5-c]pyrimidin-3-yl)phenol | 1B | 26 | 10 mg, 17% | UPLC rt 3.57 min, $[M - H]^-$ 450 |
| 48 | 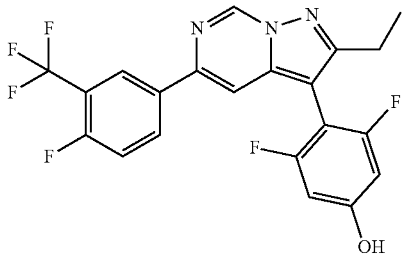 4-(2-ethyl-5-(4-fluoro-3-(trifluoromethyl)phenyl)pyrazolo[1,5-c]pyrimidin-3-yl)-3,5-difluorophenol | 1B | 27 | 7 mg, 12% | UPLC rt 3.43 min, $MH^+$ 438 |
| 49 | 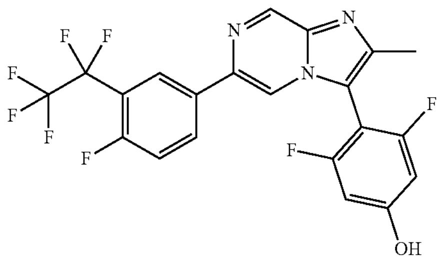 3,5-difluoro-4-[2-methyl-6-[3-(pentafluoroethyl)phenyl] imidazo[1,2-a]pyrazin-3-yl]phenol | 1B | 28 | 20 mg, 24% | UPLC rt 3.17 min, $MH^+$ 456 |
| 50 | 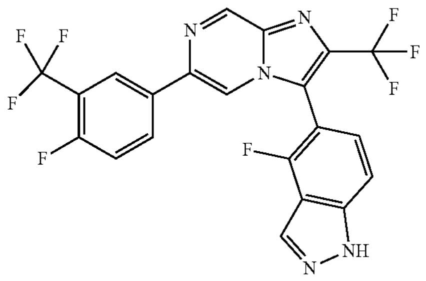 3-(4-Fluoro-1H-indazol-5-yl)-6-(4-fluoro-3-trifluoromethyl phenyl)-2-trifluoromethyl-imidazo[1,2-a]pyrazine | 2 | 29 | 81 mg, 27% | UPLC rt 3.22 min, $[M - H]^-$ 482 |

-continued

| Ex No | Structure | General method | Intermediate No. | Yield Yield | Characterisation |
|---|---|---|---|---|---|
| 51 | 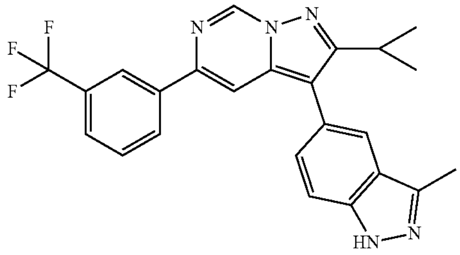 2-Isopropyl-3-(3-methyl-1H-indazol-5-yl)-6-(3-trifluoromethyl-phenyl)-imidazo[1,2-a]pyrazine | 3A | 1 | 33 mg, 39% | UPLC rt 2.02 min (3 min Run) $MH^+$ 436 |
| 52 | 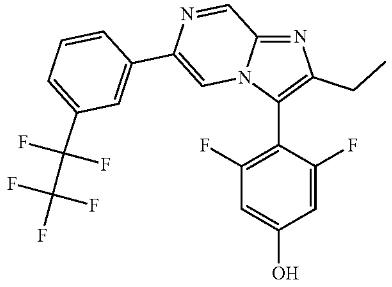 4-[2-Ethyl-6-(3-pentafluoroethyl-phenyl)-imidazo[1,2-a]pyrazin-3-yl]-3,5-difluoro-phenol | 1A | 3 | 75 mg, 67% | HPLC rt 11.49 min, $MH^-$ 468 |
| 53 | 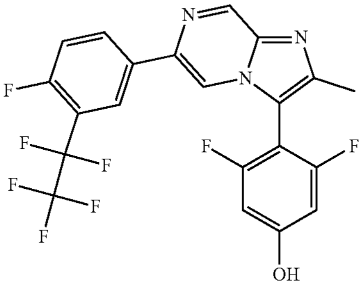 3,5-Difluoro-4-[6-(4-fluoro-3-pentafluoroethyl-phenyl)-2-methyl-imidazo[1,2-a]pyrazin-3-yl]-phenol | 2 | 31 | 7 mg, 10.6% | UPLC rt 3.16 min, $MH^+$ 474 |
| 54 | 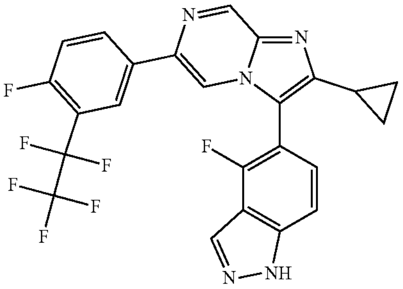 2-Cyclopropyl-3-(4-fluoro-1H-indazol-5-yl)-6-(4-fluoro-3-pentafluoroethyl-phenyl)-imidazo[1,2-a]pyrazine | 3A | 23 | 5 mg, 6% | UPLC rt 3.23 min, $MH^+$ 506 |

-continued

| Ex No | Structure | General method | Intermediate No. | Yield Yield | Characterisation |
|---|---|---|---|---|---|
| 55 | 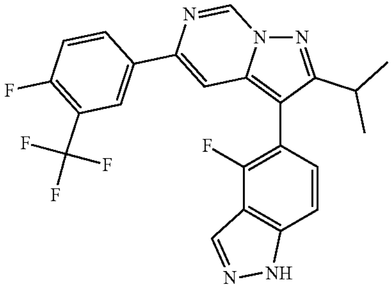 4-Fluoro-5-[5-(4-fluoro-3-trifluoro methyl-phenyl)-2-isopropylpyrazolo[1,5-a]pyridin-3-yl]-1H-indazole | 3C | 32 | 15 mg, 17.75% | UPLC rt 3.32 min, $MH^-$ 455 |
| 56 | 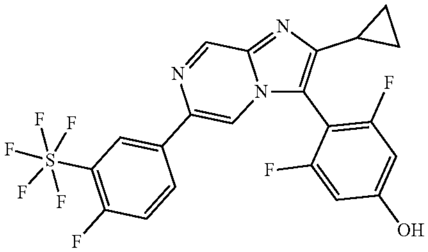 4-[2-Cyclopropyl-6-(4-fluoro-3-pentafluorosulfanyl-phenyl)-imidazo[1,2-a]pyrazin-3-yl]-3,5-difluoro-phenol | 2 | 33 | 3 mg, 2.81% | UPLC rt 1.82 min (3 min Run), $MH^+$ 508 |
| 57 | 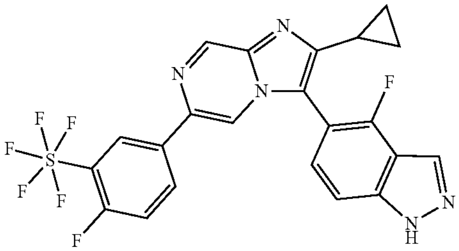 2-Cyclopropyl-3-(4-fluoro-1H-indazol-5-yl)-6-(4-fluoro-3-pentafluorosulfanyl-phenyl)-imidazo[1,2-a]pyrazine | 3A | 33 | 11 mg, 16.54% | UPLC rt 3.27 min, $MH^+$ 514 |
| 58 | 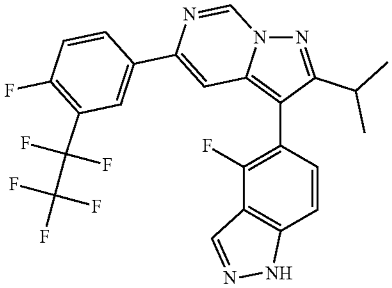 3-(4-Fluoro-1H-indazol-5-yl)-5-(4-fluoro-3-pentafluoroethyl-phenyl)-2-isopropyl-pyrazolo[1,5-c]pyrimidine | 3B | 34 | 22 mg, 65.05% | UPLC rt 1.92 min (3 min Run), $MH^+$ 508 |

-continued

| Ex No | Structure | General method | Intermediate No. | Yield Yield | Characterisation |
|---|---|---|---|---|---|
| 59 | 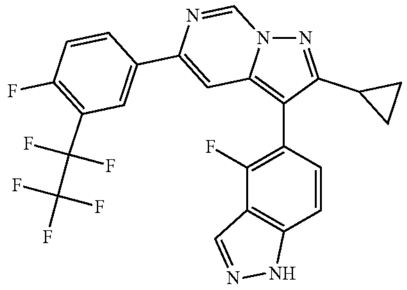 2-Cyclopropyl-3-(4-fluoro-1H-indazol-5-yl)-5-(4-fluoro-3-pentafluoroethyl-phenyl)-pyrazolo[1,5-c]pyrimidine | 3B | 35 | 17 mg, 23.07% | UPLC rt 1.92 min (3 min Run), $MH^-$ 504 |
| 60 | 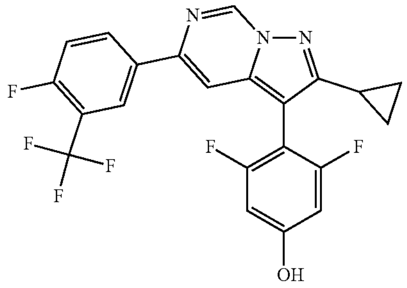 4-[2-Cyclopropyl-5-(4-fluoro-3-trifluoromethyl-phenyl)-pyrazolo[1,5-c]pyrimidin-3-yl]-3,5-difluoro-phenol | 1B | 35 | 34 mg, 43.24% | UPLC rt 3.57 min, $MH^-$ 448 |
| 61 | 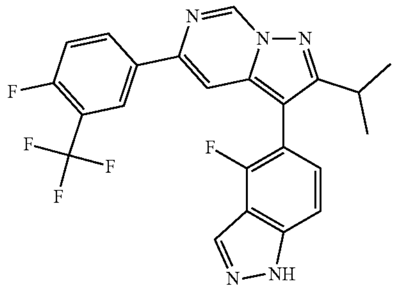 3-(4-Fluoro-1H-indazol-5-yl)-5-(4-fluoro-3-trifluoromethyl-phenyl)-2-isopropyl-pyrazolo[1,5-c]pyrimidine | 3B | 36 | 33 mg, 39.03% | UPLC rt 3.58 min, $MH^-$ 456 |

-continued

| Ex No | Structure | General method | Intermediate No. | Yield Yield | Characterisation |
|---|---|---|---|---|---|
| 62 | 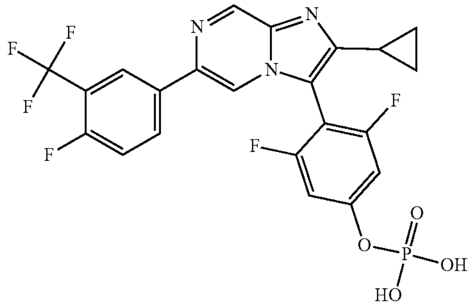 Phosphoric acid mono-{4-[2-cyclopropyl-6-(4-fluoro-3-trifluoromethyl-phenyl)-imidazo[1,2-a]pyrazin-3-yl]-3,5-difluoro-phenyl} ester | 4 | Example 34 | 32 mg, 18-22% | UPLC rt 2.08 min, $MH^+$ 530 |
| 63 | 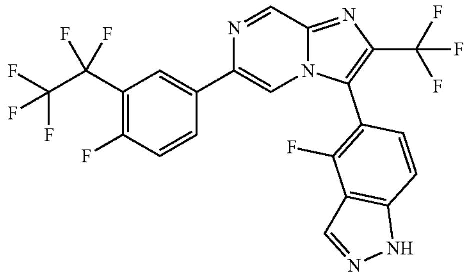 3-(4-Fluoro-1H-indazol-5-yl)-6-(4-fluoro-3-pentafluoroethyl-phenyl)-2-trifluoromethyl-imidazo[1,2-a]pyrazine | 3A | 37 | 150 mg, 35-40% | UPLC rt 1.97 min (3 min Run), $MH^+$ 534 |
| 64 | 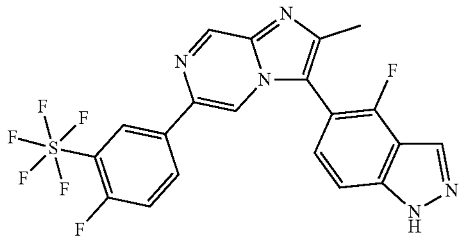 3-(4-Fluoro-1H-indazol-5-yl)-6-(4-fluoro-3-pentafluorosulfanyl-phenyl)-2-methyl-imidazo[1,2-a]pyrazine | 3D | 38 | 12 mg, 10.81% | UPLC rt 3.03 min, $MH^-$ 486 |
| 65 | 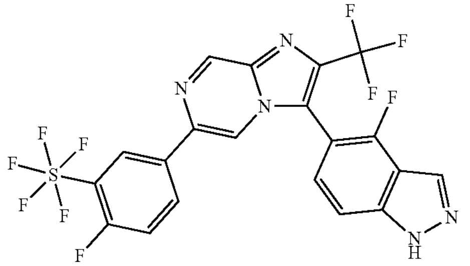 3-(4-Fluoro-1H-indazol-5-yl)-6-(4-fluoro-3-pentafluorosulfanyl-phenyl)-2-trifluoromethyl-imidazo[1,2-a]pyrazine | 3A | 39 | 10 mg, 6.79% | UPLC rt 3.26 min, $MH^-$ 540 |

-continued

| Ex No | Structure | General method | Intermediate No. | Yield Yield | Characterisation |
|---|---|---|---|---|---|
| 66 | 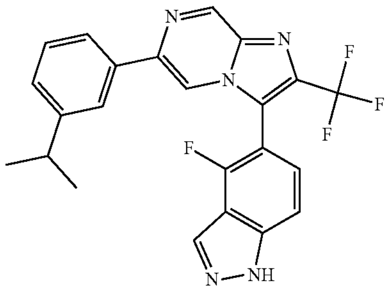<br>3-(4-Fluoro-1H-indazol-5-yl)-6-(3-isopropyl-phenyl)-2-trifluoromethyl-imidazo[1,2-a]pyrazine | 3A | 40 | 46 mg, 45.63% | UPLC rt 2.59 min, $MH^+$ 440 |
| 67 | 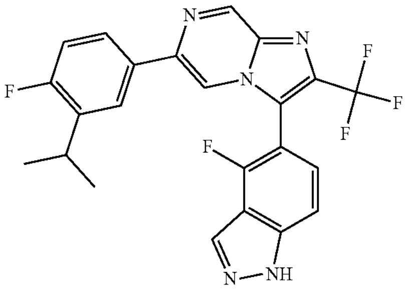<br>3-(4-Fluoro-1H-indazol-5-yl)-6-(4-fluoro-3-isopropyl-phenyl)-2-trifluoromethyl-imidazo[1,2-a]pyrazine | 3A | 41 | 50 mg, 25-30% | UPLC rt 2.10 min (3 min Run), $MH^+$ 458 |
| 68 | 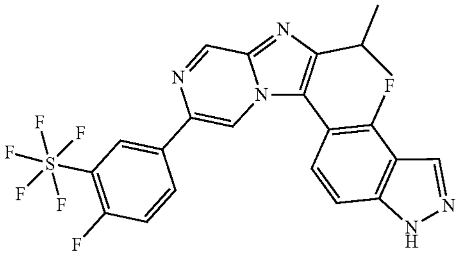<br>3-(4-Fluoro-1H-indazol-5-yl)-6-(4-fluoro-3-pentafluorothio-phenyl)-2-isopropyl-imidazo[1,2-a]pyrazine | 3D | 42 | 35 mg, 21.54% | UPLC rt 2.66 min, $MH^+$ 516 |
| 69 | 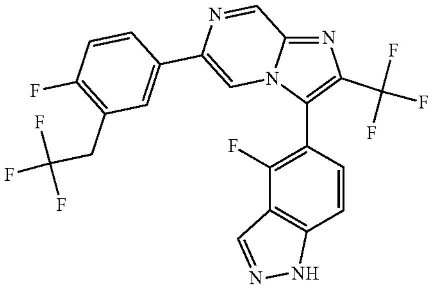<br>3-(4-Fluoro-1H-indazol-5-yl)-6-[4-fluoro-3-(2,2,2-trifluoro-ethyl)-phenyl]-2-trifluoromethyl-imidazo[1,2-a]pyrazine | 3A | 43 | 3 mg, 2.34% | UPLC rt 1.75 min (3 min Run), $MH^+$ 498 |

-continued

| Ex No | Structure | General method | Intermediate No. | Yield Yield | Characterisation |
|---|---|---|---|---|---|
| 70 | 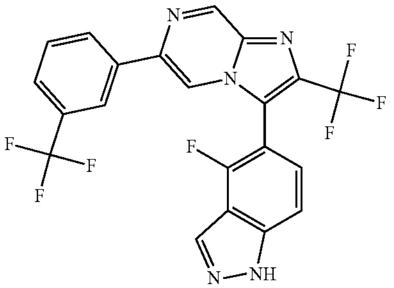 3-(4-Fluoro-1H-indazol-5-yl)-2-trifluoromethyl-6-(3-trifluoromethyl-phenyl)-imidazo[1,2-a]pyrazine | 3A | 44 | 35 mg, 47.48% | UPLC rt 1.76 min (3 min Run), $MH^+$ 466 |
| 71 | 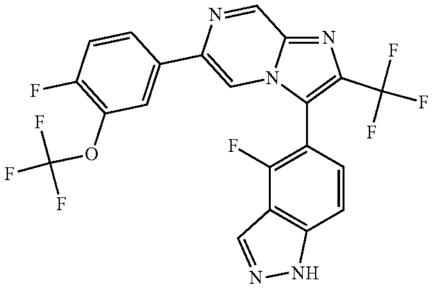 3-(4-Fluoro-1H-indazol-5-yl)-6-(4-fluoro-3-trifluoromethoxy-phenyl)-2-trifluoromethyl-imidazo[1,2-a]pyrazine | 3A | 45 | 35 mg, 25.54% | UPLC rt 1.79 min (3 min Run), $MH^+$ 500 |
| 72 | 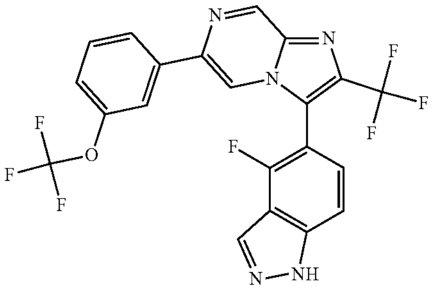 3-(4-Fluoro-1H-indazol-5-yl)-6-(3-trifluoromethoxy-phenyl)-2-trifluoromethyl-imidazo[1,2-a]pyrazine | 3A | 46 | 80 mg, 37.56% | UPLC rt 1.78 min (3 min Run), $MH^+$ 482 |
| 73 | 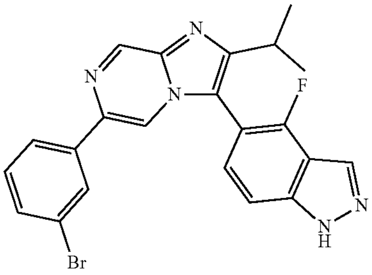 6-(3-Bromo-phenyl)-3-(4-fluoro-1H-indazol-5-yl)-2-isopropyl-imidazo[1,2-a]pyrazine | 3D | 47 | 10 mg, 14.82% | UPLC rt 1.82 min (3 min Run), $MH^+$ 450 |

-continued

| Ex No | Structure | General method | Intermediate No. | Yield Yield | Characterisation |
|---|---|---|---|---|---|
| 74 | 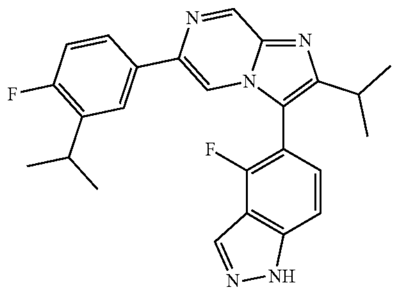 3-(4-Fluoro-1H-indazol-5-yl)-6-(4-fluoro-3-isopropyl-phenyl)-2-isopropyl-imidazo[1,2-a]pyrazine | 3A | 48 | 25 mg, 14.92% | UPLC rt 2.73 min, $MH^+$ 432 |
| 75 | 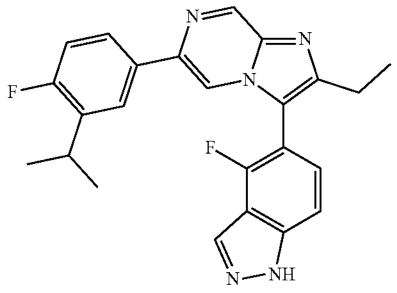 2-Ethyl-3-(4-fluoro-1H-indazol-5-yl)-6-(4-fluoro-3-isopropyl-phenyl)-imidazo[1,2-a]pyrazine | 3A | 49 | 50 mg, 13.79% | HPLC rt 13.19 min, $MH^+$ 418 |
| 76 | 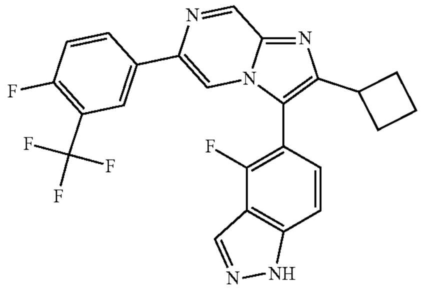 2-Cyclobutyl-3-(4-fluoro-1H-indazol-5-yl)-6-(4-fluoro-3-trifluoromethyl-phenyl)-imidazo[1,2-a]pyrazine | 3A | 50 | 50 mg, 34.65% | UPLC rt 1.93 min (3 min Run), $MH^+$ 470 |
| 77 | 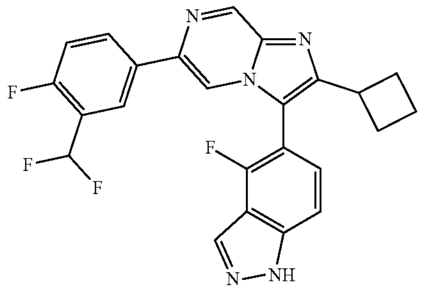 2-Cyclobutyl-3-(4-fluoro-1H-indazol-5-yl)-6-(4-fluoro-3-isopropyl-phenyl)-imidazo[1,2-a]pyrazine | 3A | 51 | 23 mg, 27.33% | HPLC rt 8.68 min, $MH^+$ 444 |

-continued

| Ex No | Structure | General method | Intermediate No. | Yield Yield | Characterisation |
|---|---|---|---|---|---|
| 78 | 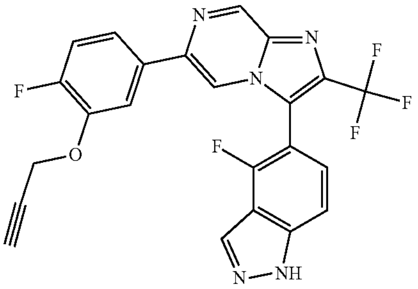 3-(4-Fluoro-1H-indazol-5-yl)-6-(4-fluoro-3-prop-2-ynyloxy-phenyl)-2-trifluoromethyl-imidazo[1,2-a]pyrazine | 3A | 52 | 10 mg, 5.89% | UPLC rt 1.81 min (3 min Run), $MH^+$ 470 |
| 79 | 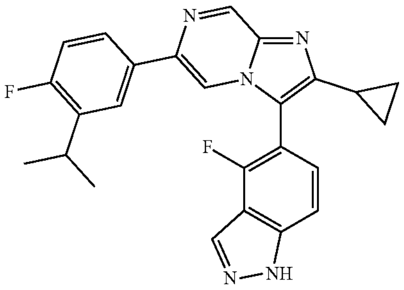 2-Cyclopropyl-3-(4-fluoro-1H-indazol-5-yl)-6-(4-fluoro-3-isopropyl-phenyl)-imidazo[1,2-a]pyrazine | 3A | 53 | 25 mg, 19.91% | UPLC rt 1.94 min (3 min Run), $MH^+$ 430 |
| 80 | 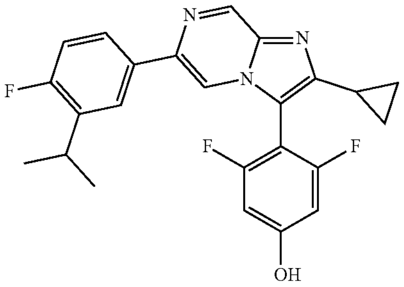 4-[2-Cyclopropyl-6-(4-fluoro-3-isopropyl-phenyl)-imidazo[1,2-a]pyrazin-3-yl]-3,5-difluoro-phenol | 1A | 53 | 3 mg, 4.32% | UPLC rt 2.78 min, $MH^+$ 424 |
| 81 | 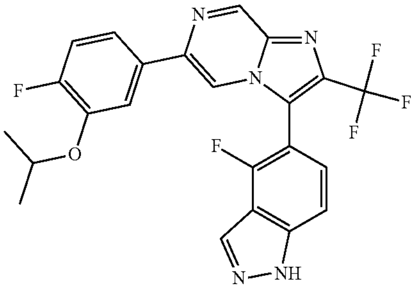 3-(4-Fluoro-1H-indazol-5-yl)-6-(4-fluoro-3-isopropoxy-phenyl)-2-trifluoromethyl-imidazo[1,2-a]pyrazine | 3A | 54 | 80 mg, 40.96% | UPLC rt 2.75 min, $MH^+$ 474 |

-continued

| Ex No | Structure | General method | Intermediate No. | Yield Yield | Characterisation |
|---|---|---|---|---|---|
| 82 | 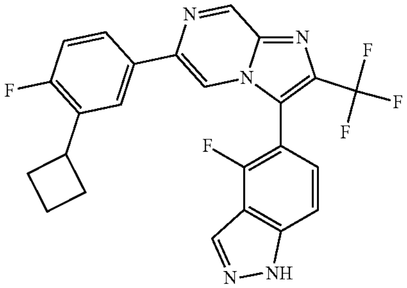 6-(3-Cyclobutyl-4-fluoro-phenyl)-3-(4-fluoro-1H-indazol-5-yl)-2-trifluoromethyl-imidazo[1,2-a]pyrazine | 3A | 55 | 25 mg, 18.42% | UPLC rt 1.99 min (3 min Run), $MH^+$ 470 |
| 83 | 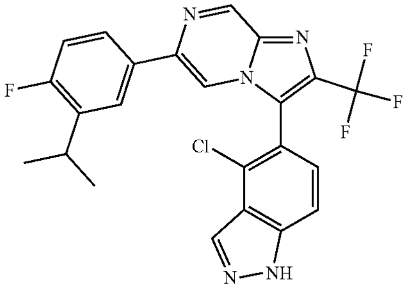 3-(4-Chloro-1H-indazol-5-yl)-6-(4-fluoro-3-isopropyl-phenyl)-2-trifluoromethyl-imidazo[1,2-a]pyrazine | 3A | 56 | 13 mg, 35.17% | UPLC rt 1.97 min (3 min Run), $MH^+$ 474 |
| 84 | 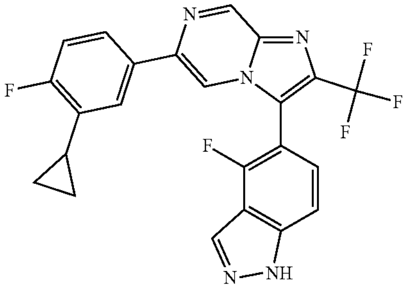 6-(3-Cyclopropyl-4-fluoro-phenyl)-3-(4-fluoro-1H-indazol-5-yl)-2-trifluoromethyl-imidazo[1,2-a]pyrazine | 3A | 57 | 25 mg, 24.68% | UPLC rt 1.90 min (3 min Run), $MH^+$ 456 |
| 85 | 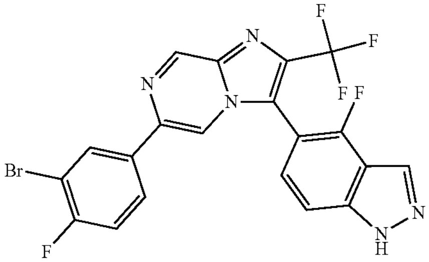 6-(3-Bromo-4-fluoro-phenyl)-3-(4-fluoro-1H-indazol-5-yl)-2-trifluoromethyl-imidazo[1,2-a]pyrazine | 3D | 58 | 10 mg, 9.75% | UPLC rt 1.91 min (3 min Run), $MH^+$ 494 |

-continued

| Ex No | Structure | General method | Intermediate No. | Yield Yield | Characterisation |
|---|---|---|---|---|---|
| 86 | 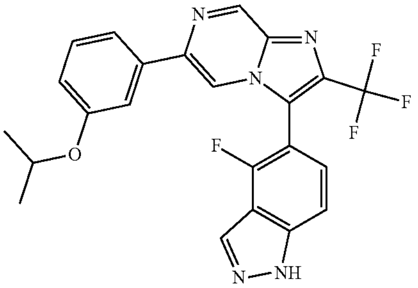 3-(4-Fluoro-1H-indazol-5-yl)-6-(3-isopropoxy-phenyl)-2-trifluoromethyl-imidazo[1,2-a a]pyrazine | 3A | 59 | 50 mg, 35.9% | UPLC rt 2.73 min, $MH^+$ 456 |
| 87 | 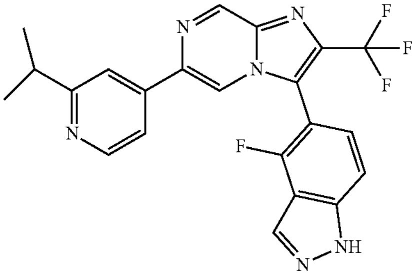 3-(4-Fluoro-1H-indazol-5-yl)-6-(2-isopropyl-pyridin-4-yl)-2-trifluoromethyl-imidazo[1,2-a]pyrazine | 3A | 60 | 10 mg, 12% | UPLC rt 2.86 min, $MH^+$ 441 |
| 88 | 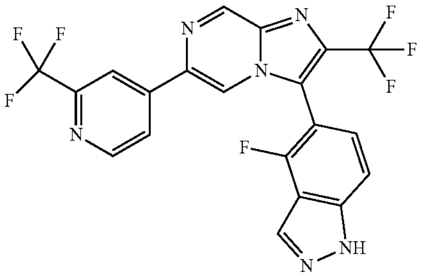 3-(4-Fluoro-1H-indazol-5-yl)-2-trifluoromethyl-6-(2-trifluoromethyl-pyridin-4-yl)-imidazo[1,2-a]pyrazine | 3A | 61 | 60 mg, 34.52% | UPLC rt 1.70 min (3 min Run), $MH^-$ 465 |
| 89 | 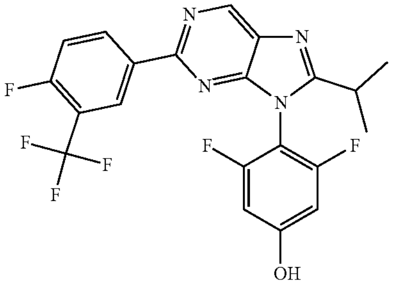 3,5-Difluoro-4-[2-(4-fluoro-3-trifluoromethyl-phenyl)-8-isopropyl-purin-9-yl]-phenol | 5 | 62 | 30 mg, 52.82% | UPLC rt 2.63 min, $MH^+$ 453 |

In Vitro Testing

The routine biological assays using adult or juvenile worms and cytotoxicity assays using MRC-5 cells have been disclosed previously in Mansour, N. R., et al. (2016). "*High Throughput Screening Identifies Novel Lead Compounds with Activity against Larval, Juvenile and Schistosoma mansoni* PLoS Negl Trap Dis 10(4): e0004659. Cytotoxicity assays using the HepG2 cell line were carried out as described in Molecular Diversity (2015) 19, 251-261.

(a) *S. mansoni* adult worms (b) *S. mansoni* juvenile worms (c) *S. haemotobium* adult worms (d) Cytotoxicity against human MRC-5 cell line (e) Cytotoxicity against human HepG2 cell lines The compounds of Examples 1-90 exhibit one or more of the following compared to the compound disclosed in PLoS Negl Trap Dis 10(4): e0004659

| Example Number | (a) Adult (μM) | (b) Juvenile (μM) | (c) *S. haemotobium* (μM) | (d) Cytotox MRC-5 (μM) | (e) Cytotox HepG2 (μM) |
|---|---|---|---|---|---|
| LSHTM-1945 | 4.9 | 5.7 | | 40.1 | |
| 1 | 0.058 | 0.013 | <0.195 | 21.8 | >11.1 |
| 2 | 0.047 | 0.019 | | | 10.4 |
| 3 | <0.049 | 0.13 | | | 9.2 |
| 4 | 0.49 | 1.42 | | | |
| 5 | 0.52 | 1.27 | | | |
| 6 | 0.29 | 0.48 | | 15.8 | |
| 7 | 0.09 | 0.082 | | >50 | >30 |
| 8 | 0.100 | 0.086 | <1.56 | 17.3 | 18.7 |
| 9 | 0.076 | 0.079 | | 13.7 | 9 |
| 10 | <0.78 | 0.53 | | 14.4 | >11.1 |
| 11 | | 0.49 | | | |
| 12 | <0.049 | 0.25 | | | |
| 13 | 0.072 | 0.063 | | | |
| 14 | | 0.23 | | | |
| 15 | | 0.17 | | | 8.4 |
| 16 | 0.12 | 0.22 | 0.04 | | 7.6 |
| 17 | 0.044 | 0.026 | 0.023 | | 7.1 |
| 18 | | 0.29 | | | |
| 19 | 0.042 | 0.090 | | | 7.5 |
| 20 | 0.92 | 1.04 | | | |
| 21 | 0.037 | 0.051 | | | 15.1 |
| 22 | 0.43 | 0.53 | 0.15 | | |
| 23 | | 0.79 | | | |
| 24 | 0.022 | <0.012 | | | 8.4 |
| 25 | | 0.11 | | | |
| 26 | | 0.22 | | | |
| 27 | <0.049 | 0.149 | | | |
| 28 | | 0.183 | | | 19.2 |
| 29 | 0.030 | 0.028 | | | 8.9 |
| 30 | 0.021 | <0.012 | | | 11.1 |
| 31 | | 0.10 | | | |
| 32 | 0.063 | | | | 16.1 |
| 33 | 0.056 | 0.080 | | | 7.9 |
| 34 | 0.069 | 0.088 | | | 8.9 |
| 35 | 0.059 | 0.073 | | | 5.7 |
| 36 | 0.053 | 0.051 | | | 8.3 |
| 37 | | 0.11 | | | 13.1 |
| 38 | | 0.14 | | | |
| 39 | 0.024 | <0.012 | | | 6.6 |
| 40 | 0.027 | 0.025 | | | 6.5 |
| 41 | | 0.10 | | | 6.8 |
| 42 | | 0.11 | | | |
| 43 | | 0.11 | | | |
| 44 | 0.010 | 0.024 | | | 9.4 |
| 45 | | 0.021 | | | |
| 46 | | 0.036 | | | 20.7 |
| 47 | 0.022 | 0.027 | | | 8.9 |
| 48 | 0.011 | 0.032 | | | 9.8 |
| 49 | 0.034 | 0.035 | | | 9.3 |
| 50 | | 0.060 | | | |
| 51 | | 0.83 | | | 10.3 |

-continued

| Example Number | (a) Adult (μM) | (b) Juvenile (μM) | (c) *S. haemotobium* (μM) | (d) Cytotox MRC-5 (μM) | (e) Cytotox HepG2 (μM) |
|---|---|---|---|---|---|
| 52 | <0.012 | 0.010 | | | 8.0 |
| 53 | 0.019 | 0.020 | | | 8.8 |
| 54 | 0.023 | 0.037 | | | |
| 55 | 0.028 | 0.022 | | | 11.1 |
| 56 | 0.019 | 0.020 | | | 10.1 |
| 57 | 0.017 | 0.030 | | | 14.8 |
| 58 | 0.031 | 0.02 | | | 10.8 |
| 59 | 0.066 | 0.036 | | | |
| 60 | 0.017 | 0.021 | | | |
| 61 | 0.037 | 0.060 | | | |
| 62 | | 0.0037 | | | 14.8 |
| 63 | 0.011 | 0.010 | <0.006 | | 11.7 |
| 64 | 0.026 | 0.077 | | | |
| 65 | 0.044 | 0.011 | | | 11.1 |
| 66 | 0.0052 | 0.0052 | | | 12.9 |
| 67 | 0.002 | 0.002 | | | 17.0 |
| 68 | 0.011 | 0.010 | | | |
| 69 | 0.012 | 0.010 | | | 5.3 |
| 70 | 0.025 | 0.041 | | | |
| 71 | 0.014 | 0.021 | | | 12.2 |
| 72 | 0.021 | 0.023 | | | 9.7 |
| 73 | 0.036 | 0.027 | | | |
| 74 | 0.004 | 0.005 | | | 11.0 |
| 75 | 0.004 | 0.005 | | | 11.3 |
| 76 | 0.037 | 0.036 | | | |
| 77 | 0.007 | 0.004 | | | 10.8 |
| 78 | 0.010 | 0.021 | | | |
| 79 | 0.005 | 0.005 | | | 15.7 |
| 80 | 0.004 | 0.005 | | | |
| 81 | 0.011 | 0.012 | | | 9.2 |
| 82 | 0.045 | 0.059 | | | 6.1 |
| 83 | <0.012 | 0.015 | | | 6.6 |
| 84 | 0.012 | 0.019 | | | 10.5 |
| 85 | 0.048 | 0.007 | | | |
| 86 | 0.017 | 0.026 | | | 13.2 |
| 87 | 0.037 | 0.091 | | | 9.5 |
| 88 | 0.116 | 0.140 | | | 7.0 |
| 89 | 0.071 | 0.128 | | | 4.8 |
| 90 | 0.077 | 0.468 | | | 9.3 |

Preferred compounds of the invention are those which by inspection, appear to kill or significantly damage the worms at lower concentrations within the $IC_{50}$ range shown above. For example, preferred are compounds with $IC_{50}$ values against both adult and juvenile worms below 0.5 μM; More preferred compounds are those with $IC_{50}$ values against both adult and juvenile worms below 0.1 μM;

In Vivo Testing

Infection of Mice and Worm Recovery

Methods for the subcutaneous infection of mice and subsequent worm recovery were as described in Mansour et al (2016) except that infection was with 150 cercariae and the perfusion medium was citrate saline (0.9% sodium chloride, 1.5% tri-sodium citrate). Perfusion was carried out 8 days (adult infections) or 15 days (juvenile infections) after treatment. Perfuseate was collected into 30 mL universal tubes. RBC (Red Blood Cells) were removed by allowing the perfuseate to settle for 10 min, removal of most of the supernatant and washing once as above with 10 mL perfusion medium. A drop of dilute aqueous saponin solution was added to lyse any remaining RBC and the worm suspension poured into a grid-marked small petri dish. The tube was rinsed out into the petri dish and examined for any remaining worms. Worms were counted using a dissecting microscope. The mouse livers removed after perfusion were squashed between two thick glass plates and examined visually and any remaining worms added to those counted as above.

Drug Treatment

For testing efficacy against the juvenile worms, treatment was on day 25 post infection and for testing against the adult worms on day 42 post infection. Drugs were suspended in 7% Tween-80/3% Ethanol/double distilled water and drug dispersal was facilitated by vortexing and using a sonicating water bath (Formulation F1). Alternatively, drugs were suspended in 10% DMSO, 90% double distilled water containing 50 mM $Na_2HPO_4$ with 0.5% Tween-80 by first dissolving or suspending the drug in DMSO then adding the DMSO solution/suspension to the aqueous solution (Formulation F2). In a further set of conditions, drugs were first dissolved in DMSO, then diluted with corn oil to give a 5% DMSO+drug solution/suspension (Formulation F3)

The drug solution/suspensions were given by oral gavage at the rate of 10 ml/kg. Positive controls (artemether for juvenile worms and praziquantel for adult worms) were used in each experiment. Oral artemether at 400 mg/kg single dose is equally or more effective in mice against juvenile compared with adult *S. mansoni* (Am J Trap Med Hyg. 2010 January; 82(1):112-4. *Activity of artemether and mefloquine against juvenile and adult Schistosoma mansoni in athymic and immunocompetent NMRI mice*. Keiser J1, Vargas M, Doenhoff M J) and so is a useful positive control for drug testing against juvenile stages in the murine screen.

| Age of infection (worms) | Compound Example No (Formulation) | Oral Dose | Mean worm recovery | Percent worm reduction | P value |
|---|---|---|---|---|---|
| Adult | Negative control | N/A | 38.8 ± 5.4 | N/A | N/A |
| | Positive control Praziquantel (F1) | 400 mg/kg | 2.3 ± 1.7 | 94 | <0.0001 |
| | 17 (F1) | 200 mg/kg | 0.3 ± 0.8 | 99 | <0.0001 |
| Adult | Negative control | N/A | 33.8 ± 4.1 | N/A | |
| | Positive control Praziquantel (F1) | 50 mg/kg | 29.8 ± 8.4 | 13 | 0.3 |
| | Positive control Praziquantel (F1) | 100 mg/kg | 12.2 ± 6.3 | 64 | 0.0002 |
| | Positive control Praziquantel (F1) | 400 mg/kg | 2.6 ± 1.5 | 92 | <0.0001 |
| | 50 (F1) | 12.5 mg/kg | 0.2 | 99 | <0.0001 |
| | 50 (F1) | 6.25 mg/kg | 7.4 ± 8.1 | 78 | 0.0002 |
| Juvenile | Negative control | | 33.0 ± 7.2 | — | |
| | Positive control, Artemether (F1) | 400 mg/kg | 8.2 ± 4.1 | 75 | 0.0002 |
| | 17 (F1) | 200 mg/kg | 5.2 ± 3.1 | 84 | <0.0001 |
| | 17 (F1) | 50 mg/kg | 20.6 ± 8.5 | 38 | 0.038 |
| | 34 (F1) | 50 mg/kg | 24.8 ± 7.4 | 25 | 0.11 |
| | 2 (F1) | 50 mg/kg | 4.0 ± 4.1 | 88 | <0.0001 |
| | 32 (F1) | 50 mg/kg | 29.0 ± 7.9 | 12 | 0.43 |
| Juvenile | Negative control | N/A | 33.2 ± 9.09 | N/A | N/A |
| | Positive control, Artemether (F1) | 400 mg/kg | 8.6 ± 4.16 | 74 | 0.0006 |
| | PZQ (F1) | 50 mg/kg | 26.2 ± 9.44 | 21 | 0.2667 |
| | 29 (F2) | 25 mg/kg | 4 ± 1.41 | 88 | 0.0001 |
| | 29 (F2) | 5 mg/kg | 14.8 ± 6.61 | 55 | 0.0064 |
| | 2 (F1) | 25 mg/kg | 7.2 ± 3.9 | 78 | 0.0004 |
| | 2 (F2) | 25 mg/kg | 4.4 ± 3.91 | 87 | 0.0002 |
| | 45 (F1) | 25 mg/kg | 31.8 ± 5.76 | 4 | 0.7786 |
| | 50 (F1) | 25 mg/kg | 0.8 ± 0.84 | 98 | <0.0001 |
| Juvenile | Negative control | | 32.6 ± 10.6 | N/A | |
| | 50 (F3) | 6.25 mg/kg | 17.6 ± 12.0 | 46 | 0.689 |
| | 29 (F3) | 6.25 mg/kgl | 2.0 ± 2.6 | 94 | 0.0002 |
| | 63 (F3) | 6.25 mg/kg | 0.6 ± 1.0 | 98 | 0.0001 |
| Juvenile | Negative control | | 32.8 ± 14 | | |
| | 67 (F3) | 50 mg/kg | 0 | 100 | 0.0008 |

Preferred compounds are those which by inspection show a statistically significant (P value <0.05) reduction in worm numbers of at least 50% when administered orally in the mouse model of infection as described above. For example, compounds 2, 17, 29, 50, 63 and 67.

More preferred compounds are those which show a statistically significant (P value <0.05) reduction in worm numbers of at least 50% when administered orally in the mouse model of infection as described above in a single dose of 25 mg/kg or less. For example, compounds 2, 29, 50 and 63.

The 1st compound in Column 108 should read:
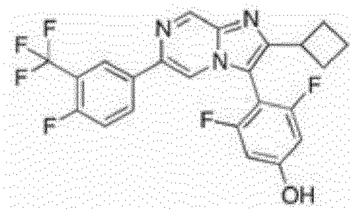
The 2nd compound in Column 108 should read:
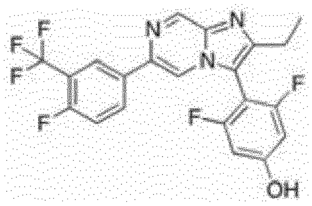

The invention claimed is:

1. A compound of formula (1a), formula (1b), formula (1c), or formula (1d):

(1a)

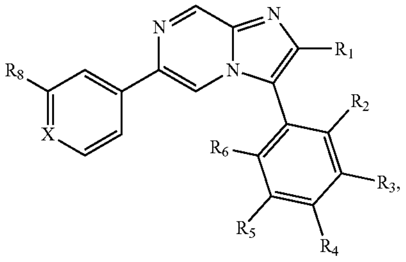

-continued (1b)

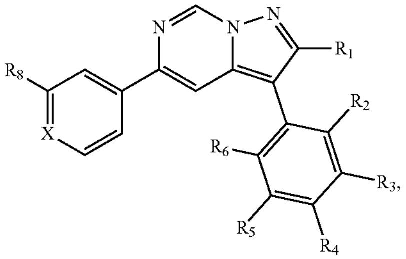

(1c)

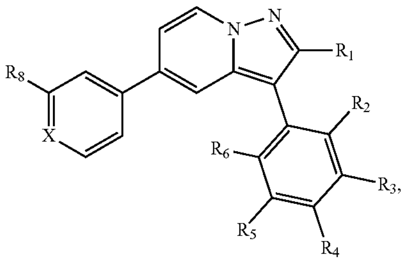

or (1d)

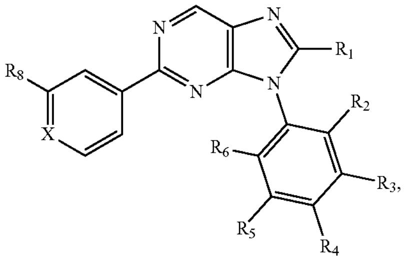

or a pharmaceutically acceptable salt thereof, wherein:

X is $CR_7$ or N;

$R_1$ is $C_1$-$C_4$ alkyl, $CH_2$—($C_3$-$C_6$ cycloalkyl), or $C_3$-$C_6$ cycloalkyl, wherein the $C_1$-$C_4$ alkyl is optionally substituted with 1, 2, 3, 4, or 5 F substituents, and the $C_3$-$C_6$ cycloalkyl is optionally substituted with 1 $CH_3$ substituent;

$R_2$ is H, F, Cl, or $OCH_3$;

$R_3$ is H, OH, $OCH_3$, $OCH_2OPO(OH)OH$, or OPO(OH)OH;

$R_4$ is H, OH, $OCH_3$, $OCH_2OPO(OH)OH$, or OPO(OH)OH; or $R_3$ and $R_4$, together with the phenyl ring to which they are attached, form an indazolyl selected from the group consisting of:

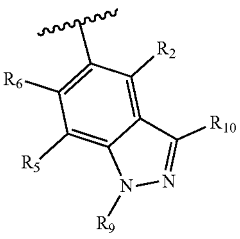

and

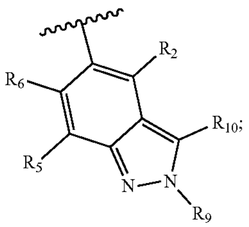

$R_5$ is H, F, Cl, or $OCH_3$;

$R_6$ is H, F, Cl, or $OCH_3$;

$R_7$ is H or F;

$R_8$ is Br, $C_1$-$C_3$ alkyl, $OC_1$-$C_3$ alkyl, $OCH_2C{\equiv}CH$, $SF_5$, or $C_3$-$C_4$ cycloalkyl, wherein the $C_1$-$C_3$ alkyl or $OC_1$-$C_3$ alkyl is optionally substituted with 1, 2, 3, 4, 5, 6, or 7 F substituents;

$R_9$ is H; and $R_{10}$ is H, F, or $CH_3$;

with the proviso that $R_3$ and $R_4$ are not both H.

2. The compound according to claim 1, or a pharmaceutically acceptable salt thereof, wherein X is $CR_7$.

3. The compound according to claim 1, or a pharmaceutically acceptable salt thereof, wherein $R_1$ is $CH_3$, $CHF_2$, $CF_3$, $CH_2CH_3$, $CH_2CF_3$, $CH_2CH_2CH_3$, $CH(CH_3)_2$, $CH_2$-(cyclopropyl), cyclopropyl, or cyclobutyl, wherein the cyclopropyl is optionally substituted with 1 $CH_3$ substituent.

4. The compound according to claim 2, or a pharmaceutically acceptable salt thereof, wherein $R_1$ is $CF_3$, $CH_2CH_3$, $CH_2CF_3$, $CH(CH_3)_2$, cyclopropyl, or cyclobutyl.

5. The compound according to claim 1, or a pharmaceutically acceptable salt thereof, wherein $R_2$ is H, F, or Cl.

6. The compound according to claim 5, or a pharmaceutically acceptable salt thereof, wherein $R_2$ is F or Cl.

7. The compound according to claim 1, or a pharmaceutically acceptable salt thereof, wherein $R_3$ is H, OH, $OCH_3$, or OPO(OH)OH.

8. The compound according to claim 7, or a pharmaceutically acceptable salt thereof, wherein $R_3$ is H.

9. The compound according to claim 1, or a pharmaceutically acceptable salt thereof, wherein $R_4$ is H, OH, $OCH_3$, or OPO(OH)OH.

10. The compound according to claim 9, or a pharmaceutically acceptable salt thereof, wherein $R_4$ is OH.

11. The compound according to claim 1, or a pharmaceutically acceptable salt thereof, wherein $R_3$ and $R_4$, together with the phenyl ring to which they are attached, form an indazolyl selected from the group consisting of:

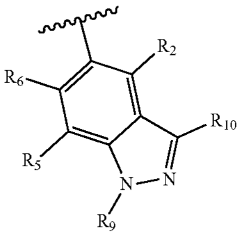

and

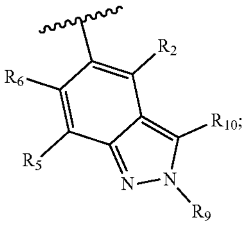

wherein:

$R_9$ is H; and $R_{10}$ is H.

12. The compound according to claim 1, or a pharmaceutically acceptable salt thereof, wherein $R_5$ is H or $OCH_3$.

13. The compound according to claim 12, or a pharmaceutically acceptable salt thereof, wherein $R_5$ is H.

14. The compound according to claim 1, or a pharmaceutically acceptable salt thereof, wherein $R_6$ is H or F.

15. The compound according to claim 1, or a pharmaceutically acceptable salt thereof, wherein $R_8$ is $CF_3$, $CH_2CF_3$, $CF_2CF_3$, $CH(CH_3)_2$, $OCF_3$, $OCH(CH_3)_2$, $SF_5$, cyclopropyl, or cyclobutyl.

16. The compound according to claim 1, or a pharmaceutically acceptable salt thereof, wherein

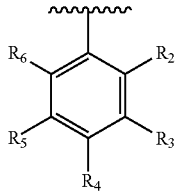

is selected from the group consisting of:

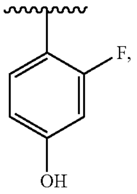

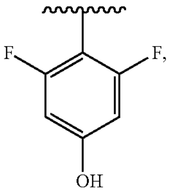

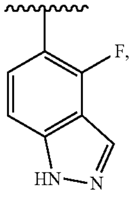

and

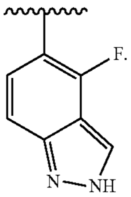

17. The compound according to claim 1, or a pharmaceutically acceptable salt thereof, wherein

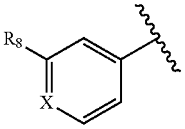

is selected from the group consisting of:

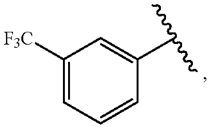
,
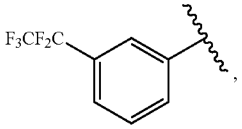
,
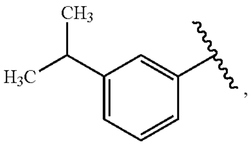
,
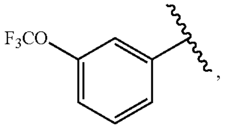
,
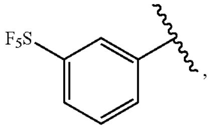
,
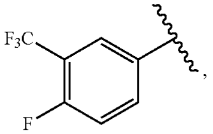
,
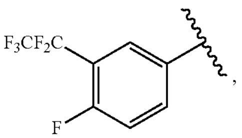
,
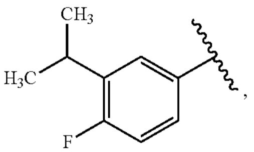
, -continued

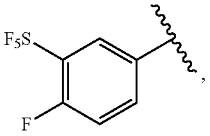
,
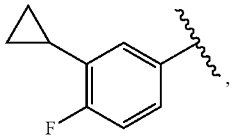
, and
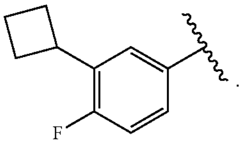
.

18. The compound according to claim 1, wherein the compound is:

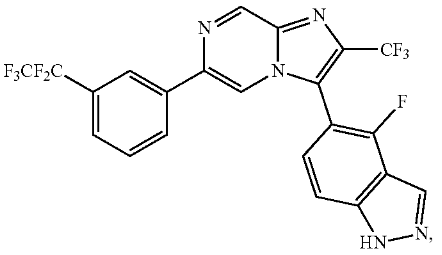

or a pharmaceutically acceptable salt thereof.

19. The compound according to claim 1, wherein the compound is:

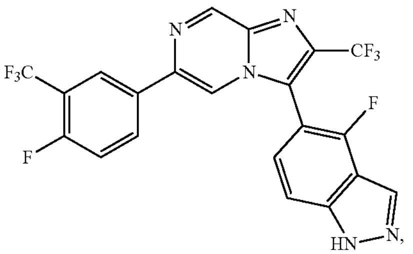 [SMILES: Fc1ccc(-c2cn3c(-c4ccc5[nH]ncc5c4F)c(C(F)(F)F)nc3cn2)cc1C(F)(F)F]

or a pharmaceutically acceptable salt thereof.

20. The compound according to claim 1, wherein the compound is:

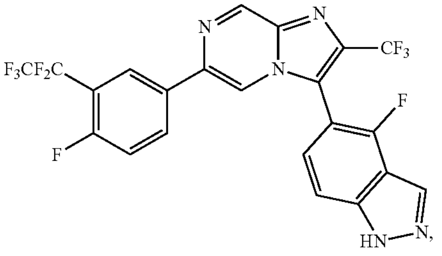

or a pharmaceutically acceptable salt thereof.

21. The compound according to claim 1, wherein the compound is:

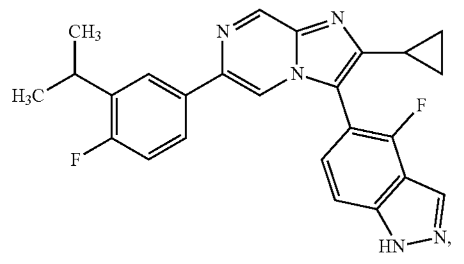 [SMILES: CC(C)c1cc(-c2cn3c(-c4ccc5[nH]ncc5c4F)c(C4CC4)nc3cn2)ccc1F]

or a pharmaceutically acceptable salt thereof.

22. The compound according to claim 1, wherein the compound is:

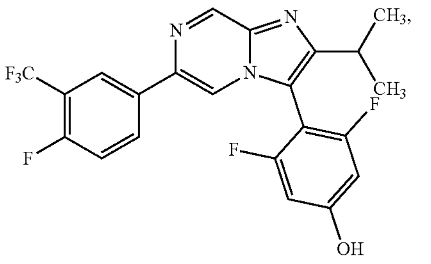 [SMILES: CC(C)c1nc2cnc(-c3ccc(F)c(C(F)(F)F)c3)cn2c1-c1c(F)cc(O)cc1F]

or a pharmaceutically acceptable salt thereof.

23. A pharmaceutical composition comprising a pharmaceutically acceptable excipient and a therapeutically effective amount of a compound according to claim 1, or a pharmaceutically acceptable salt thereof.

24. A method for treating schistosomiasis in a patient, comprising administering to a patient in need thereof a therapeutically effective amount of a compound according to claim 1, or a pharmaceutically acceptable salt thereof.

25. A compound of formula (1a') or formula (1b'):

(1a')

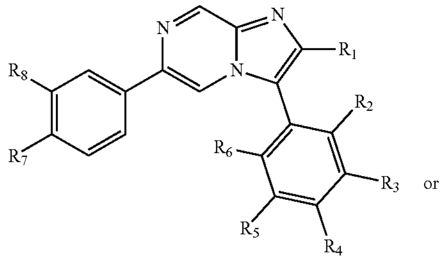

or (1b')

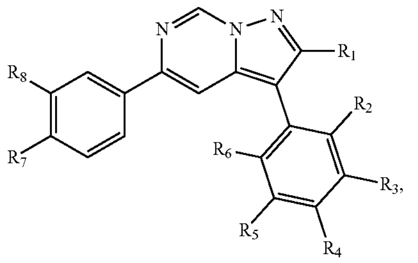

or a pharmaceutically acceptable salt thereof, wherein:

$R_1$ is $C_1$-$C_4$ alkyl, $CH_2$—($C_3$-$C_6$ cycloalkyl), or $C_3$-$C_6$ cycloalkyl, wherein the $C_1$-$C_4$ alkyl is optionally substituted with 1, 2, 3, 4, or 5 F substituents, and the $C_3$-$C_6$ cycloalkyl is optionally substituted with 1 $CH_3$ substituent;

$R_2$ is H, F, Cl, or $OCH_3$;

$R_3$ is H, OH, $OCH_3$, $OCH_2OPO(OH)OH$, or OPO(OH)OH;

$R_4$ is H, OH, $OCH_3$, $OCH_2OPO(OH)OH$, or OPO(OH)OH; or $R_3$ and $R_4$, together with the phenyl ring to which they are attached, form an indazolyl selected from the group consisting of:

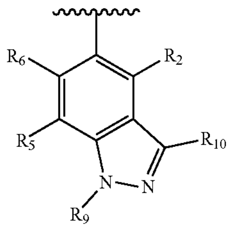

and

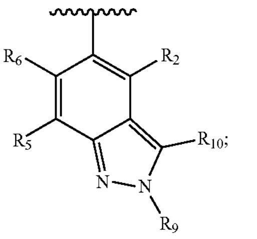

$R_5$ is H, F, Cl, or $OCH_3$;

$R_6$ is H, F, Cl, or $OCH_3$;

$R_7$ is H or F;

$R_8$ is $C_1$-$C_3$ alkyl or $SF_5$, wherein the $C_1$-$C_3$ alkyl is optionally substituted with 1, 2, 3, 4, 5, 6, or 7 F substituents;

$R_9$ is H; and $R_{10}$ is H, F, or $CH_3$;

with the proviso that $R_3$ and $R_4$ are not both H.

26. A compound selected from the group consisting of:

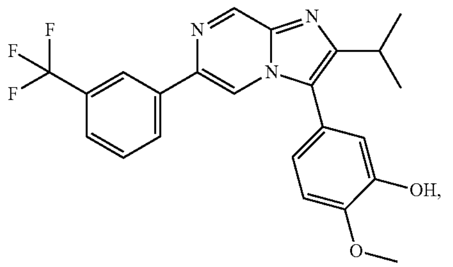

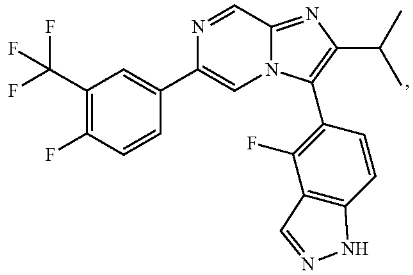

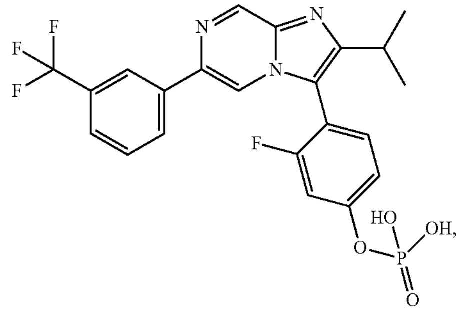

-continued
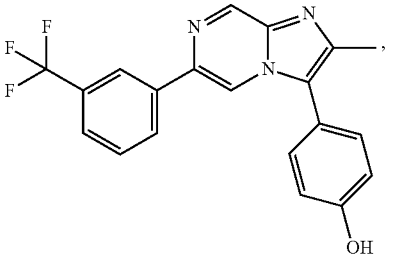
,
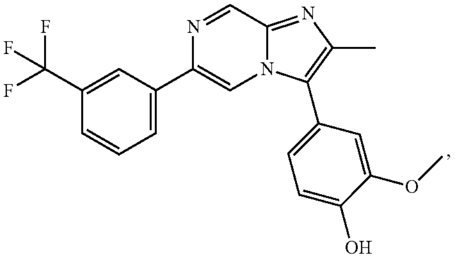
,
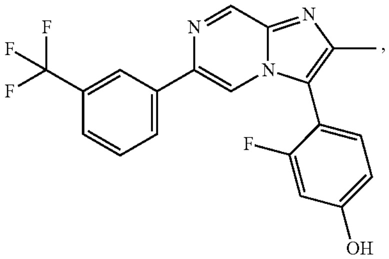
,
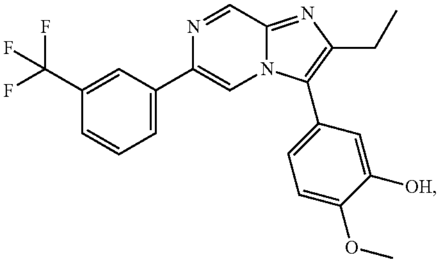
,
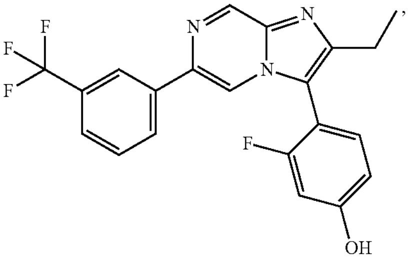
,
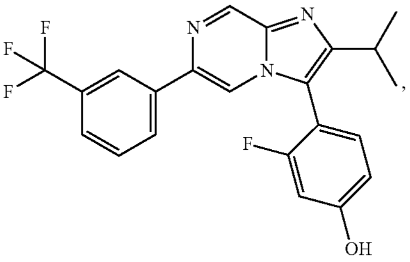
,
-continued
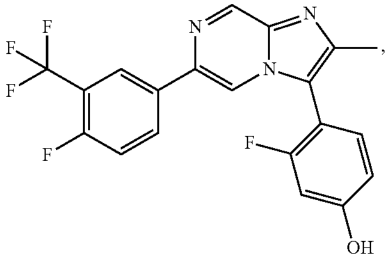
,
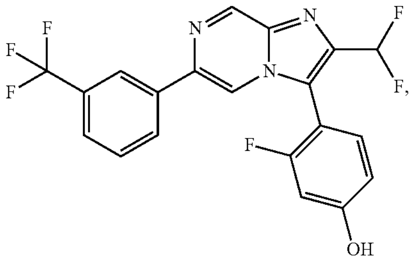
,
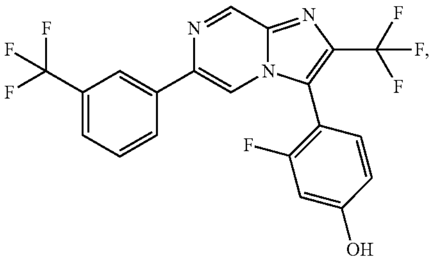
,
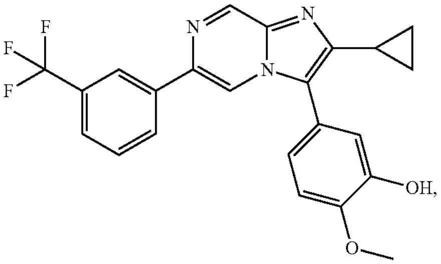
,
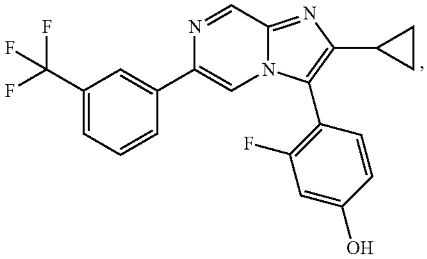
,
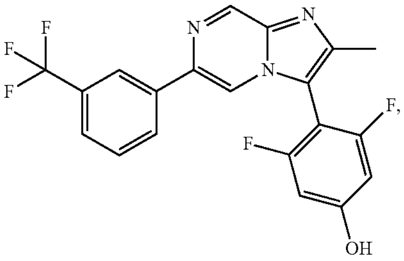
, -continued
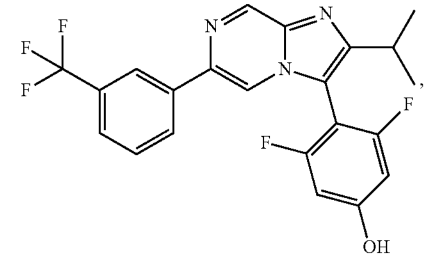
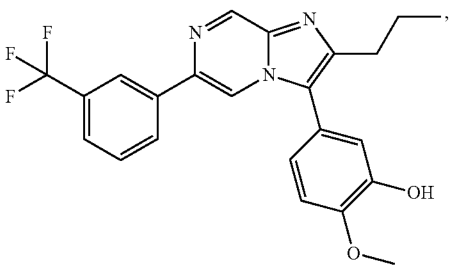
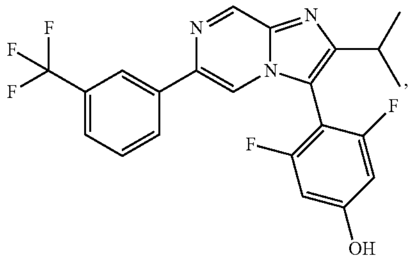
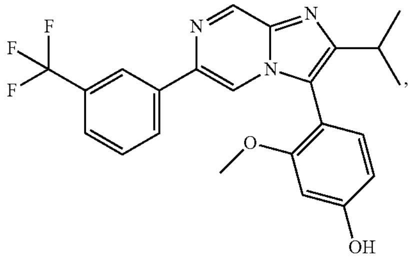
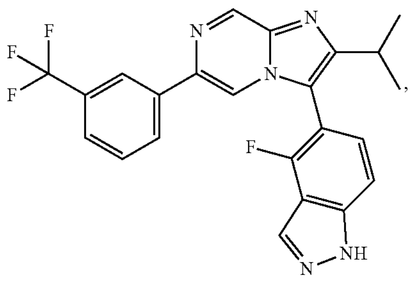
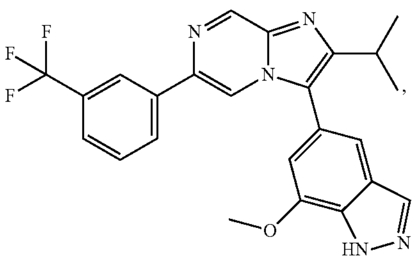
-continued
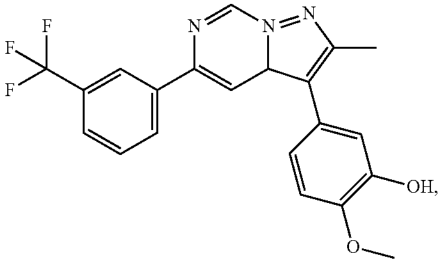
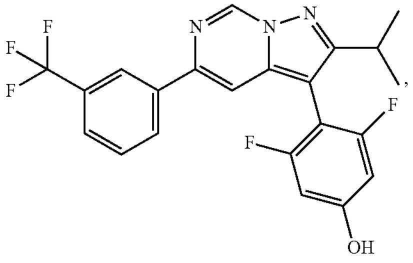
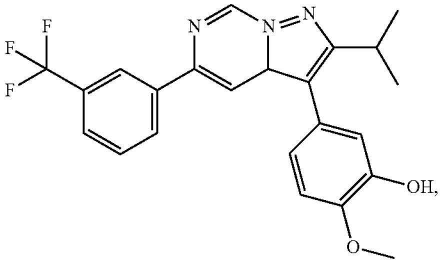
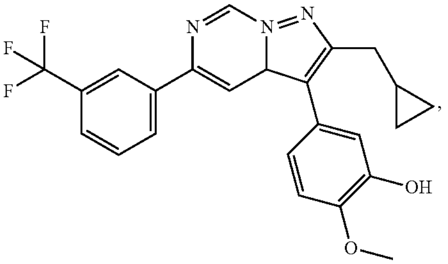
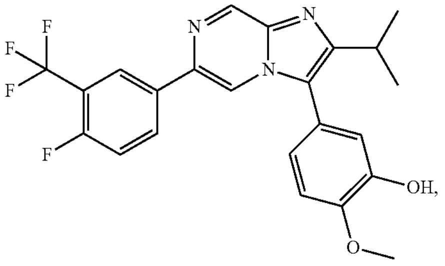
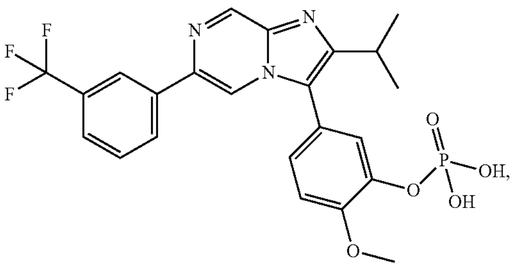

-continued
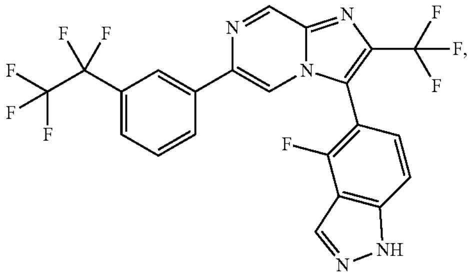
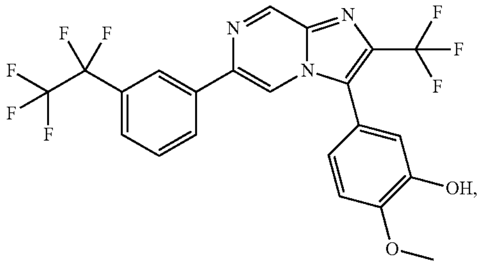
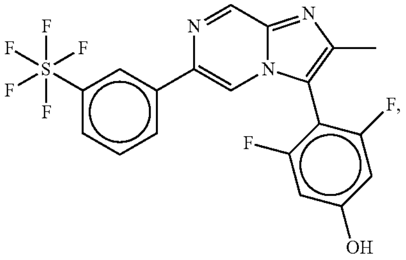
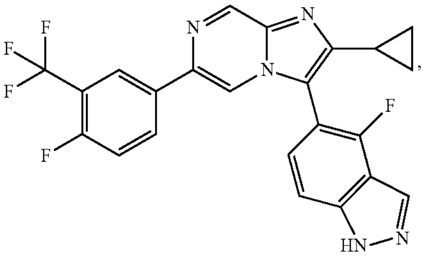
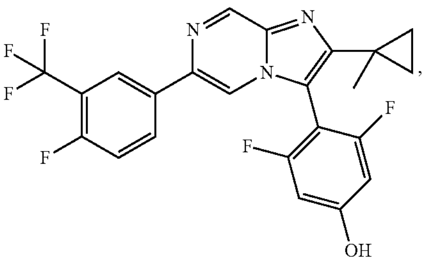
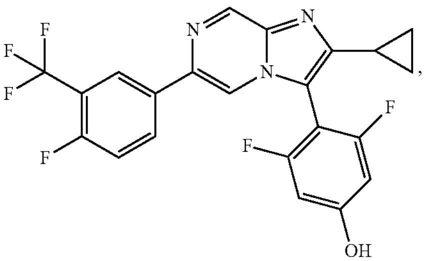
-continued
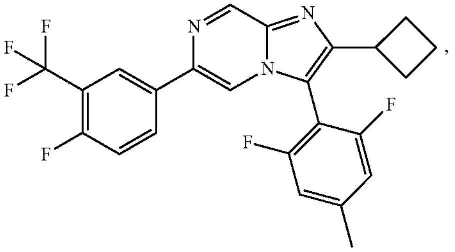
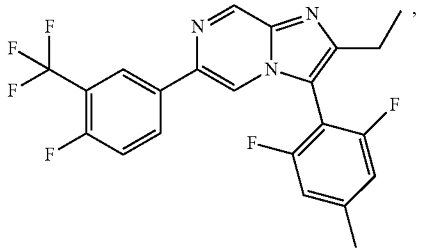
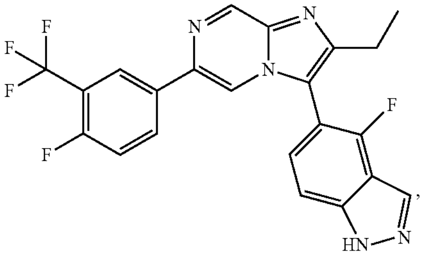
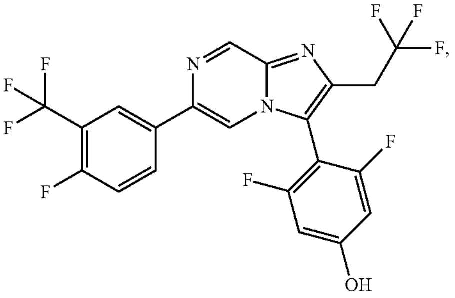
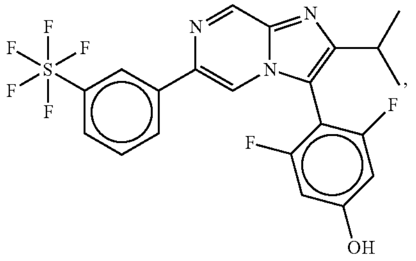
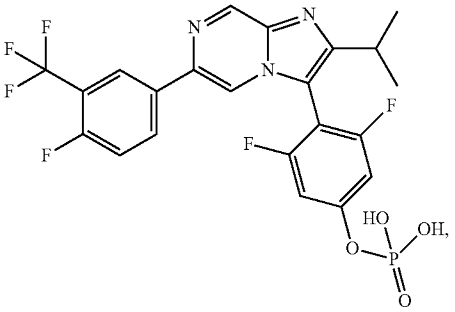

-continued
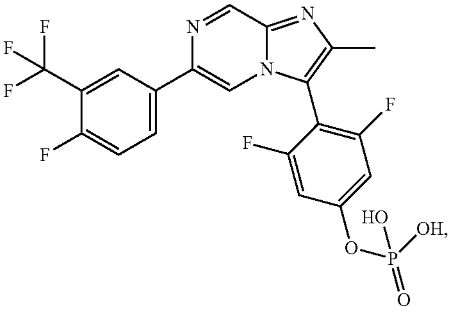
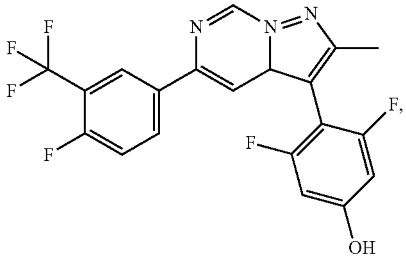
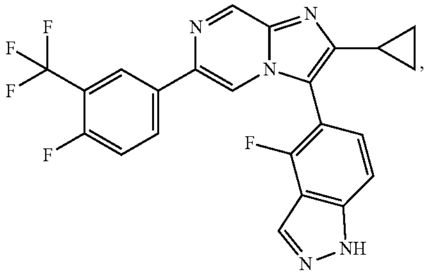
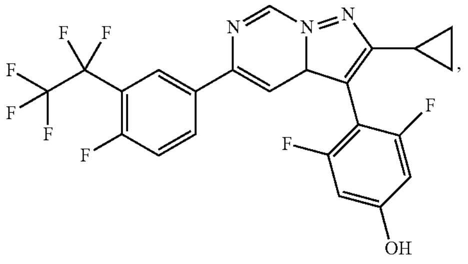
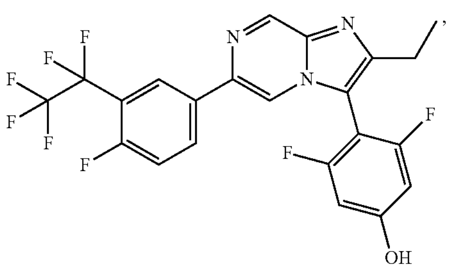
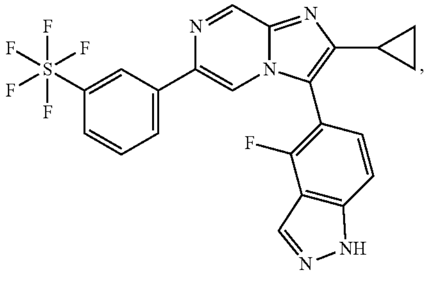
-continued
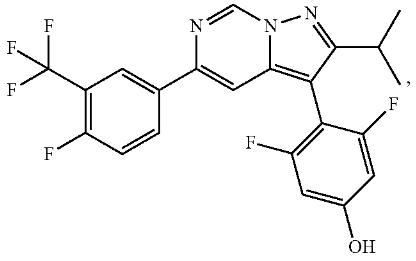
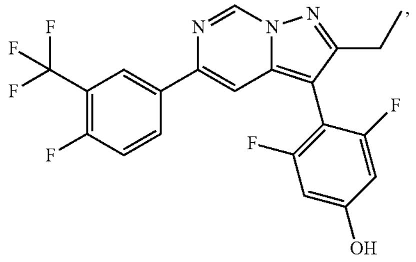
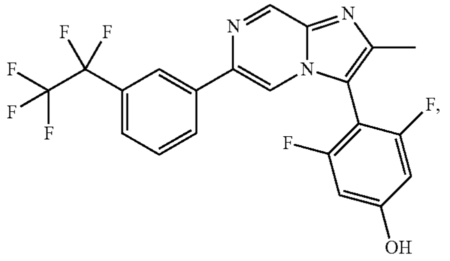
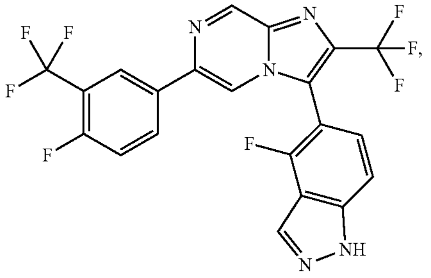
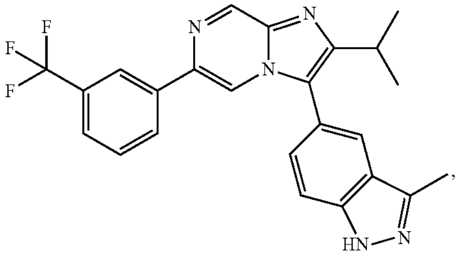
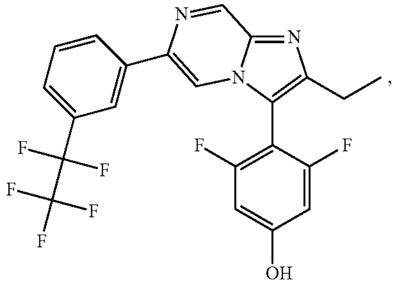

-continued
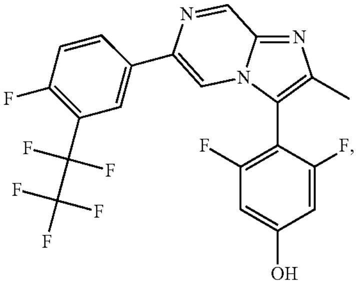
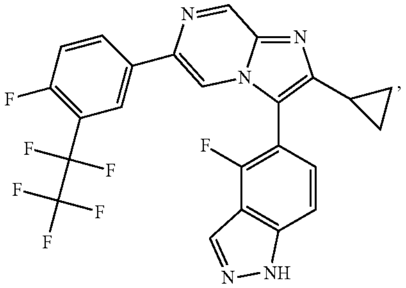
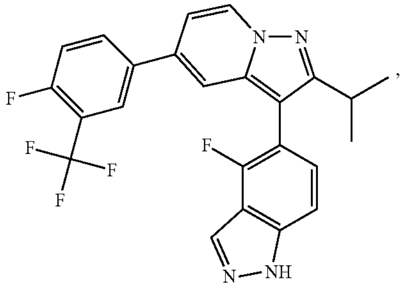
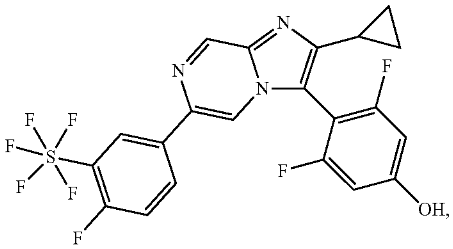
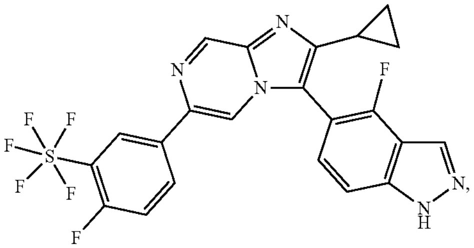
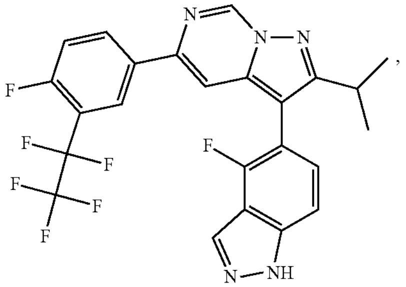
-continued
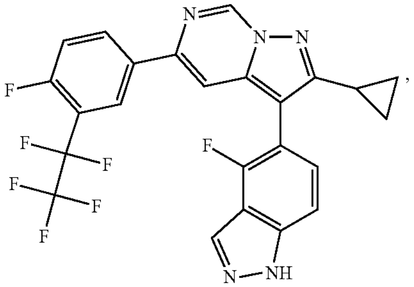
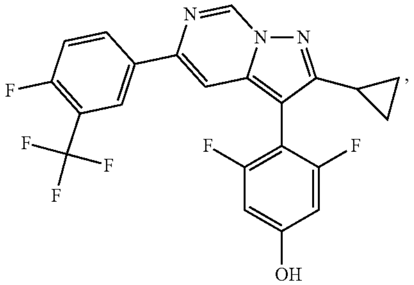
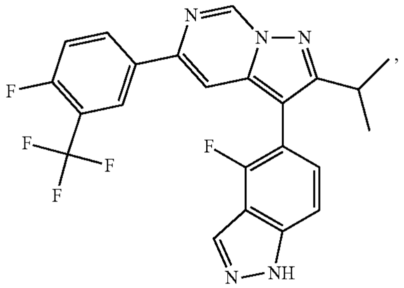
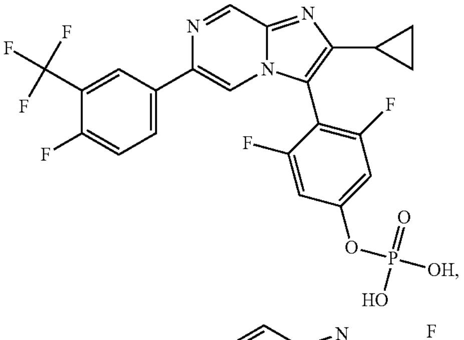
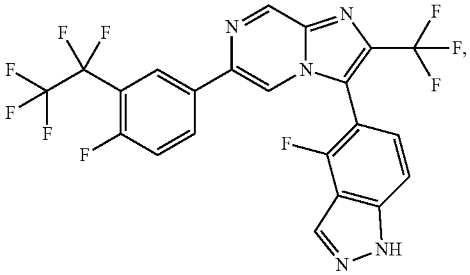
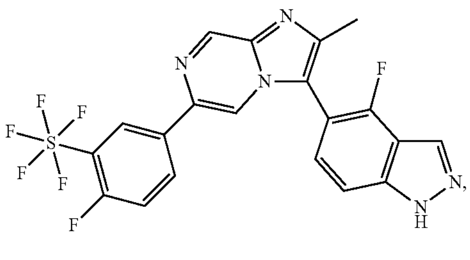

-continued
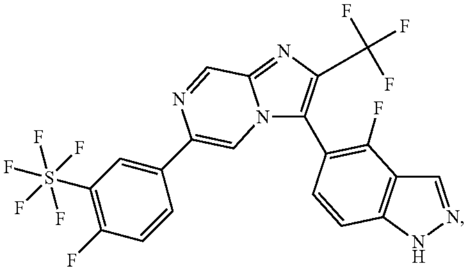
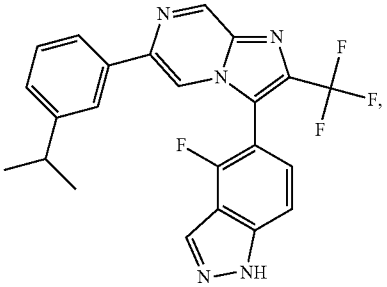
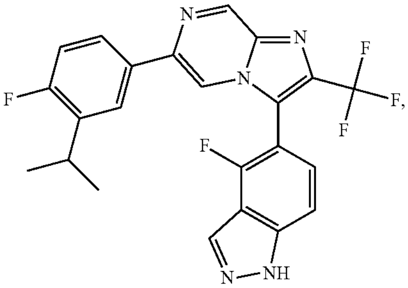
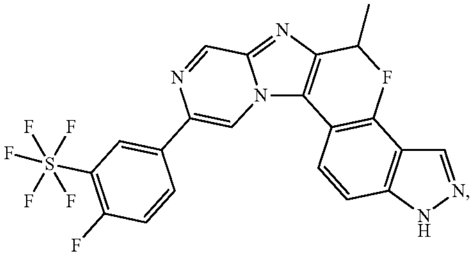
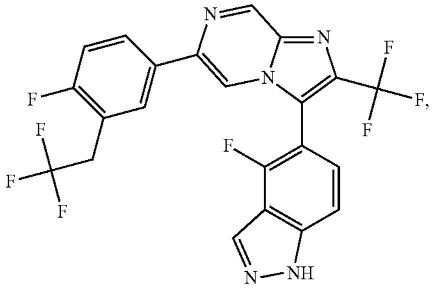
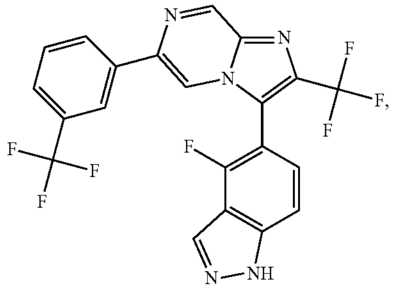
-continued
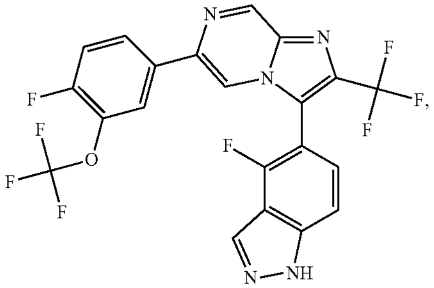
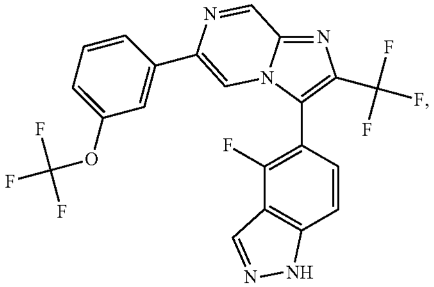
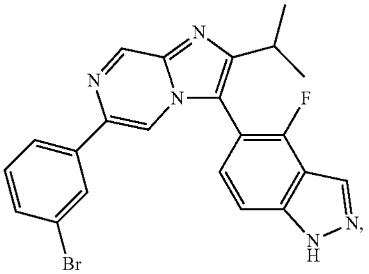
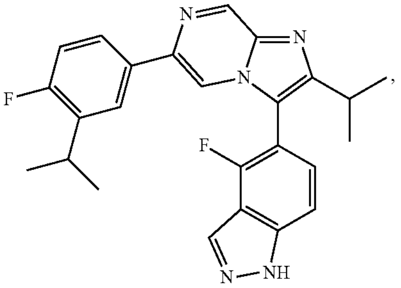
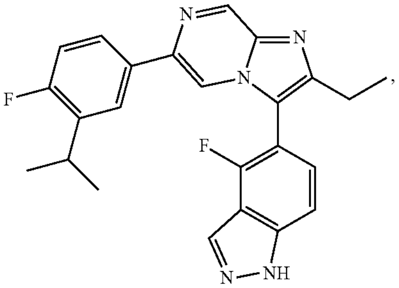
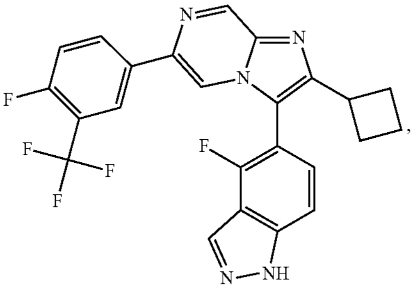

-continued
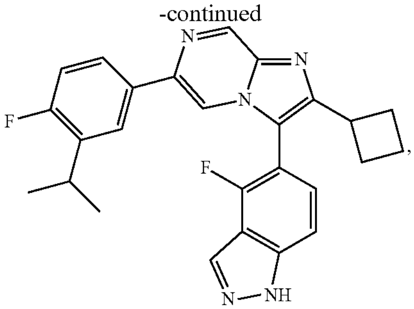,
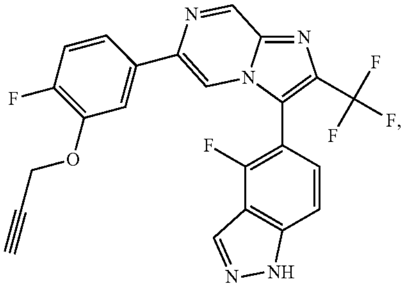,
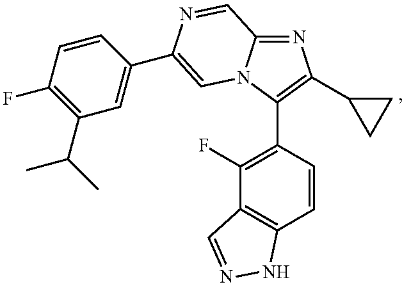,
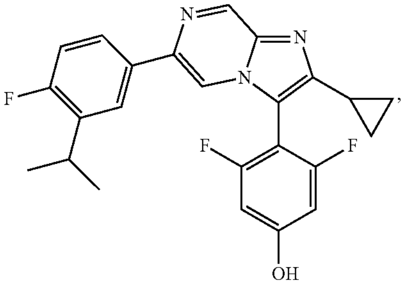,
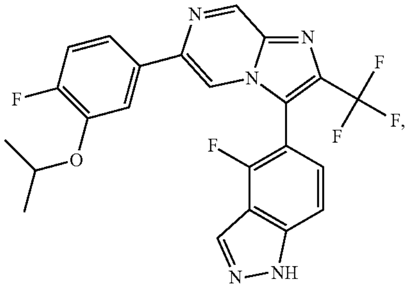,
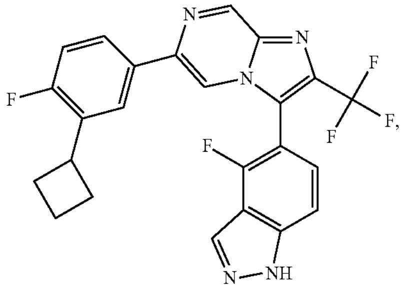,
-continued
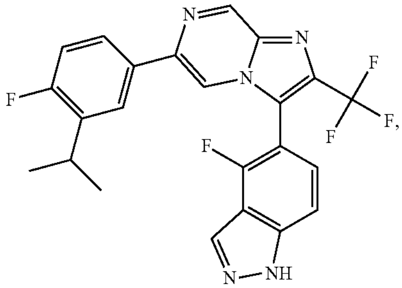,
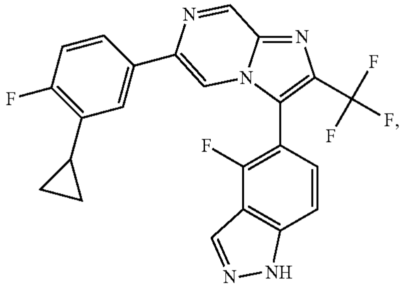,
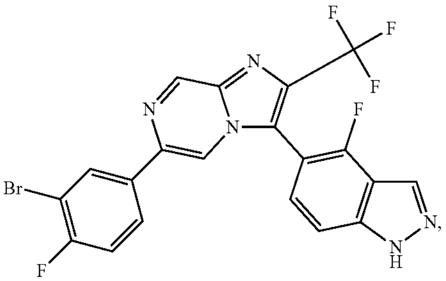,
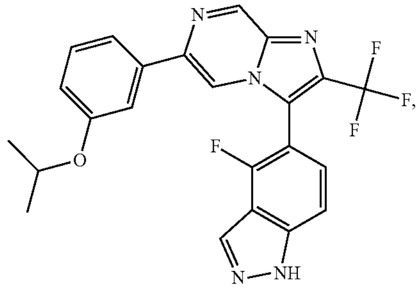,
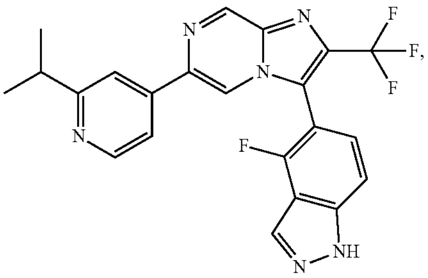,
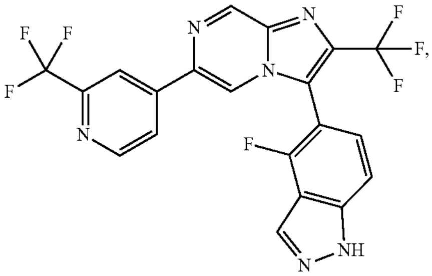, -continued
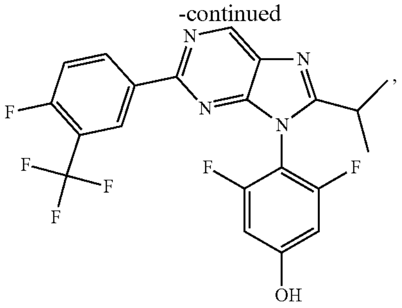
, and
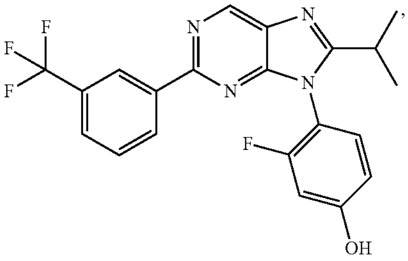
,
or a pharmaceutically acceptable salt thereof.
* * * * *

UNITED STATES PATENT AND TRADEMARK OFFICE

CERTIFICATE OF CORRECTION

PATENT NO. : 11,046,700 B2
APPLICATION NO. : 16/477574
DATED : June 29, 2021
INVENTOR(S) : John Mark Francis Gardner and Andrew Simon Bell It is certified that error appears in the above-identified patent and that said Letters Patent is hereby corrected as shown below:

In the Claims

Claim 4 reads:
The compound according to claim 2, or a pharmaceutically acceptable salt thereof, wherein R1 is CF3, CH2CH3, CH2CF3, CH(CH3)2, cyclopropyl or cyclobutyl.

Should be:
The compound according to claim 3, or a pharmaceutically acceptable salt thereof, wherein R1 is CF3, CH2CH3, CH2CF3, CH(CH3)2, cyclopropyl or cyclobutyl.

Claim 26:

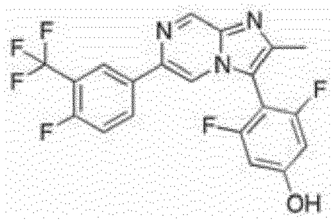 is missing (should be between the last compound in Column 104 and 1st compound in Column 105)

The 1st compound in Column 105 should read:

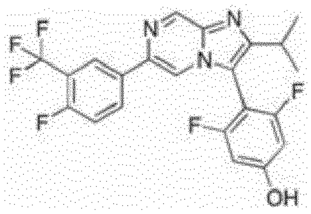

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*